(12) United States Patent
Guillemont et al.

(10) Patent No.: US 9,617,262 B2
(45) Date of Patent: *Apr. 11, 2017

(54) ANTIBACTERIAL CYCLOPENTAL[C]PYRROLE SUBSTITUTED 3,4-DIHYDRO-1H-[1,8]NAPHTHYRIDINONES

(71) Applicant: Janssen Sciences Ireland UC, County Cork (IE)

(72) Inventors: Jerome Emile Georges Guillemont, Ande (FR); David Francis Alain Lancois, Louviers (FR); Magali Madeleine Simone Motte, Louviers (FR); Anil Koul, Edegem (BE); Wendy Mia Albert Balemans, Kalmthout (BE); Eric Pierre Alexandre Arnoult, Le Vaudreuil (FR)

(73) Assignee: Janssen Sciences Ireland UC, County Cork (IE)

( * ) Notice: Subject to any disclaimer, the term of this patent is extended or adjusted under 35 U.S.C. 154(b) by 0 days.

This patent is subject to a terminal disclaimer.

(21) Appl. No.: 15/071,612

(22) Filed: Mar. 16, 2016

(65) Prior Publication Data

US 2016/0194324 A1  Jul. 7, 2016

Related U.S. Application Data

(63) Continuation of application No. 14/552,108, filed on Nov. 24, 2014, now Pat. No. 9,290,493, which is a continuation of application No. 14/237,862, filed as application No. PCT/EP2012/065733 on Aug. 10, 2012, now Pat. No. 8,906,923.

(30) Foreign Application Priority Data

Aug. 10, 2011 (EP) ...................... 11177119

(51) Int. Cl.
  *C07D 471/04* (2006.01)
  *A61K 31/44* (2006.01)
  *C07D 487/04* (2006.01)
  *C07D 519/00* (2006.01)

(52) U.S. Cl.
  CPC ......... *C07D 471/04* (2013.01); *C07D 487/04* (2013.01); *C07D 519/00* (2013.01)

(58) Field of Classification Search
  CPC .... C07D 471/04; A61K 31/50; A61K 31/495; A61K 31/44
  USPC .................. 546/122; 514/250, 300
  See application file for complete search history.

(56) References Cited

U.S. PATENT DOCUMENTS

| | | | |
|---|---|---|---|
| 4,215,123 A | 7/1980 | Scotese et al. | |
| 8,906,923 B2 * | 12/2014 | Guillemont | C07D 471/04 514/250 |
| 9,290,493 B2 * | 3/2016 | Guillemont | C07D 471/04 |
| 2014/0163038 A1 | 6/2014 | Guillemont et al. | |
| 2014/0171418 A1 | 6/2014 | Guillemont et al. | |
| 2014/0171451 A1 | 6/2014 | Guillemont et al. | |

FOREIGN PATENT DOCUMENTS

| | | |
|---|---|---|
| WO | WO 01/26652 A1 | 4/2001 |
| WO | WO 01/26654 A1 | 4/2001 |
| WO | WO 01/27103 A1 | 4/2001 |
| WO | WO 03/088897 A2 | 10/2003 |
| WO | WO 2006/101603 A | 9/2006 |
| WO | WO 2007/043835 A1 | 4/2007 |
| WO | WO 2007/053131 A2 | 5/2007 |
| WO | WO 2008/009122 A1 | 1/2008 |
| WO | WO 2008/098374 A1 | 8/2008 |
| WO | WO 2011/061214 A1 | 5/2011 |

OTHER PUBLICATIONS

Bergler et al, "The enoyl-[acyl-carrier-protein] reductase (FabI) of *Escherichia coli*, which catalyzes a key regulatory step in fatty acid biosynthesis, accepts NADH and NADPH as cofactors and is inhibited by palmitoyl-CoA", *European Journal of Biochemistry* (1996) 242:689-694.

Heath et al, "Enoyl-acyl carrier protein reductase (fabI) plays a determinant role in completing cycles of fatty acid elongation in *Escherichia coli*", *Journal of Biological Chemistry*(1995) 270:26538-42.

U.S. Appl. No. 14/237,841, Guillemont, filed Feb. 7, 2014.
U.S. Appl. No. 14/237,851, Guillemont, filed Feb. 7, 2014.
U.S. Appl. No. 14/237,862, Guillemont, filed Feb. 7, 2014.

* cited by examiner

*Primary Examiner* — Niloofar Rahmani

(57) ABSTRACT

The present invention is related to novel compounds of formula (I) that inhibit the activity of the FabI enzyme which are therefore useful in the treatment of bacterial infections. It further relates to pharmaceutical compositions comprising these compounds, and chemical processes for preparing these compounds.

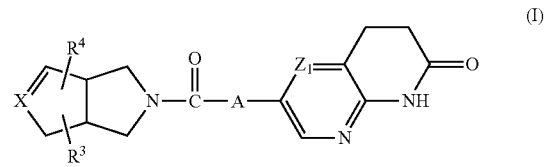

(I)

2 Claims, No Drawings

ANTIBACTERIAL CYCLOPENTAL[C]PYRROLE SUBSTITUTED 3,4-DIHYDRO-1H-[1,8]NAPHTHYRIDINONES

This application is a continuation application of pending U.S. application Ser. No. 14/552,108, filed Nov. 24, 2014, which is a continuation application of U.S. Ser. No. 14/237, 862, filed Feb. 7, 2014, now U.S. Pat. No. 8,906,923, which is a 35 U.S.C. 371 nationalization of PCT application PCT/EP2012/065733, filed Aug. 10, 2012, which claims priority to application EP 11177119.2, filed Aug. 10, 2011.

The present invention is related to novel compounds of formula (I) that inhibit the activity of the FabI enzyme which are therefore useful in the treatment of bacterial infections. It further relates to pharmaceutical compositions comprising these compounds, and chemical processes for preparing these compounds.

The compounds of the present invention are antibacterial compounds that inhibit the FabI protein, a NADH-dependent enoyl-acyl carrier protein (ACP) reductase enzyme in the fatty acid biosynthesis pathway. Fatty acid synthase (FAS) is involved in the overall biosynthetic pathway of saturated fatty acids in all organisms, but the structural organization of FAS varies considerably among them. The distinctive characteristics of FAS of vertebrates and yeasts are that all enzymatic activities are encoded on one or two polypeptide chains, and that the acyl carrier protein (ACP) exists in the form of a complex. In contrast, in bacterial FAS, each of synthetic steps is catalyzed by a distinct, mono-functional enzyme and the ACP is a discrete protein. Therefore, it is possible to selectively inhibit bacterial FAS by blocking one of the synthetic steps using an inhibitory agent. NADH-dependent enoyl-ACP reductase (Fab I) is involved in the last step of the four reaction steps involved in each cycle of bacterial fatty acid biosynthesis. Thus, the FabI enzyme is the biosynthetic enzyme in the overall synthetic pathway of bacterial fatty acid biosynthesis.

The FabI enzyme has been shown to constitute an essential target in major pathogens such as E. Coli (Heath et al. J. Biol. Chem. 1995, 270, 26538; Bergler et al. Eur. J. Biochem. 2000, 275, 4654). Hence, compounds that inhibit FabI may be useful as antibacterials.

Compounds having FabI enzyme inhibitory activity have been disclosed in WO-01/26652, WO-01/26654, and WO-01/27103. Substituted naphthyridinone compounds having FabI inhibitory activity have been disclosed in WO-03/088897, WO-2007/043835 and WO-2008/098374. International patent application WO 2007/053131 discloses various compounds for potential use as FabI inhibitors. International patent application WO 2011/061214 also discloses various compounds for potential use as FabI inhibitors. However, none of these documents disclose a fused-bicyclic moiety that is directly attached to a carbonyl moiety that is a to an alkene.

The present invention relates to a compound of formula (I)

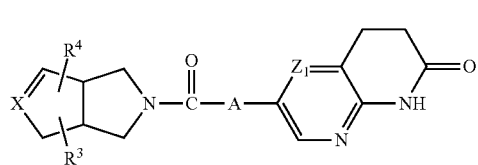

wherein
A represents —C≡C— or

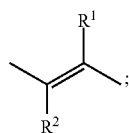

the ═══ bond represents a single bond or a double bond,
X represents carbon or nitrogen, and when X represents nitrogen then the ═══ bond represents a single bond;
$Z_1$ represents CH or N;
$R^1$ is hydrogen, $C_{1-4}$alkyl or halo;
$R^2$ is hydrogen, $C_{1-4}$alkyl or halo;
$R^3$ is hydrogen, $C_{1-6}$alkyl, hydroxy or halo;
$R^4$ is hydrogen; halo; $C_{1-6}$alkyl; $C_{2-6}$alkenyl; $C_{2-6}$alkynyl; $C_{1-6}$alkyloxy; $C_{1-4}$alkyloxycarbonyl; aminocarbonyl; mono- or di($C_{1-4}$alkyl)-aminocarbonyl; aryl; aryloxy; arylcarbonyl; arylsulfonyl; heteroaryl; $C_{1-6}$alkyl substituted with cyano; $C_{1-6}$alkyl substituted with aryl or aryloxy; or $C_{1-6}$alkyl substituted with heteroaryl;
aryl is phenyl; phenyl substituted with one, two or three substituents each individually selected from halo, hydroxy, $C_{1-4}$alkyl, $C_{1-4}$alkyloxy, polyhalo$C_{1-4}$alkyl, polyhalo$C_{1-4}$alkyloxy, cyano, nitro, and amino;
heteroaryl is furanyl, thiophenyl, pyrrolyl, pyrazolyl, imidazolyl, isoxazolyl, thiazolyl, triazolyl, tetrazolyl, isothiazolyl, thiadiazolyl, oxadiazolyl, pyridinyl, pyridazinyl, pyrimidinyl, pyrazinyl, benzo[1,3]dioxolyl, benzofuranyl, benzothiazolyl, indolyl, 2,3-dihydro-1H-indolyl, tetrahydrothiophenyl, or quinolinyl,
wherein each heteroaryl may be substituted with one or two substituents each independently selected from halo, cyano, $C_{1-4}$alkyl, $C_{1-4}$alkyloxy, $C_{1-4}$alkylcarbonyl, or phenyl;
or a pharmaceutically acceptable acid addition salt thereof.
As used in the foregoing definitions:
halo is generic to fluoro, chloro, bromo and iodo;
$C_{1-4}$alkyl defines straight and branched chain saturated hydrocarbon radicals having from 1 to 4 carbon atoms such as, for example, methyl, ethyl, propyl, butyl, 1-methyl-ethyl, 2-methylpropyl and the like;
$C_{1-6}$alkyl is meant to include $C_{1-4}$alkyl and the higher homologues thereof having 5 or 6 carbon atoms, such as, for example, 2-methylbutyl, pentyl, hexyl and the like;
polyhalo$C_{1-4}$alkyl is defined as polyhalo substituted $C_{1-4}$alkyl (as hereinabove defined) substituted with 2 to 6 halogen atoms such as difluoromethyl, trifluoromethyl, trifluoroethyl, and the like.

As used in the description, whenever the term "compound of formula (I)" is used, it is meant to include also the pharmaceutically addition salts the compounds of formula (I) are able to form and the solvates the compounds of formula (I) or the pharmaceutically acceptable acid addition salts of compounds of formula (I) are able to form.

The definition of "compounds of formula (I)" inherently includes all stereoisomers of the compound of formula (I) either as a pure stereoisomer or as a mixture of two or more stereoisomers. Enantiomers are stereoisomers that are non-superimposable mirror images of each other. A 1:1 mixture of a pair of enantiomers is a racemate or racemic mixture. Diastereomers (or diastereoisomers) are stereoisomers that are not enantiomers, i.e. they are not related as mirror images. If a compound contains a disubstituted cycloalkyl group, the substituents may be in the cis or trans configuration. Therefore, the invention includes enantiomers, diastereomers, racemates, cis isomers, trans isomers and mixtures thereof.

The absolute configuration is specified according to the Cahn-Ingold-Prelog system. The configuration at an asymmetric atom is specified by either R or S. Resolved compounds whose absolute configuration is not known can be designated by (+) or (−) depending on the direction in which they rotate plane polarized light. When a specific stereoisomer is identified, this means that said stereoisomer is substantially free, i.e. associated with less than 50%, preferably less than 20%, more preferably less than 10%, even more preferably less than 5%, in particular less than 2% and most preferably less than 1%, of the other isomers. Thus, when a compound of formula (I) is for instance specified as (R), this means that the compound is substantially free of the (S) isomer; when a compound of formula (I) is for instance specified as E, this means that the compound is substantially free of the Z isomer; when a compound of formula (I) is for instance specified as cis, this means that the compound is substantially free of the trans isomer.

The terms "stereoisomers" or "stereochemically isomeric forms" hereinbefore or hereinafter are used interchangeably.

The absolute stereochemical configuration of the compounds of formula (I) and of the intermediates used in their preparation may easily be determined by those skilled in the art while using well-known methods such as, for example, X-ray diffraction.

Some of the compounds of formula (I) may also exist in their tautomeric form. Such forms although not explicitly indicated in the above formula are intended to be included within the scope of the present invention.

Furthermore, some compounds of formula (I) and some of the intermediates used in their preparation may exhibit polymorphism. It is to be understood that the present invention encompasses any polymorphic forms possessing properties useful in the treatment of the conditions noted hereinabove.

The pharmaceutically acceptable acid addition salts as mentioned hereinabove are meant to comprise the therapeutically active non-toxic acid addition salt forms that the compounds of formula (I) are able to form. These pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids.

Conversely said salt forms can be converted by treatment with an appropriate base into the free base form.

The compounds of formula (I) may exist in both unsolvated and solvated forms. The term 'solvate' is used herein to describe a molecular association comprising a compound of the invention and one or more pharmaceutically acceptable solvent molecules, e.g. water or ethanol. The term 'hydrate' is used when said solvent is water.

The term "FabI" is art-recognized and refers to the bacterial enzyme believed to function as an enoyl-acyl carrier protein (ACP) reductase in the final step of the four reactions involved in each cycle of bacterial fatty acid biosynthesis. This enzyme is believed to be widely distributed in bacteria.

Compounds of formula (I) that may be mentioned include those in which:

(i) $Z_1$ represents CH, and hence the compound of formula I represents the following:

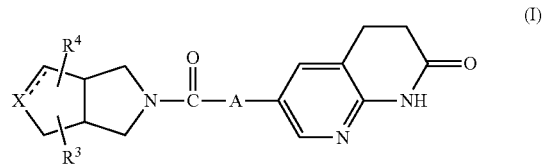

wherein (ii) when $R^1$ or $R^2$ represent halo, then they are preferably F or Cl;

(iii) $R^1$ represents hydrogen or $C_{1-4}$alkyl; and/or (iv) $R^2$ represents hydrogen or $C_{1-4}$alkyl.

Preferred compounds of formula (I) include those in which A represents a double bond (and not a triple bond), i.e. it is preferred that:

A represents

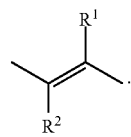

Interesting compounds of formula (I) are those compounds of formula (I) wherein one or more of the following restrictions apply:

a) $R^1$ and $R^2$ represent hydrogen; or
b) $R^3$ represents hydrogen; or
c) $R^3$ represents hydrogen, halo or hydroxy; or
d) $R^4$ represents hydrogen or halo; or
e) $R^4$ represents aryl; or
f) $R^4$ represents $C_{1-6}$alkyl; or
g) $R^4$ represents aryloxy, or arylsulfonyl; or
h) $R^4$ represents $C_{1-6}$alkyl substituted with aryl; or
i) $R^4$ represents heteroaryl; or
j) $R^4$ represents $C_{1-6}$alkyl substituted with heteroaryl; or
k) heteroaryl represents furanyl, thiophenyl, pyrazolyl, isoxazolyl, thiazolyl, triazolyl, tetrazolyl, thiadiazolyl, pyridinyl, or pyrimidinyl; or
l) X represents carbon; or
m) X represents nitrogen and the ═══ bond represents a single bond.

A first group of compounds are the compounds of formula (I)

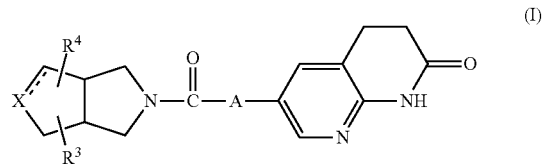

wherein
A represents —C≡C— or

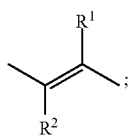

the ═══ bond represents a single bond or a double bond,
X represents carbon or nitrogen, and when X represents nitrogen then the ═══ bond represents a single bond;
$R^1$ is hydrogen;
$R^2$ is hydrogen;
$R^3$ is hydrogen, hydroxy or halo;
$R^4$ is hydrogen; halo; $C_{1-6}$alkyl; $C_{1-6}$alkyloxy; $C_{1-4}$alkyloxycarbonyl; aminocarbonyl; mono- or di($C_{1-4}$alkyl)-aminocarbonyl; aryl; aryloxy; arylsulfonyl; heteroaryl; $C_{1-6}$alkyl substituted with cyano; $C_{1-6}$alkyl substituted with aryl; or $C_{1-6}$alkyl substituted with heteroaryl;
aryl is phenyl; phenyl substituted with one substituent selected from halo, $C_{1-4}$alkyl, $C_{1-4}$alkyloxy, and cyano;
heteroaryl is furanyl, thiophenyl, pyrazolyl, isoxazolyl, thiazolyl, triazolyl, tetrazolyl, thiadiazolyl, pyridinyl, or pyrimidinyl;
wherein each heteroaryl may be substituted with one substituent selected from halo, cyano, $C_{1-4}$alkyl, $C_{1-4}$alkyloxy, or $C_{1-4}$alkylcarbonyl;
or a pharmaceutically acceptable acid addition salt thereof.
A second group of compounds of formula (I) are those compounds of formula (I) wherein A represents —C≡C—.
A third group of compounds of formula (I) are those compounds of formula (I) wherein
A represents

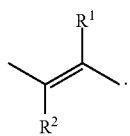

Compounds of formula (I) that are preferred include those in which the X-containing ring represents one of the following:

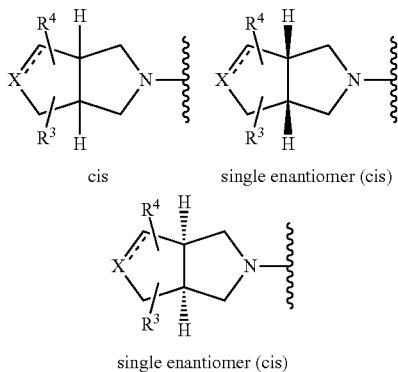

i.e. bicycles containing a cis-relationship at the ring junction (a trans-relationship would cause ring tension), which may be racemic or single enantiomers. As explained hereinafter, if for single enantiomers the absolute stereochemistry is/was not known, the chiral carbons at the ring junction may be depicted by bold or hashed lines (rather than as wedges).

More preferred compounds of formula (I) include those in which the fused bicyclic X-containing ring represents one of the following:

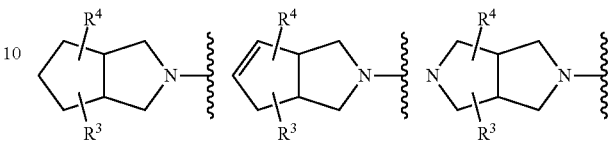

wherein in the above-mentioned fused bicycles, the compounds may be racemic or single enantiomers (if there is no relevant symmetry, and enantiomers are possible), as depicted hereinbefore.

In compounds of formula (I), it is preferred that:
(i) There is at least one $R^3$ or $R^4$ substituent present that does not represent hydrogen;
(ii) One of $R^3$ and $R^4$ (e.g. $R^3$) represent hydrogen, hydroxy or halo (e.g. fluoro) and the other one of $R^3$ and $R^4$ (e.g. $R^4$) represents a substituent other than hydrogen;
(iii) $R^3$ represents hydrogen, hydroxy or halo (e.g. fluoro) and most preferably represents hydrogen (i.e. $R^3$ is essentially not present);
(iv) $R^4$ represents a substituent other than hydrogen (i.e. there is an $R^4$ substituent that is present, and does not represent hydrogen);
(v) $R^4$ represents a substituent other than hydrogen, which is attached to X,
in which any of the above can be taken together or in combination. For instance, (iii), (iv) and/or (v) may be taken in combination to provide the particularly preferred compounds of formula (I) below:

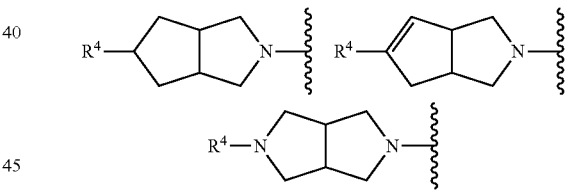

in which $R^4$ represents a substituent other than hydrogen. Particularly preferred substituents that $R^4$ (here and elsewhere) may represent include:
(i) optionally substituted aryl;
(ii) optionally substituted heteroaryl
(iii) $C_{1-6}$alkyl substituted by aryl or heteroaryl (which latter two aryl and heteroaryl groups are themselves optionally substituted as defined herein);
(iv) aryloxy (in which the aryl moiety is optionally substituted as defined herein);
(v) arylsulfonyl (in which the aryl moiety is optionally substituted as defined herein);
(vi) $C_{1-6}$alkyl, which is unsubstituted (e.g. ethyl, methyl, isopropyl);
(vii) di($C_{1-4}$alkyl)aminocarbonyl (e.g. —C(O)N(CH$_3$)$_2$);
(viii) aminocarbonyl (—C(O)NH$_2$);
(ix) $C_{1-4}$alkyloxycarbonyl (e.g. —C(O)O—CH$_2$CH$_3$);
(x) halo (e.g. fluoro);
(xi) $C_{2-6}$alkynyl (e.g. —C≡C);
(xii) $C_{1-6}$alkoxy (e.g. —OCH$_3$).

It is particularly preferred that the R⁴ group contains an aromatic moiety, and hence (i), (ii), (iii), (iv) and (v) above are particularly preferred).

In the case when R⁴ represents (i) above, then the aryl group is preferably phenyl, which group may be unsubstituted or substituted by one or two (e.g. one) substituent selected from $C_{1-4}$alkyloxy, halo, $C_{1-4}$alkyl or cyano (e.g. —OCH₃, chloro, fluoro, methyl or cyano).

In the case where R⁴ represents (ii) above, then the heteroaryl group is a monocyclic 5- or 6-membered ring containing one to four heteroatoms, for instance thienyl (e.g. 2- or 3-thienyl), pyridyl (e.g. 4-pyridyl or 3-pyridyl), pyrazolyl (e.g. 5-pyrazolyl, 4-pyrazolyl or 1-pyrazolyl), furanyl (e.g. 2- or 3-furanyl), thiazolyl (e.g. 2-thiazolyl), isoxazolyl (e.g. 4-isoxazolyl), pyrrolyl (e.g. 1-pyrrolyl), triazolyl (e.g. 1,2,3-triazol-1-yl, 1,2,3-triazol-2-yl or 1,2,4-triazol-2-yl), thiadiazolyl (e.g. 1,3,4-thiadiazol-2-yl), pyrimidinyl (e.g. 5-pyrimidinyl), tetrazolyl (e.g. 1,2,3,4-tetrazol-2-yl, 1,2,3,4-tetrazol-1-yl), imidazolyl (e.g. 2-imidazolyl). Such heteroaryl groups may be unsubstituted or substituted with one or two (e.g. two or, preferably, one) substituent(s) selected from halo, cyano, $C_{1-4}$alkyl (e.g. $C_{1-2}$alkyl), $C_{1-4}$alkyloxy (e.g. $C_{1-2}$alkyloxy) and $C_{1-4}$alkylcarbonyl (e.g. $C_{1-2}$alkylcarbonyl), e.g. —OCH₃, methyl, halo (e.g. chloro), cyano, and —C(O)—CH₃.

In the case where R⁴ represents (iii) above, then preferably the $C_{1-6}$alkyl group is methyl, i.e. —CH₃ substituted with aryl (e.g. phenyl, such as unsubstituted phenyl) or heteroaryl (e.g. a 5- or 6-membered monocyclic heteroaryl group containing one or two (e.g. one) heteroatom(s), so forming e.g. a thienyl group such as a 2-thienyl group; and such a heteroaryl group is preferably unsubstituted).

In the case where R⁴ represents (iv) or (v) above, aryl is preferably unsubstituted phenyl, and hence the R⁴ group is —O-phenyl or —S(O)₂-phenyl.

Most preferably, the R⁴ group represents (i) or (ii) above, i.e. aryl or heteroaryl. Even more preferably the R⁴ group represents (i) above, especially unsubstituted phenyl.

The most preferred compounds of formula (I) include those in which the X-containing fused bicyclic moiety represents:

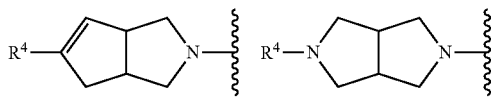

in which R⁴ is as defined herein. Such compounds which contain either a N(R⁴) moiety or a C(R⁴) moiety adjacent a double bond may be beneficial. This is because the shape of the nitrogen atom (e.g. being more planar in nature, as compared to a CR⁴ moiety that is not adjacent a double bond) or the presence of the double bond in the X-containing ring may help to orient the R⁴ group (if present) such that the compound overall (e.g. in view of the R⁴ substituent's orientation) displays better/improved binding properties to the FabI bacterial enzyme. Hence, these compounds of the invention may be advantageous in the sense that the presence of the double bond may lead to improved binding to/inhibition of the FabI enzyme. Consequently the compounds of the invention may be advantageous compounds (e.g. compared to known compounds) by virtue of these properties which may consequently lead to better potency, efficacy, etc.

Compounds of formula (I) can generally be prepared by reacting an intermediate of formula (II) with an intermediate of formula (III), in at least one reaction-inert solvent and optionally in the presence of at least one suitable coupling reagent and/or a suitable base, the said process further optionally comprising converting a compound of formula (I) into an addition salt thereof, and/or preparing stereochemically isomeric forms thereof.

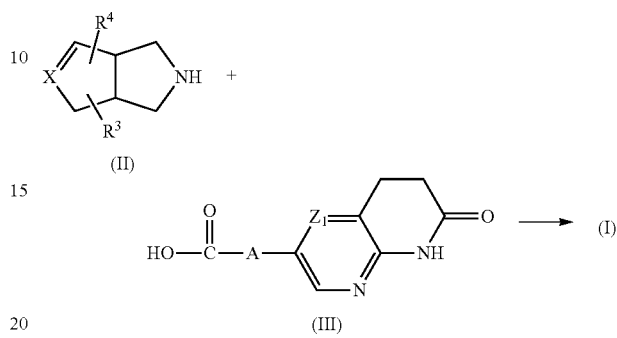

It may be convenient to activate the carboxylic acid of formula (III) by adding an effective amount of a reaction promoter. Non-limiting examples of such reaction promoters include carbonyldiimidazole, N,N'-dicyclohexyl-carbodiimide or 1-(3-dimethylaminopropyl)-3-ethylcarbodiimide, hydroxybenzotriazole, benzotriazolyl-oxytris (dimethylamino)-phosphonium hexafluorophosphate, tetrapyrrolidino-phosphonium hexafluorophosphate, bromotripyrrolidinophosphonium hexafluoro-phosphate, or a functional derivative thereof.

Compounds of formula (I) can also be prepared by reacting an intermediate of formula (II) with an intermediate of formula (IV), wherein Y represents hydroxy or halo. The reaction can be performed in a reaction-inert solvent such as, for example, dichloromethane or dimethylformamide and optionally in the presence of a suitable base such as, for example, diisopropylethyl-amine (DIPEA).

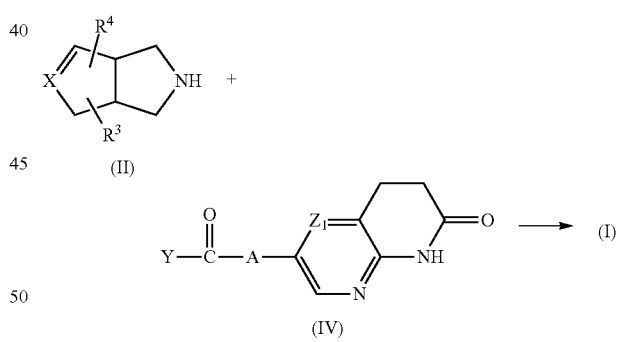

Compounds of formula (I) in which A represents —C(R²)=C(R¹)— can also be prepared by reacting an intermediate of formula (V) with an intermediate of formula (VI),

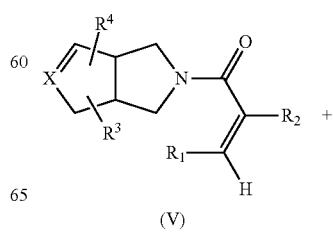

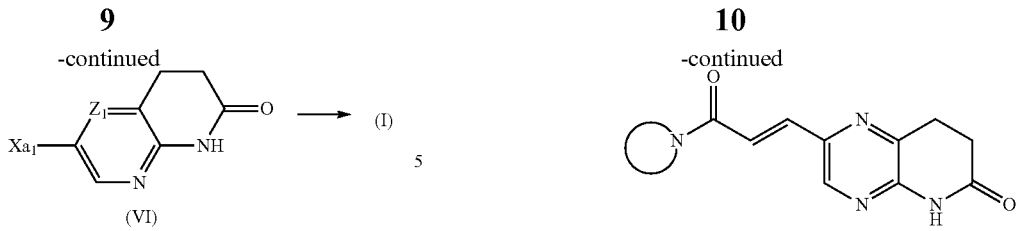

wherein $X_{a1}$ represents a suitable leaving group such as a suitable halo group (e.g. chloro, iodo and, especially, bromo) and the other integers are as hereinbefore defined, under reaction suitable reaction conditions, for example under metal catalyst coupling reaction conditions (e.g. precious metal coupling reaction conditions, wherein the precious metal is e.g. palladium-based), in particular under Heck reaction conditions using preferably a palladium-based catalyst such as palladium acetate, tetrakis(triphenylphosphione)palladium(0), bis(triphenylphosphine)palladium(II) dichloride, [1,1'-bis(diphenylphosphino)ferrocene]palladium(II) dichloride or the like (preferably, the catalyst is palladium acetate), for instance optionally in the presence of a suitable solvent (e.g. acetonitrile or the like), base (e.g. an amine base such as N,N-diisopropylamine or the like), and a ligand (e.g. triphenylphosphine, tri-O-tolylphosphine or the like). The reaction may be performed in a sealed tube and/or in a microwave.

The starting materials and some of the intermediates are known compounds and are commercially available or may be prepared according to conventional reaction procedures generally known in the art.

For the compounds in which $Z_1$ represents CH, intermediates (IV) and (VI) may be prepared as described herein, or according to conventional reaction procedures generally known in the art. For the corresponding intermediates in which $Z_1$ represents N, this may also be the case. However, such compounds may also be prepared in accordance with the following scheme:

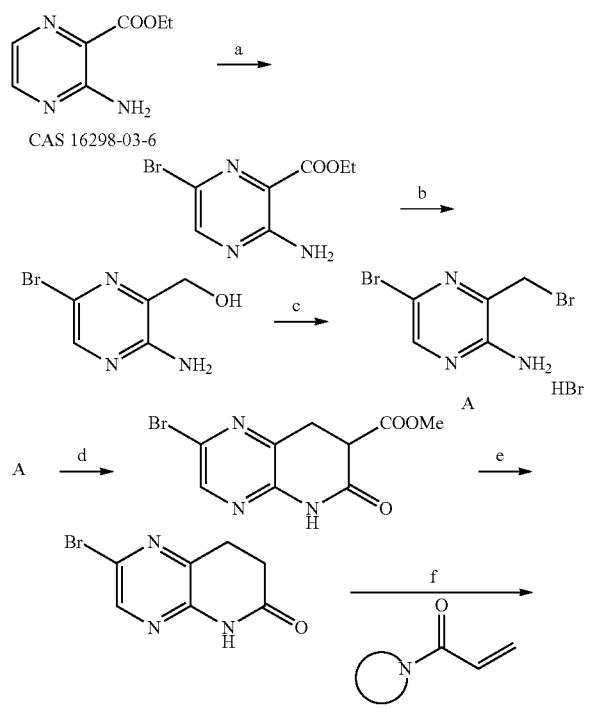

Conditions:
a) NBS, ACN, reflux, 3 h, 70%; b) LiAlH$_4$ 1M in THF, THF, 5° C. to RT, o.n., 20%; c) PBr$_3$, DCM, RT, o.n., 90%; f) dimethyl malonate, NaOMe in MeOH, MeOH, RT, o.n., 25%; g) NaOH, MeOH, reflux, 4 h, HCl, reflux, o.n.; h) DIEA, Pd(OAc)$_2$, tri-O-tolylphosphine, ACN, DMF, μw, 180° C., 25 min.

The compounds of formula (I) as prepared in the hereinabove described processes may be synthesized in the form of racemic mixtures of enantiomers which can be separated from one another following art-known resolution procedures. Those compounds of formula (I) that are obtained in racemic form may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

The compounds described herein are inhibitors of the FabI enzyme, as demonstrated by the examples below (including in Pharmacological Example 1). In view of these FabI enzyme inhibiting properties the compounds described herein are useful for treating bacterial infections. For instance, these compounds are useful for the treatment of bacterial infections, such as, for example, infections of upper respiratory tract (e.g. otitis media, bacterial tracheitis, acute epiglottitis, thyroiditis), lower respiratory (e.g. empyema, lung abscess), cardiac (e.g. infective endocarditis), gastrointestinal (e.g. secretory diarrhoea, splenic abscess, retroperitoneal abscess), CNS (e.g. cerebral abscess), eye (e.g. blepharitis, conjunctivitis, keratitis, endophthalmitis, preseptal and orbital cellulitis, darcryocystitis), kidney and urinary tract (e.g. epididymitis, intrarenal and perinephric abscess, toxic shock syndrome), skin (e.g. impetigo, folliculitis, cutaneous abscesses, cellulitis, wound infection, bacterial myositis), and bone and joint (e.g. septic arthritis, osteomyelitis). Additionally, the compounds may be useful in combination with known antibiotics.

Therefore the present invention also relates to compounds of formula (I) for use as a medicine especially for use in treating bacterial infections, in particular bacterial infections caused by a bacterium that expresses a FabI enzyme. Subsequently the present compounds may be used for the manufacture of a medicine for treatment of bacterial infections, in particular bacterial infections caused by a bacterium that expresses a FabI enzyme.

Further, the present invention provides a method of treating bacterial infections which comprises administering to a subject in need thereof a FabI enzyme inhibiting compound of formula (I).

A subject in need of treatment has a bacterial infection or has been exposed to an infectious bacterium, the symptoms of which may be alleviated by administering a therapeutically effective amount of the compounds of the present invention. For example, a subject in need of treatment can have an infection for which the compounds of formula (I) can be administered as a treatment. In another example, a subject in need of treatment can have an open wound or burn injury, for which the compounds of formula (I) can be administered as a prophylactic. Typically a subject will be treated for an existing bacterial infection.

A subject can have a bacterial infection caused by *Bacillus anthraces, Citrobacter* sp., *Escherichia coli, Francisella tularensis, Haemophilus influenza, Listeria monocytogenes, Moraxella catarrhalis, Mycobacterium tuberculosis, Neisseria meningitidis, Proteus mirabilis, Proteus vulgaris, Salmonella* sp., *Serratia* sp., *Shigella* sp., *Stenotrophomonas maltophilia, Staphylococcus aureus*, or *Staphylococcus epidermidis*. Preferably, the subject is treated (prophylactically or therapeutically) for a bacterial infection caused by a bacterium that expresses a FabI enzyme.

The term "treating" and "treatment", as used herein, refers to curative, palliative and prophylactic treatment, including reversing, alleviating, inhibiting the progress of, or preventing the disease, disorder or condition to which such term applies, or one or more symptoms of such disease, disorder or condition.

A "therapeutically effective amount" of a compound of the present invention is the quantity which, when administered to a subject in need of treatment, improves the prognosis of the subject, e.g. delays the onset of and/or reduces the severity of one or more of the subject's symptoms associated with a bacterial infection. The amount of the disclosed compound to be administered to a subject will depend on the particular disease, the mode of administration, and the characteristics of the subject, such as general health, other diseases, age, sex, genotype, body weight and tolerance to drugs. The skilled person will be able to determine appropriate dosages depending on these and other factors.

The compounds may be tested in one of several biological assays to determine the concentration of compound which is required to have a given pharmacological effect.

Additionally the present invention provides pharmaceutical compositions comprising at least one pharmaceutically acceptable carrier and a therapeutically effective amount of a compound of formula (I).

In order to prepare the pharmaceutical compositions of this invention, an effective amount of the particular compound, in base or acid addition salt form, as the active ingredient is combined in intimate admixture with at least one pharmaceutically acceptable carrier, which carrier may take a wide variety of forms depending on the form of preparation desired for administration. These pharmaceutical compositions are desirably in unitary dosage form suitable, preferably, for oral administration, rectal administration, percutaneous administration or parenteral injection.

For example in preparing the compositions in oral dosage form, any of the usual liquid pharmaceutical carriers may be employed, such as for instance water, glycols, oils, alcohols and the like in the case of oral liquid preparations such as suspensions, syrups, elixirs and solutions; or solid pharmaceutical carriers such as starches, sugars, kaolin, lubricants, binders, disintegrating agents and the like in the case of powders, pills, capsules and tablets. Because of their easy administration, tablets and capsules represent the most advantageous oral dosage unit form, in which case solid pharmaceutical carriers are obviously employed. For parenteral injection compositions, the pharmaceutical carrier will mainly comprise sterile water, although other ingredients may be included in order to improve solubility of the active ingredient. Injectable solutions may be prepared for instance by using a pharmaceutical carrier comprising a saline solution, a glucose solution or a mixture of both. Injectable suspensions may also be prepared by using appropriate liquid carriers, suspending agents and the like. In compositions suitable for percutaneous administration, the pharmaceutical carrier may optionally comprise a penetration enhancing agent and/or a suitable wetting agent, optionally combined with minor proportions of suitable additives which do not cause a significant deleterious effect to the skin. Said additives may be selected in order to facilitate administration of the active ingredient to the skin and/or be helpful for preparing the desired compositions. These topical compositions may be administered in various ways, e.g., as a transdermal patch, a spot-on or an ointment. Addition salts of the compounds of formula (I), due to their increased water solubility over the corresponding base form, are obviously more suitable in the preparation of aqueous compositions.

It is especially advantageous to formulate the pharmaceutical compositions of the invention in dosage unit form for ease of administration and uniformity of dosage. "Dosage unit form" as used herein refers to physically discrete units suitable as unitary dosages, each unit containing a predetermined amount of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

For oral administration, the pharmaceutical compositions of the present invention may take the form of solid dose forms, for example, tablets (both swallowable and chewable forms), capsules or gelcaps, prepared by conventional means with pharmaceutically acceptable excipients and carriers such as binding agents (e.g. pregelatinised maize starch, polyvinylpyrrolidone, hydroxypropylmethylcellulose and the like), fillers (e.g. lactose, microcrystalline cellulose, calcium phosphate and the like), lubricants (e.g. magnesium stearate, talc, silica and the like), disintegrating agents (e.g. potato starch, sodium starch glycollate and the like), wetting agents (e.g. sodium laurylsulphate) and the like. Such tablets may also be coated by methods well known in the art.

Liquid preparations for oral administration may take the form of e.g. solutions, syrups or suspensions, or they may be formulated as a dry product for admixture with water and/or another suitable liquid carrier before use. Such liquid preparations may be prepared by conventional means, optionally with other pharmaceutically acceptable additives such as suspending agents (e.g. sorbitol syrup, methylcellulose, hydroxypropylmethylcellulose or hydrogenated edible fats), emulsifying agents (e.g. lecithin or acacia), non-aqueous carriers (e.g. almond oil, oily esters or ethyl alcohol), sweeteners, flavours, masking agents and preservatives (e.g. methyl or propyl p-hydroxybenzoates or sorbic acid).

Pharmaceutically acceptable sweeteners useful in the pharmaceutical compositions of the invention comprise preferably at least one intense sweetener such as aspartame, acesulfame potassium, sodium cyclamate, alitame, a dihydrochalcone sweetener, monellin, stevioside sucralose (4,1', 6'-trichloro-4,1',6'-trideoxygalactosucrose) or, preferably, saccharin, sodium or calcium saccharin, and optionally at least one bulk sweetener such as sorbitol, mannitol, fructose, sucrose, maltose, isomalt, glucose, hydrogenated glucose syrup, xylitol, caramel or honey. Intense sweeteners are conveniently used in low concentrations. For example, in the case of sodium saccharin, the said concentration may range from about 0.04% to 0.1% (weight/volume) of the final formulation. The bulk sweetener can effectively be used in larger concentrations ranging from about 10% to about 35%, preferably from about 10% to 15% (weight/volume).

The pharmaceutically acceptable flavours which can mask the bitter tasting ingredients in the low-dosage formulations are preferably fruit flavours such as cherry, raspberry, black currant or strawberry flavour. A combination of two flavours may yield very good results. In the high-dosage formulations, stronger pharmaceutically acceptable flavours may be required such as Caramel Chocolate, Mint Cool, Fantasy and the like. Each flavour may be present in the final composition in a concentration ranging from about 0.05% to 1% (weight/volume). Combinations of said strong flavours are advantageously used. Preferably a flavour is used that does not undergo any change or loss of taste and/or color under the circumstances of the formulation.

The compounds of formula (I) may be formulated for parenteral administration by injection, conveniently intravenous, intra-muscular or subcutaneous injection, for example by bolus injection or continuous intravenous infusion. Formulations for injection may be presented in unit dosage form, e.g. in ampoules or multi-dose containers, including an added preservative. They may take such forms as suspensions, solutions or emulsions in oily or aqueous vehicles, and may contain formulating agents such as isotonizing, suspending, stabilizing and/or dispersing agents. Alternatively, the active ingredient may be present in powder form for mixing with a suitable vehicle, e.g. sterile pyrogen-free water, before use.

The compounds of formula (I) may also be formulated in rectal compositions such as suppositories or retention enemas, e.g. containing conventional suppository bases such as cocoa butter and/or other glycerides.

Those of skill in the treatment of antibacterial diseases linked to the inhibition of the FabI enzyme will easily determine the therapeutically effective amount of a compound of formula (I) from the test results presented hereinafter. In general it is contemplated that a therapeutically effective dose will be from about 0.001 mg/kg to about 50 mg/kg of body weight, more preferably from about 0.01 mg/kg to about 10 mg/kg of body weight of the patient to be treated. It may be appropriate to administer the therapeutically effective dose in the form of two or more sub-doses at appropriate intervals throughout the day. Said sub-doses may be formulated as unit dosage forms, for example each containing from about 0.1 mg to about 1000 mg, more particularly from about 1 to about 500 mg, of the active ingredient per unit dosage form.

The exact dosage and frequency of administration depends on the particular compound of formula (I) used, the particular condition being treated, the severity of the condition being treated, the age, weight and general physical condition of the particular patient as well as the other medication, the patient may be taking, as is well known to those skilled in the art. Furthermore, said "therapeutically effective amount" may be lowered or increased depending on the response of the treated patient and/or depending on the evaluation of the physician prescribing the compounds of the instant invention. The effective daily amount ranges mentioned hereinabove are therefore only guidelines.

Compounds of formula (I) may have the advantage that they may be more efficacious than, be less toxic than, be longer acting than, be more potent than, produce fewer side effects than, be more easily absorbed than, and/or have a better pharmacokinetic profile (e.g. higher oral bioavailability and/or lower clearance) than, and/or have other useful pharmacological, physical, or chemical properties over, compounds known in the prior art, whether for use in the above-stated indications or otherwise. The compounds may also exhibit such advantages in view of the presence of the $NR^4$ moiety or $CR^4$ moiety that is adjacent a double bond in the X-containing ring.

For instance, compounds of formula (I) may have the advantage that they have a good or an improved thermodynamic solubility (e.g. compared to compounds known in the prior art; and for instance as determined by a known method and/or a method described herein). Compounds of formula (I) may also have the advantage that they have a broad spectrum of activity against antibacterials (e.g. a broader spectrum of antibacterial activity compared to compounds known in the prior art; and for instance as determined by known tests and/or tests described herein). Compounds of formula (I) may also have the advantage that they have good or improved in vivo pharmacokinetics and oral bioavailability. They may also have the advantage that they have good or improved in vivo efficacy. For instance, the compounds of the invention may adaptable for intravenous formulation/dosing and hence may exhibit an improved in vivo efficacy when administered intravenously. The compounds may also exhibit such advantages in view of the presence of the $NR^4$ moiety or $CR^4$ moiety that is adjacent a double bond in the X-containing ring.

EXPERIMENTAL PART

Abbreviations

"DMF" is defined as N,N-dimethylformamide, "DCM" or "$CH_2Cl_2$" is defined as dichloromethane, "MeOH" is defined as methanol, "EtOH" is defined as ethanol, "$MgSO_4$" is defined as magnesium sulfate, and "THF" is defined as tetrahydrofuran, "AcOEt" or "EtOAc" is defined as ethyl acetate, "DIPEA" is defined as diisopropylethylamine, "EDCI" is defined as N'-(ethylcarbonimidoyl)-N,N-dimethyl-1,3-propane-diamine monohydrochloride, "HOBT" is defined as 1-hydroxy-1H-benzotriazole, "DIPA" is defined as diisopropylamine, "$K_2CO_3$" is defined as potassium carbonate, "TFA" is defined as trifluoroacetic acid, "$NH_4OH$" is defined as ammonium hydroxide, "$NaHCO_3$" is defined as carbonic acid monosodium salt, "$Et_2O$" is defined as diethyl ether, "$Na_2SO_4$" is defined as sulfuric acid disodium salt, "$CH_3CN$" is defined as acetonitrile, "NaOH" is defined as sodium hydroxide, "n-BuLi" is defined as n-Butyllithium, "i-PrOH" is defined as isopropanol, "$Pd(OAc)_2$" is defined as palladium acetate, "DMA" is defined as dimethylacetamide, "$Et_3N$" is defined as triethylamine.

Stereochemical Representation

The compounds of formula (I) have at least two asymmetric carbon atoms as illustrated below wherein the asymmetric carbon atoms are identified by a *:

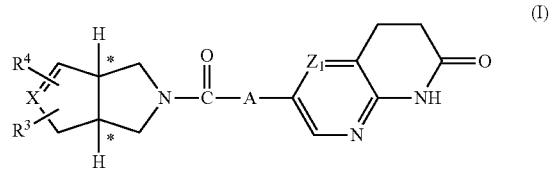

Due to ring tension in the system of two annulated five membered rings, only the 'cis' forms can be prepared and not the 'trans' forms.

Compounds of formula (I) wherein the system of two annulated five membered rings has the 'cis'-configuration

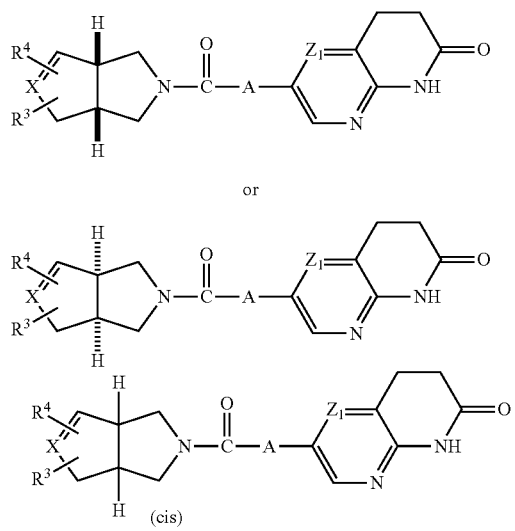

(cis)

Each of the above depicted "cis" compounds consists of a racemic mixture of two enantiomers and bold bonds or hashed bonds have been used to indicate this relative stereochemical configuration.

In case such a "cis" compound was separated into its two individual enantiomers, the stereochemical configuration of the single enantiomer was than designated as R* or S* indicating a relative stereochemistry. Accordingly a single enantiomer designated as (R*,S*) can either have the absolute (R,S) configuration or the (S,R) configuration. If the absolute stereochemistry of a specific chiral carbon atom in a single enantiomer was known the bold and hashed bonds were replaced by wedged bonds to indicate the compound is a single enantiomer having a known absolute stereochemistry.

A. Synthesis of the Intermediates

Example A.1 a) Preparation of intermediate (1)

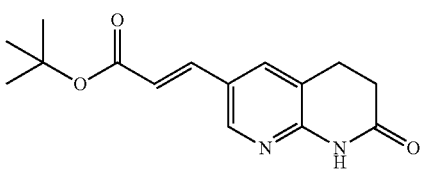

A solution of 6-bromo-3,4-dihydro-1H-[1,8]naphthyridin-2-one (1.0 g, 4.4 mmol), tert-butyl acrylate (2.56 ml, 17.62 mmol) and N,N-diisopropylethylamine (1.46 ml, 8.81 mmol) in acetonitrile (20 ml) and DMF (7 ml) was stirred and degassed with nitrogen gas for 10 minutes. Tri-o-tolylphosphine (0.27 g, 0.88 mmol) and palladium (II) acetate (47% on Pd) (0.099 g, 0.44 mol) were added and the resulting mixture was microwaved (1600 W, 180° C., 35 minutes). The reaction mixture was evaporated till dryness, taken up in a mixture of DCM/methanol (8/2) (50 ml), filtered through a short pad of celite and washed with DCM. The organic layer was washed with water, dried (MgSO$_4$), filtered and evaporated to dryness. The residue was taken up in cold ethanol (10 ml) and stirred at 5° C. for 5 minutes, the precipitate was filtered off, washed with cold ethanol (3 ml) and dried under vacuum to yield 950 mg intermediate (1).

b) Preparation of intermediate (2)

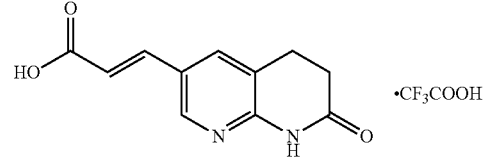

Intermediate (1) (4.1 g, 14.95 mmol) was dissolved in a mixture of trifluoroacetic acid (23.2 ml) in DCM (41 ml). The reaction was stirred at room temperature for 30 minutes. The reaction mixture was concentrated under reduced pressure. The resulting solid was triturated with diethyl ether, filtered off and dried under vacuum to yield 3.97 g of intermediate (2).

c) Preparation of intermediate (3)

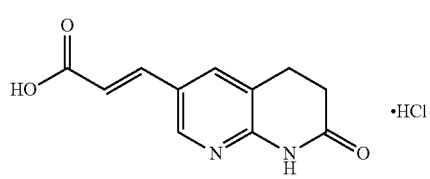

Intermediate (2) was triturated overnight in a mixture of HCl in dioxane (4 M, 48 ml), the solid was filtered off, washed with diethyl ether and dried under vacuum to give 3.7 g of intermediate (3).

Example A.2 a) Preparation of intermediate (4)

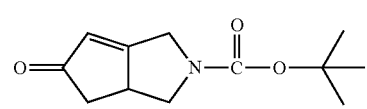

A solution of allyl-prop-2-ynyl-carbamic acid tert-butyl ester (CAS 147528-20-9, 45 g, 0.23 mol), cobalt carbonyl (17.5 g, 46.1 mmol) and 1,1,3,3-tetramethyl-2-thiourea (36.6 g, 0.277 mol) in toluene (1.8 L) was stirred and heated at 70° C. for 5 hours in an autoclave under CO pressure (2-3 bar). The resulting mixture was filtered through a short pad of celite and evaporated till dryness. The residue was taken up in DCM and filtered through a short pad of celite in order to obtain a clear solution. It was evaporated till dryness to give 85.7 g of crude residue. It was purified by preparative liquid chromatography on (silicagel 20-45 µm, 1000 g, mobile phase (gradient DCM/AcOEt from 95/5 to 80/20). Pure fractions were collected and the solvent was evaporated to give 36.5 g of intermediate (4).

b) Preparation of

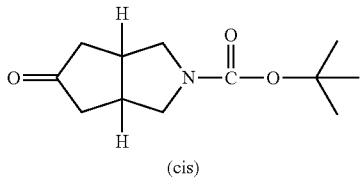

intermediate (5)

(cis)

A mixture of intermediate (4) (37.6 g, 0.168 mol) and palladium 10% on charcoal (7.5 g) in ethyl acetate (750 ml) was hydrogenated at room temperature for 30 minutes at 3 bars in a closed vessel reactor. The resulting mixture was filtered through a short pad of celite and evaporated till dryness to give 38.2 g of intermediate (5).

c) Preparation of

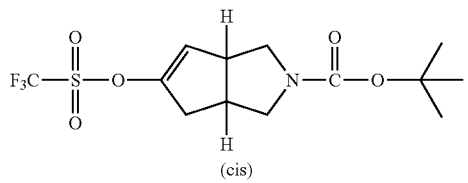

intermediate (6)

(cis)

n-BuLi 1.6M in hexane (64 ml, 0.102 mol) was added drop wise at −20° C., under a $N_2$ atmosphere, to a solution of diisopropylamine (14.3 ml, 0.102 mol) in dry THF (140 mL) then the mixture was stirred at −20° C. for 20 minutes. A solution of intermediate (5) (19.1 g, 84.8 mmol) in dry THF (190 mL) was then added at −78° C. and the resulting mixture was stirred for 1 hour at −78° C. A solution of N-phenyl-trifluoromethane sulfonimide (36.4 g, 0.102 mol) in dry THF (110 mL) was added at −78° C. then the mixture was allowed to reach room temperature and stirred overnight. The mixture was evaporated till dryness. The residue was taken in DCM, washed with an aqueous $NaHCO_3$ solution, dried ($MgSO_4$) and evaporated till dryness to give 27.7 g of intermediate (6).

d) Preparation of

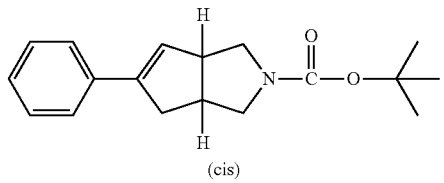

intermediate (7)

(cis)

A solution of intermediate (6) (9.3 g, 26.0 mmol) and phenyl boronic acid (3.81 g, 31.2 mmol) in a solution of potassium carbonate 2 M (26 ml) and ethylene glycol dimethyl ether (93 ml) was purged with $N_2$ for 10 minutes then tetrakistriphenyl-phosphine-palladium (3.0 g, 2.6 mmol) was added. The closed reactor was heated at 80° C. using one multimode cavity microwave CEM Mars system with a power output ranging from 0 to 400 W for 30 minutes. The resulting solution was cooled down to room temperature, water and EtOAc were added, the organic layer was separated, washed with water then brine, dried ($MgSO_4$) and evaporated till dryness. Purification of the residue was carried out by flash chromatography over silica gel (330 g, 15-40 µm, heptane/EtOAc from 100/0 to 80/20). The pure fractions were collected and evaporated to dryness to afford 4.3 g of intermediate (7).

e) Preparation of

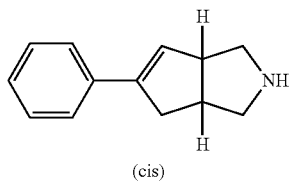

intermediate (8)

(cis)

Trifluoroacetic acid (44 ml) was added drop wise to a solution of intermediate (7) (14.5 g, 50.8 mmol) in $CH_2Cl_2$ (44 ml). The resulting solution was stirred at room temperature for 30 min then the mixture was cooled to 5° C. NaOH 3N was added slowly until the mixture was basic, it was extracted twice with $CH_2Cl_2$. The combined organic layer were washed with NaOH 3N then water, dried over $MgSO_4$ and evaporated to give 8.8 g of racemic compound of intermediate (8).

f) Preparation of

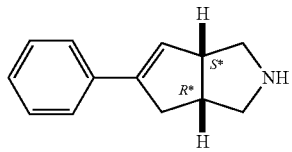

intermediate (9)

and

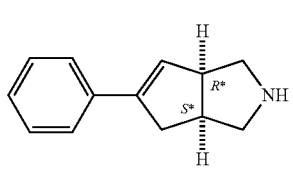

inetermediate (10)

Intermediate (8) was purified and resolved by chiral SFC on (CHIRALPAK AD-H 5 µm 250×20 mm). Mobile phase (0.3% isopropylamine, 73% CO$_2$, 27% iPrOH). Pure fractions were collected and the solvent was removed to give 3.9 g of intermediate (10) (R*,S*) ([α]$_D^{20}$=−53.19° (589 nm, c 0.3365 w/v %, DMF, 20° C.)) and 4 g of intermediate (9) (S*,R*) ([α]$_D^{20}$=+38.6° (589 nm, c 0.285 w/v %, DMF, 20° C.)).

Intermediate (9)

$^1$H NMR (400 MHz, DMSO-d$_6$) δ (ppm) 7.43 (d, J=7.6 Hz, 2H), 7.32 (t, J=7.6 Hz, 2H), 7.20-7.26 (m, 1H), 6.07 (d, J=2.0 Hz, 1H), 3.30-3.39 (m, 1H), 2.77-2.94 (m, 4H), 2.66 (dd, J=3.0, 11.1 Hz, 1H), 2.58 (dd, J=3.0, 11.1 Hz, 1H), 2.46 (d, J=15.7 Hz, 1H).

Intermediate (10)

$^1$H-NMR (400 MHz, DMSO-d$_6$) δ (ppm) 7.43 (d, J=7.6 Hz, 2H), 7.32 (t, J=7.6 Hz, 2H), 7.20-7.26 (m, 1H), 6.07 (d, J=2.0 Hz, 1H), 3.30-3.39 (m, 1H), 2.77-2.94 (m, 4H), 2.66 (dd, J=3.0, 11.1 Hz, 1H), 2.58 (dd, J=3.0, 11.1 Hz, 1H), 2.46 (d, J=15.7 Hz, 1H).

Example A.3 a) Preparation of

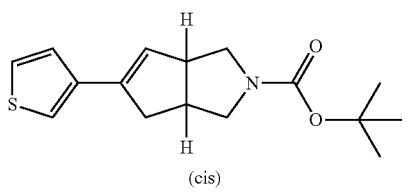

intermediate (11)

(cis)

A solution of intermediate (6) (44.4 g, 111.82 mmol) and 3-thiopheneboronic acid (17.17 g, 134.19 mmol) in potassium carbonate 2M (112 ml) and ethylene glycol dimethyl ether (444 ml), in an open vessel, was purged with N$_2$ for 10 minutes then tetrakistriphenylphosphinepalladium (12.92 g, 223.65 mmol) was added. The solution was heated at 78° C. using one multimode cavity microwave CEM MARS system with a power output ranging from 0 to 400 W for 1 hour. The solution was cooled to room temperature, water and EtOAc were added. The mixture was filtered through a pad of celite. The organic layer was separated, washed with water then brine, dried over MgSO$_4$ and evaporated till dryness. The residue was purified by preparative liquid chromatography on (silicagel 20-45 µm, 1000 g, mobile phase (80% heptane, 20% AcOEt)). The pure fractions were collected and concentrated to give 16 g of intermediate (11).

b) Preparation of

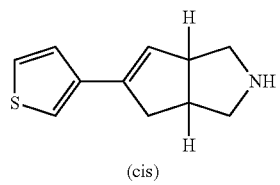

intermediate (12)

(cis)

Trifluoroacetic acid (14.37 ml, 186.47 mmol) was added to a solution of intermediate (11) (5.72 g, 18.65 mmol) in CH$_2$Cl$_2$ (57 ml). The reaction mixture was stirred at room temperature for 3 hours. K$_2$CO$_3$ (10% aqueous solution, 50 ml) and then K$_2$CO$_3$ solid were added at 0° C. to basify the solution. The organic layer was separated, washed with water, dried (MgSO$_4$) and evaporated till dryness. The residue was purified by preparative liquid chromatography on (silicagel 20-45 µm, 1000 g, mobile phase (1% NH$_4$OH, 93% DCM, 7% MeOH)). The pure fractions were collected and concentrated to give 12 g of intermediate (12).

c) Preparation of

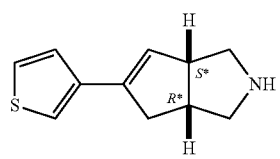

intermediate (13)

and intermediate (14)

Intermediate (12) was purified and resolved by chiral SFC on (CHIRALPAK AD-H 5 µm 250×20 mm). Mobile phase (0.3% isopropylamine, 80% CO$_2$, 20% methanol). Pure fractions were collected and the solvent was removed to give 5.8 g of intermediate (14) (R*,S*) ([α]$_D^{20}$=−12.4° (589 nm, c 0.5 w/v %, DCM, 20° C.)) and 5.6 g of intermediate (13) (S*,R*) ([α]$_D^{20}$=+9.43° (589 nm, c 0.35 w/v %, DCM, 20° C.)).

Intermediate (13)

$^1$H NMR (500 MHz, DMSO-d$_6$) δ (ppm) 7.49 (dd, J=2.5, 5.0 Hz, 1H), 7.31 (d, J=5.0 Hz, 1H), 7.29 (d, J=2.5 Hz, 1H), 5.88 (d, J=1.9 Hz, 1H), 3.28-3.33 (br.s., 1H), 2.75-2.87 (m, 4H), 2.61 (dd, J=2.8, 10.7 Hz, 1H), 2.54 (dd, J=3.3, 10.9 Hz, 1H), 2.40-2.15 (m, 2H).

Intermediate (14)

$^1$H NMR (500 MHz, DMSO-d$_6$) δ (ppm) 7.49 (dd, J=2.5, 5.0 Hz, 1H), 7.31 (d, J=5.0 Hz, 1H), 7.29 (d, J=2.5 Hz, 1H), 5.88 (d, J=1.9 Hz, 1H), 3.28-3.33 (br.s., 1H), 2.75-2.87 (m, 4H), 2.61 (dd, J=2.8, 10.7 Hz, 1H), 2.54 (dd, J=3.3, 10.9 Hz, 1H), 2.40-2.15 (m, 2H).

Example A.4 a) Preparation of

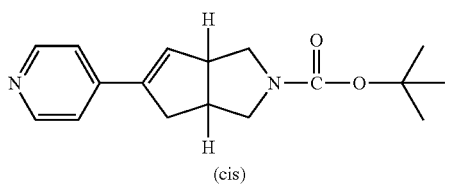
intermediate (15)
(cis)

A solution of intermediate (6) (108 g, 0.302 mol) and pyridine-4-boronic acid (49.5 g, 0.363 mol) in aqueous potassium carbonate 2M (302 ml, 0.604 mol) and ethylene glycol dimethyl ether (1.1 L) was purged with $N_2$ for 5 minutes then tetrakistriphenylphosphinepalladium (34.9 g, 0.030 mol) was added, the mixture was heated at 78° C. using a multimode microwave (CEM Mars 5) with a power output ranging from 0 to 800 W for 1 hour, cooled to room temperature, water and EtOAc were added, the organic layer was separated, washed with water then brine, dried over $MgSO_4$ and evaporated till dryness. The residue was purified by preparative liquid chromatography on (silicagel 15-40 μm, 300 g, mobile phase (0.1% $NH_4OH$, 97% DCM, 3% iPrOH). Pure fractions were collected and the solvent was removed to obtain 47.6 g of intermediate (15).

b) Preparation of

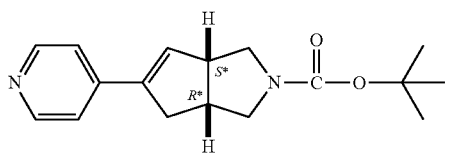
intermediate (17)

and

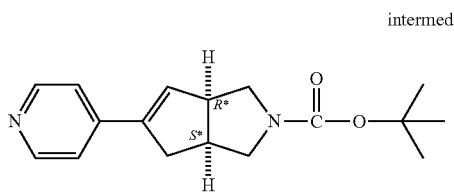
intermediate (18)

Intermediate (16) was purified and resolved by chromatography on Chiralpak AD (20 μm, 2000 g, 110 mm) with a flow rate of 750 ml/min. The mobile phase was methanol 100%. The pure fractions were collected and evaporated to dryness to give 18.7 g of intermediate (18) (R*,S*) (($[\alpha]_D^{20}$=+55.75° (589 nm, c 0.339 w/v %, DMF, 20° C.)) and 20.7 g of intermediate (17) (S*,R*) (($[\alpha]_D^{20}$=−68.38° (589 nm, c 0.253 w/v %, DMF, 20° C.)).

Intermediate (17)
$^1$H NMR (500 MHz, DMSO-$d_6$) δ (ppm) 8.52 (d, J=6.0 Hz, 2H), 7.41 (d, J=6.0 Hz, 2H), 6.50 (s, 1H), 3.36-3.61 (m, 4H), 2.81-3.02 (m, 3H), 2.61-2.53 (m, 1H), 1.36 (s, 9H)

Intermediate (18))
$^1$H NMR (500 MHz, DMSO-$d_6$) δ (ppm) 8.52 (d, J=6.0 Hz, 2H), 7.41 (d, J=6.0 Hz, 2H), 6.50 (s, 1H), 3.36-3.61 (m, 4H), 2.81-3.02 (m, 3H), 2.61-2.53 (m, 1H), 1.36 (s, 9H)

Example A.5

Preparation of

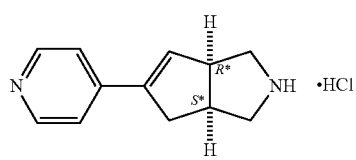
intermediate (19)

Intermediate (18) (24.8 g, 86.6 mmol) was added to HCl in dioxane (4 M, 108 ml) at 5° C. then the mixture was stirred at room temperature for 90 minutes. The precipitate was filtered off, washed with $Et_2O$ and dried under vacuum at 70° C. 21.1 g of intermediate (19).

Preparation of

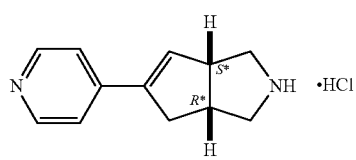
intermediate (20)

Intermediate (20) was prepared analogously starting from intermediate (17).

Example A.6 a) Preparation of

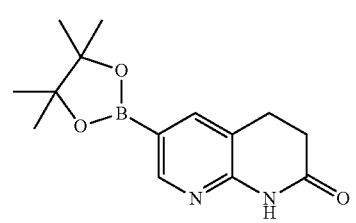
intermediate (21)

Reaction done on 4 batches of 0.5 g of 6-bromo-3,4-dihydro-1H-[1,8]naphthyridin-2-one each. A solution of 6-bromo-3,4-dihydro-1H-[1,8]naphthyridin-2-one (0.5 g, 2.20 mmol), bis(pinacolato)diboron (0.67 g, 2.64 mmol) and potassium acetate (0.648 g, 6.61 mmol) in DMF (5 ml) and CH₃CN (10 ml) was stirred and degassed with nitrogen for 10 minutes. 1,1'-Bis(diphenylphosphino)ferrocenedichloropalladium(II) (0.161 g, 0.22 mmol) was added and the resulting mixture was heated at 120° C. using a microwave (Biotage initiator 60) with a power output ranging from 0 to 400 W for 40 minutes. The mixture was evaporated till dryness, the residue was taken up in DCM and water, filtered through a short pad of celite. The organic layer of the filtrate was separated, washed with water, dried (MgSO₄) and evaporated till dryness. The residue was taken up in EtOH, filtered off and dried to give 0.36 g of intermediate (21).

b) Preparation of

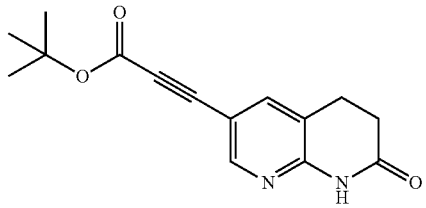

intermediate (22)

Intermediate (21) (1.0 g, 3.65 mmol), tert-butyl propiolate (0.426 ml, 3.04 mmol), silver(I)oxide (1.06 g, 4.56 mmol) and K₂CO₃ (0.84 g, 6.08 mmol) in CH₃CN (10 ml) and DMF (5 ml) was purged with N₂ then palladium(II)acetate (47% Pd) (0.034 g, 0.152 mmol) was added and the mixture heated at 100° C. using a monomode microwave (Biotage initiator 60) with a power output ranging from 0 to 400 W for 20 minutes. Water and EtOAc were added, the mixture was filtered through a short pad of celite, the organic layer was separated, washed with water then brine, dried (MgSO₄) and evaporated till dryness. The obtained residue was purified by flash chromatography over silica gel (15-40 μm, cartridge 30 g, from CH₂Cl₂ to CH₂Cl₂/CH₃OH/NH₄OH: 98.5/1.5/0.1) The pure fractions were collected and evaporated to dryness, yielding 0.037 g of intermediate (22).

c) Preparation of

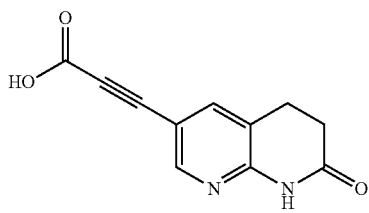

intermediate (23)

Intermediate (22) (0.053 g, 0.195 mmol) was dissolved in a solution of TFA/DCM (0.37 ml/0.5 ml). The reaction mixture was stirred at room temperature for 30 minutes. The reaction mixture was concentrated under reduced pressure. The resulting solid was triturated with Et₂O, filtered off and dried under vacuum (80° C.) to give 0.032 g of intermediate (23).

Example A.7 a) Preparation of

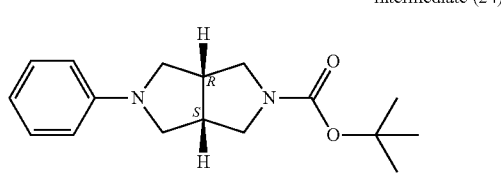

intermediate (24)

Microwave conditions: Biotage, 90° C., 25 minutes, low after 30 seconds of pre-stirring. A solution of bromobenzene (0.228 ml, 2.64 mmol), cis-2-tert-butyloxy-carbonyl-hexahydropyrrolo[3.4]pyrrole (0.6 g, 2.82 mmol) and sodium tert-butoxide (0.624 g, 6.5 mmol) in toluene (extra dry with molecular sieves) (15 ml) was stirred and degassed with nitrogen for 10 minutes. Tris(dibenzylideneacetone) dipalladium(0) (0.198 g, 0.216 mmol) and 2-(di-tert-butylphosphino)biphenyl (0.065 g, 0.216 mmol) were added and the resulting mixture was irradiated following the microwave conditions above. Water and EtOAc were added, the organic layer was separated and then dried (MgSO₄), filtered off and concentrated. The obtained residue was purified by flash chromatography over silica gel (15-40μ, 40 g, heptane/EtOAc 80/20). Pure fractions were collected and concentrated, yielding intermediate (24).

b) Preparation of

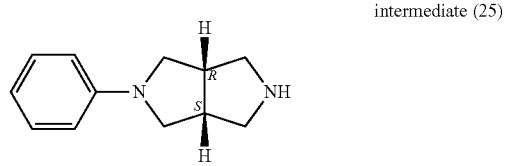

intermediate (25)

TFA (4.54 ml, 58.95 mmol) was added to a solution of intermediate (24) (1.7 g, 5.9 mmol) in DCM (15 ml). The reaction mixture was stirred at room temperature for 2 hours, water and DCM were added, K₂CO₃ (10% aqueous solution) was added to basify and the organic layer was separated, washed with water, dried (MgSO₄) and evaporated till dryness yielding intermediate (25) as an oil.

The following compounds were made using the same procedure as Example A.7 whereby bromobenzene was replaced by 2-bromothiophene, 2-bromoanisole, 2-bromo-1-methylbenzene, 2-bromo-1-chlorobenzene, 3-bromopyridine, 2-bromothiazole, 4-bromo-1-chlorobenzene, or 3-bromo-1-chlorobenzene respectively.

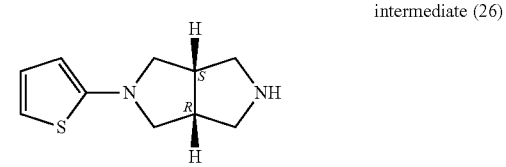

intermediate (26)

-continued intermediate (27)
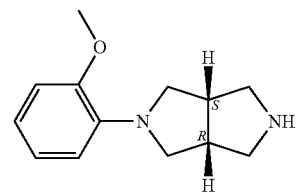

intermediate (28)
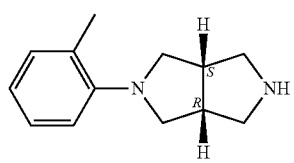

intermediate (29)
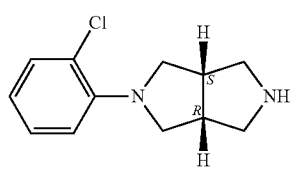

intermediate (30)
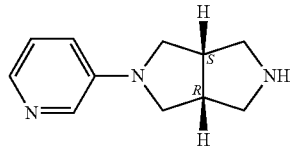

intermediate (31)
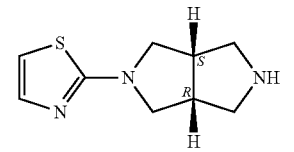

intermediate (32)
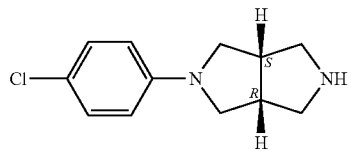

intermediate (33)
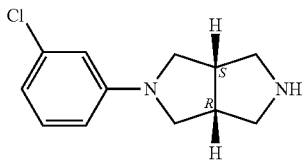

Example A.8 a) Preparation of intermediate (34)
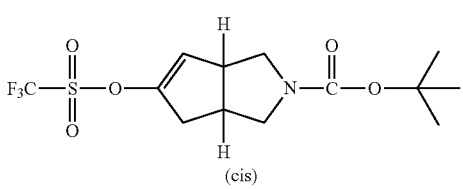
(cis)

Reaction under $N_2$. n-BuLi (1.6M in hexane) (3.33 ml, 5.33 mmol) was added dropwise at −20° C. to a solution of DIPA (0.749 ml, 5.33 mmol) in THF (8 ml) then the mixture was stirred at −20° C. for 20 minutes. A solution of intermediate (4) (1.0 g, 4.44 mmol) in THF (10 ml) was then added at −78° C. and the resulting mixture was stirred for 30 minutes at −78° C. A solution of N-phenyltrifluoro-methanesulfonimide (1.74 g, 4.88 mmol) in THF (6 ml) was added at −78° C. then the mixture was allowed to reach room temperature and was stirred overnight. The mixture was concentrated and the residue was purified by flash chromatography over silica gel (40 g, 15-40 μm, heptane/EtOAc 70/30) The pure fractions were collected and evaporated to dryness, yielding intermediate (34).

b) Preparation of intermediate (35)
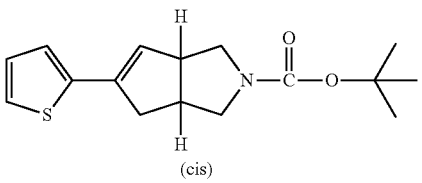
(cis)

Reaction under nitrogen. Microwave conditions: Biotage initiator 60, 80° C., 20 minutes. A solution of intermediate (34) (0.42 g, 0.881 mmol) and thiophene-2-boronic acid (0.135 g, 1.06 mmol) in $K_2CO_3$ (2 M, 0.88 ml) and ethylene glycol dimethyl ether (4 ml) was purged with $N_2$ for 10 minutes then tetrakis(triphenyl-phosphine)palladium(0) (0.102 g, 0.088 mmol) was added. The mixture was irradiated following the microwave conditions above, cooled to room temperature, water and EtOAc were added, the organic layer was separated, washed with water then brine, dried ($MgSO_4$) and evaporated till dryness. The residue was purified by flash chromatography over silica gel (10 g, 15-40 μm, heptane 100 to heptane/EtOAc 80/20). The pure fractions were collected and evaporated to dryness, yielding intermediate (35).

c) Preparation of intermediate (36)
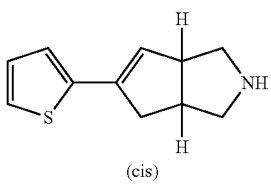
(cis)

A mixture of intermediate (35) (0.226 g, 0.776 mmol) in TFA (0.7 ml) and DCM (4 ml) was stirred at room temperature for 1 hour then the reaction mixture was poured out into $K_2CO_3$ (10% aqueous solution) and extracted with DCM. The organic layer was separated, washed with water, dried ($MgSO_4$) and evaporated till dryness, yielding intermediate (36).

The following compounds were made using the same procedure as Example A.8b/A.8c whereby thiophene-2- boronic acid was replaced by 2-methoxyphenyl-boronic acid, or formic acid respectively.

intermediate (42)

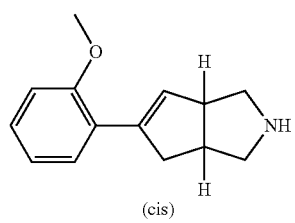
(cis)

intermediate (43)

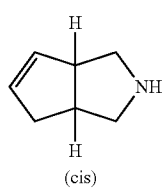
(cis)

Example A.9 a) Preparation of intermediate (37)

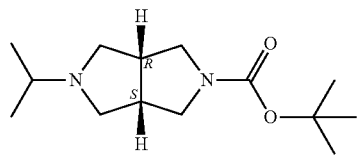

Microwave conditions: Biotage, 120° C., 30 minutes. A mixture of cis-2-tert-butyloxycarbonyl-hexahydropyrrolo[3.4]pyrrole (0.027 g, 0.13 mmol), 2-bromopropane (0.018 mL, 0.19 mmol) and triethylamine (0.088 ml, 0.64 mol) in DMF (0.2 ml) was irradiated following the conditions above. Water and EtOAc were added, the organic layer was separated, the aqueous layer was extracted twice with EtOAc, the combined organic phase were washed with water and brine, dried (MgSO₄) and evaporated till dryness, yielding intermediate (37).

b) Preparation of intermediate (38)

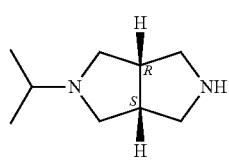

TFA (0.62 ml, 8.02 mmol) was added to a solution of intermediate (37) (0.204 g, 0.8 mmol) in DCM (2 ml). The reaction mixture was stirred at room temperature for 3 hours, water and DCM were added, K₂CO₃ 10% was added to basify, NaCl solid was added to saturate, and the organic layer was separated, washed with water, dried (MgSO₄) and evaporated till dryness yielding intermediate (38) as an oil.

The following compounds were made using the same procedure as Example A.9 whereby 2-bromopropane was replaced by propargyl bromide, benzenesulfonyl chloride, or 2-thienylmethyl methanesulfonate respectively.

intermediate (39)

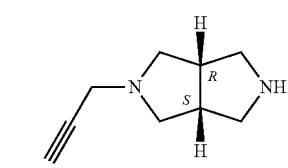

intermediate (40)

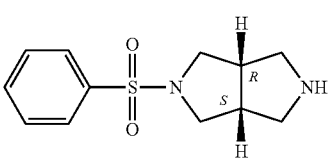

intermediate (41)

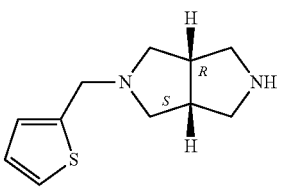

Example A.10 a) Preparation of intermediate (44)

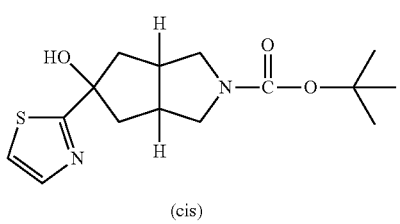
(cis)

Reaction under N₂. BuLi (1.6M in hexane) (4.8 ml, 7.70 mmol) was added dropwise at −78° C. to a solution of thiazole (0.5 ml, 7.05 mmol) in Et₂O (5 ml) then the mixture was stirred for 30 minutes. A solution of intermediate (5) (1.44 g, 6.41 mmol) in Et₂O (7 ml) was added then the mixture stirred and allowed to reach room temperature for 2 hours.

Water and EtOAc were added, the organic layer was separated, washed with water then brine, dried (MgSO₄) and evaporated till dryness. The obtained residue was purified by flash chromatography over silica gel (50 g, 15-40 μm, heptane/EtOAc 80/20 to heptane/EtOAc 50/50). The pure fractions were collected and evaporated to dryness, yielding intermediate (44).

b) Preparation of

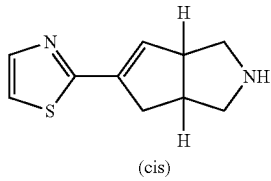

intermediate (45)

(cis)

A mixture of intermediate (44) (1.05 g, 3.38 mmol) in HCl (37% in H₂O) (7 ml) in a sealed tube was heated at 140° C. using a single mode microwave (Biotage Initiator EXP 60) with a power output ranging from 0 to 400 W for 1 hour. The reaction mixture was poured into K₂CO₃ (10% aqueous solution), the organic layer was separated, dried (MgSO₄) and evaporated till dryness, yielding 0.23 g of residue (1). The aqueous layer was evaporated till dryness, the solid was suspended in DCM and stirred for 10 minutes. The suspension was filtered and the filtrate was evaporated till dryness, yielding 0.29 g of residue (2). Residues (1) and (2) were combined for purification, it was carried out by flash chromatography over silica gel (15-40 µm, 30 g, from CH₂Cl₂ to CH₂Cl₂/CH₃OH/NH₄OH: 90/10/1). The pure fractions were collected and evaporated to dryness, yielding 0.42 g of intermediate (45).

Example A.11 a) Preparation of

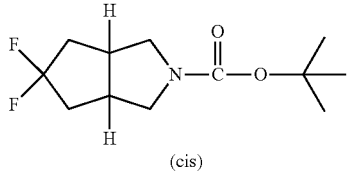

intermediate (46)

(cis)

Diethylaminosulfur trifluoride (1.24 ml, 10.12 mmol) was added dropwise to a solution of intermediate (5) (0.570 g, 2.53 mmol) in DCM (6 ml) cooled in a ice bath at 5° C., the mixture was stirred 1 hour at 5° C. and then overnight at room temperature. The mixture was cooled down at 0° C. and NaHCO₃ saturated was added. The organic layer was extracted with CH₂Cl₂, dried (MgSO₄), filtered and concentrated affording intermediate (46).

b) Preparation of

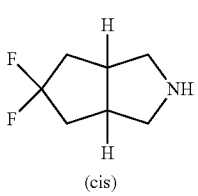

intermediate (47)

(cis)

TFA (0.39 ml, 5.12 mmol) was added to a solution of intermediate (46) (0.146 g, 0.51 mmol) in DCM (1.5 ml). The reaction mixture was stirred at room temperature for 3 hours, water and DCM were added, K₂CO₃ (10% aqueous solution) was added to basify and the organic layer was separated, washed with water, dried (MgSO₄) and evaporated till dryness yielding intermediate (47) as an oil.

Example A.12 a) Preparation of

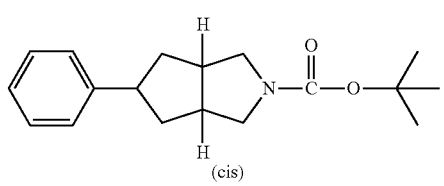

intermediate (48)

(cis)

A mixture of intermediate (7) (0.3 g, 1.05 mmol) and Pd/C 10% dry (0.06 g) in MeOH (15 ml) was hydrogenated at room temperature and atmospheric pressure for 2 hours. The reaction mixture was filtered through a short pad of celite, washed with DCM and the filtrate was evaporated till dryness, yielding intermediate (48).

b) Preparation of

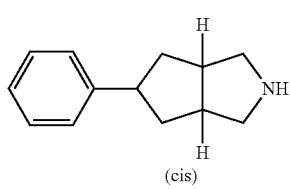

intermediate (49)

(cis)

A mixture of intermediate (48) (0.286 g, 0.995 mmol) and TFA (0.9 ml) in DCM (6 ml) was stirred at room temperature for 30 minutes then the reaction mixture was poured out into K₂CO₃ (10% aqueous solution) and extracted with DCM. The organic layer was separated, washed with water, dried (MgSO₄) and evaporated till dryness, yielding intermediate (49).

Example A.13 a) Preparation of

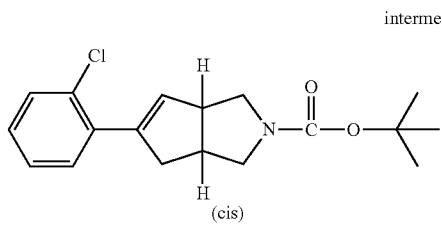

intermediate (50)

(cis)

Reaction under N₂. Microwave conditions: Biotage initiator 60, 80° C., 20 minutes. A solution of intermediate (38) (0.45 g, 1.26 mmol) and 2-chlorophenylboronic acid (0.236 g, 1.51 mmol) in $K_2CO_3$ (2 M, 1.26 ml) and ethylene glycol dimethyl ether (5 ml) was purged with $N_2$ for 10 minutes then tetrakis(triphenylphosphine)palladium(0) (0.146 g, 0.126 mmol) was added. The mixture was irradiated following the conditions above, cooled to room temperature, water and DCM were added, the organic layer was separated, washed with water, dried (MgSO₄) and evaporated till dryness. The residue was purified by preparative liquid chromatography on (silicagel 5 µm, 150×30.0 mm). Mobile phase (100% DCM). The desired fractions were collected and the solvent was evaporated, yielding of intermediate (50).

b) Preparation of intermediate (51)

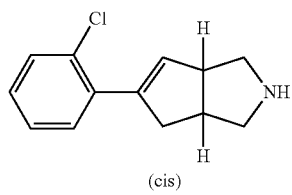
(cis)

A mixture of intermediate (50) (0.3 g, 0.938 mmol) and TFA (0.9 ml) in DCM (6 ml) was stirred at room temperature for 30 minutes then the reaction mixture was poured out into $K_2CO_3$ (10% aqueous solution) and extracted with DCM. The organic layer was separated, washed with water, dried (MgSO₄) and evaporated till dryness, yielding intermediate (51).

The following compounds were made using the same procedure as Example A.13 whereby 2-chlorophenylboronic acid was replaced by 2-methylphenylboronic acid, 1-methyl-1H-pyrazole-5-boronic pinacol ester, furan-2-boronic acid, 2-fluorophenyl-boronic acid, furan-3-boronic acid, 2-cyanophenylboronic acid, 5-dimethylisoxazole-4-boronic acid, pyridine-3-boronic acid, 1-methyl-4-(4,4,5,5-tetramethyl-1,3,2-dioxaborolan-2-yl)-1H-pyrazole, benzylzinc bromide, 2-chloropyridine-3-boronic acid, pyrimidyl-5-boronic acid pinacolate, 1-boc-pyrazole-4-boronic acid pinacol ester, 5-methylfuran-2-boronic acid, or 4-methoxy-3-pyridinylboronic acid respectively.

intermediate (52)

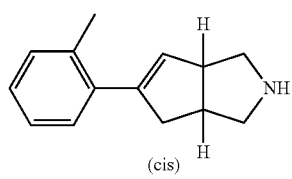
(cis)

intermediate (53)

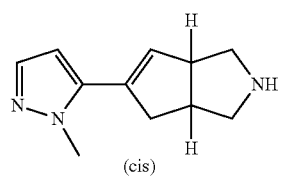
(cis)

intermediate (54)

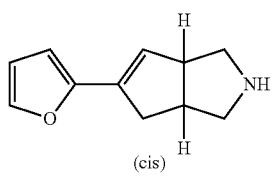
(cis)

intermediate (55)

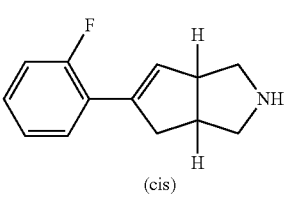
(cis)

intermediate (56)

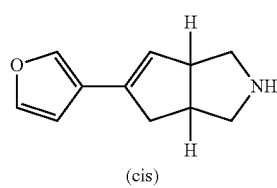
(cis)

intermediate (57)

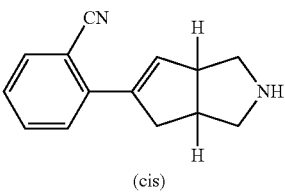
(cis)

intermediate (58)

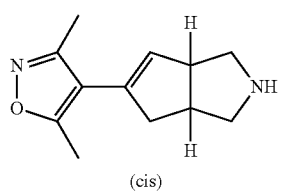
(cis)

intermediate (59)

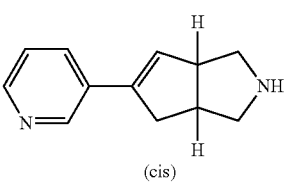
(cis)

intermediate (60)

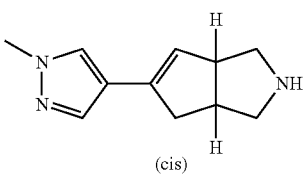
(cis)

intermediate (61)

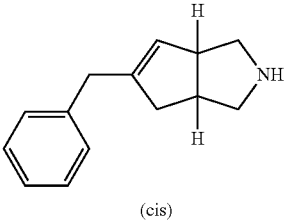
(cis)

-continued intermediate (62)

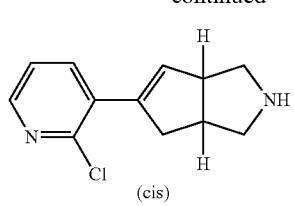
(cis)

intermediate (63)

(cis)

intermediate (64)

(cis)

intermediate (65)

(cis)

intermediate (66)

(cis)

Example A.14 a) Preparation of intermediate (67)

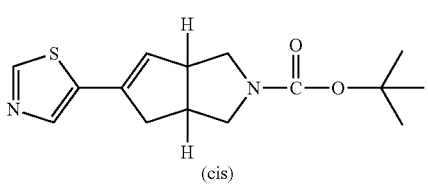
(cis)

Intermediate (34) (2.798 mmol), palladium(II)acetate (47% Pd) (0.14 mmol), K₂CO₃ (4.198 mmol), trimethylacetic acid (0.84 mmol) and tricyclohexylphosphonium tetrafluoroborate (0.196 mmol) were purged with N₂ in a sealed tube. Thiazole (4.198 mmol) and DMA (10 ml) were added and the reaction mixture was heated at 100° C. overnight. Water and EtOAc were added, the organic layer was separated, washed with water and brine, dried (MgSO₄) and evaporated till dryness. The obtained residue was purified by flash chromatography over silica gel (cartridge 30 g, 15-40 μm, heptane/EtOAc 80/20 to heptane/EtOAc 60/40) The pure fractions were collected and evaporated to dryness, yielding intermediate (67).

b) Preparation of intermediate (68)

(cis)

A solution of intermediate (67) (0.24 g, 0.821 mmol) in TFA (0.8 ml) and DCM (5 ml) was stirred at room temperature for 30 minutes then the reaction mixture was poured out into K₂CO₃ (10% aqueous solution) and extracted with DCM. The organic layer was separated, washed with water, dried (MgSO₄) and evaporated till dryness, yielding 0.1 g of intermediate (68).

Example A.15 a) Preparation of intermediate (69)

(cis)

Pd(OAc)₂ (1.3 mg, 0.0056 mmol) was added to a solution of intermediate (34) (0.1 g, 0.28 mmol), 1,3-bis(diphenylphosphino)propane (4.6 mg, 0.011 mmol) and potassium acetate (0.041 g, 0.42 mmol) in EtOH (0.25 ml) and THF (2 ml) under nitrogen atmosphere. The mixture was stirred under 5 bars of carbon monoxyde at 100° C. for 18 hours in a stainless steel autoclave, yielding intermediate (69).

b) Preparation of intermediate (70)

(cis)

A solution of intermediate (69) (0.2 g, 0.711 mmol) in HCl (4M in dioxane) (2 ml) was stirred at room temperature for 30 minutes then it was evaporated till dryness, yielding 0.13 g of intermediate (70).

Example A.16 a) Preparation of intermediate (71)

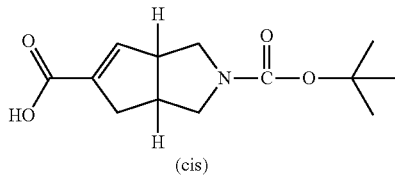

(cis)

Pd(OAc)$_2$ (25 mg, 0.112 mmol) was added to a solution of intermediate (34) (2.0 g, 5.6 mmol), 1,3-bis(diphenylphosphino)propane (92 mg, 0.22 mmol) and potassium acetate (0.82 g, 8.4 mmol) in EtOH (5 ml) and THF (40 ml) under nitrogen atmosphere then the mixture was stirred under 5 bars of carbon monoxyde at 100° C. for 18 hours in a stainless steel autoclave. The reaction mixture was poured into water and EtOAc, the organic layer was washed with water then brine, dried (MgSO$_4$), filtered and evaporated till dryness. The obtained residue was purified by flash chromatography over silica gel (15-40 µm, 40 g, Heptane/EtOAc 90/10 to Heptane/EtOAc 70/30). The pure fractions were collected and evaporated to dryness, yielding 0.61 g of intermediate (71).

b) Preparation of intermediate (72)

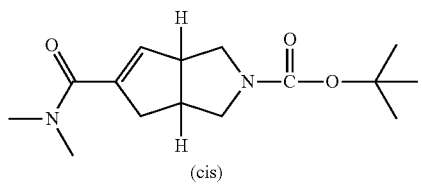

(cis)

A mixture of intermediate (71) (0.3 g, 1.18 mmol), dimethylamine in THF (2 M, 1.18 ml, 2.37 mmol), EDCI (0.27 g, 1.42 mmol), HOBt (0.19 g, 6.21 mmol) and triethylamine (0.25 ml, 1.78 mmol) in DCM (3 ml) and THF (3 ml) was stirred overnight at room temperature. Water and DCM were added, the organic layer was separated, dried (MgSO$_4$) and evaporated till dryness, yielding 0.37 g of intermediate (72).

c) Preparation of intermediate (73)

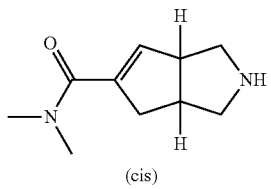

(cis)

A solution of intermediate (72) (0.37 g, 1.32 mmol) in HCl (4M in dioxane) (4 ml) was stirred at room temperature for 30 minutes then the reaction mixture was poured out into K$_2$CO$_3$ (10% aqueous solution) and extracted with DCM. The organic layer was separated, washed with water, dried (MgSO$_4$) and evaporated till dryness, yielding intermediate (73).

Example A.17 a) Preparation of intermediate (74)

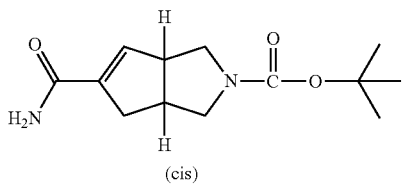

(cis)

A mixture of intermediate (71) (0.3 g, 1.18 mmol), 1,1,1,3,3,3-hexamethyldisilazane (0.23 g, 1.42 mmol), EDCI (0.27 g, 1.42 mmol), HOBt (0.19 g, 6.21 mmol) and triethylamine (0.25 ml, 1.78 mmol) in DCM (3 ml) and THF (3 ml) was stirred overnight at room temperature. Water and DCM were added, the organic layer was separated, dried (MgSO$_4$) and evaporated till dryness. The obtained residue was purified by flash chromatography over silica gel (15-40 µm, 10 g, from CH$_2$Cl2 to CH$_2$Cl$_2$/CH$_3$OH/NH$_4$OH: 94/6/0.1) The pure fractions were collected and evaporated to dryness, yielding 0.16 g of intermediate (74).

b) Preparation of intermediate (75)

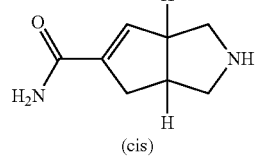

(cis)

A solution of intermediate (74) (0.16 g, 0.634 mmol) in HCl (4M in dioxane) (2 ml) was stirred at room temperature for 30 minutes then it was evaporated till dryness, yielding 0.1 g of intermediate (75).

Example A.18 a) Preparation of intermediate (76)

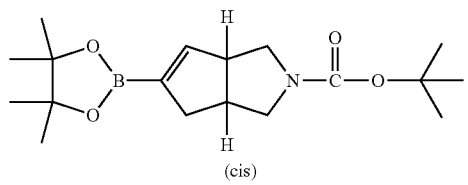

(cis)

A solution of intermediate (34) (0.2 g, 0.56 mmol), bis(pinacolato)diboron (0.171 g, 0.67 mmol) and potassium acetate (0.165 g, 1.68 mmol) in 1,4-dioxane (2 ml) was stirred and degassed with $N_2$ for 10 minutes. 1,1'-bis(diphenylphosphino)ferrocene-dichloropalladium(II) (0.041 g, 0.056 mmol) was added and the reaction mixture was heated at 100° C. using a single mode microwave (Biotage Initiator EXP 60) with a power output ranging from 0 to 400 W for 20 minutes. Water and EtOAc were added, the organic layer was separated, washed with water then brine, dried ($MgSO_4$) and evaporated till dryness. The obtained residue was purified by flash chromatography over silica gel (10 g, 15-40 μm, heptane/EtOAc 85/15 to heptane/EtOAc 70/30). The pure fractions were collected and evaporated to dryness, yielding intermediate (76).

b) Preparation of intermediate (77)

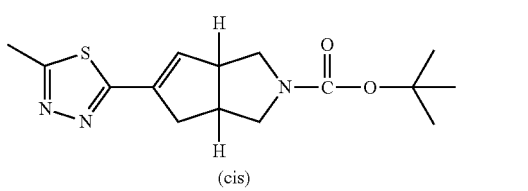
(cis)

A solution of intermediate (76) (0.45 g, 1.34 mmol) and 2-bromo-5-methyl-1,3,4-thiadiazole (0.288 g, 1.61 mmol) in $K_2CO_3$ (2 M, 1.34 mL, 2.69 mmol) and ethylene glycol dimethyl ether (5 ml) was stirred and degassed with $N_2$ for 10 minutes. Tetrakis(triphenylphosphine)palladium(0) (0.155 g, 0.134 mmol) was added and the reaction mixture was heated at 150° C. using a single mode microwave (Biotage Initiator EXP 60) with a power output ranging from 0 to 400 W for 5 minutes. Water and EtOAc were added, the organic layer was separated, washed with brine, dried ($MgSO_4$) and evaporated till dryness. The obtained residue was purified by flash chromatography over silica gel (cartridge 30 g, 15-40 μm, DCM to DCM/MeOH/$NH_4OH$: 98/2/0.1) The pure fractions were collected and evaporated to dryness, yielding intermediate (77).

c) Preparation of intermediate (78)

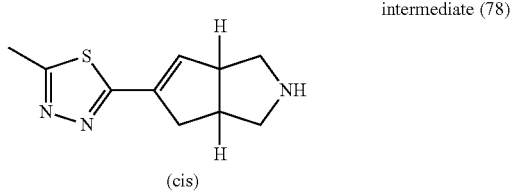
(cis)

A solution of intermediate (77) (0.14 g, 0.455 mmol) in HCl (4M in dioxane) (2 ml) was stirred at room temperature for 30 minutes then the reaction mixture was poured out into $K_2CO_3$ 10% aqueous and extracted with DCM. The organic layer was separated, washed with water, dried ($MgSO_4$) and evaporated till dryness, yielding 81 mg of intermediate (78).

Example A.19 a) Preparation of intermediate (79)

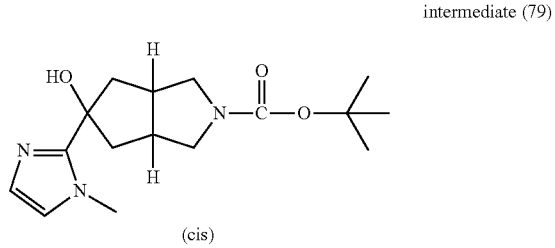 [SMILES: Cn1ccnc1C1(O)CC2CN(C(=O)OC(C)(C)C)CC2C1]
(cis)

BuLi (1.6M in hexane) (4.2 ml, 6.66 mmol) was added dropwise to a solution of 1-methylimidazole (0.53 ml, 6.66 mmol) in THF (5 ml) under nitrogen at −78° C. then the resulting mixture was stirred for 1 hour at 0° C. The reaction mixture was cooled down to −78° C., a solution of intermediate (5) (1.0 g, 4.44 mmol) in THF (10 ml) was added. The mixture was stirred at −78° C. for 2 hours then allowed to reach room temperature and stirred overnight. Water and EtOAc were added, the organic layer was separated, washed with water and brine, dried ($MgSO_4$) and evaporated till dryness. The obtained residue was purified by flash chromatography over silica gel (15-40 μm, 30 g, from $CH_2Cl_2$ to $CH_2Cl_2$/$CH_3OH$/$NH_4OH$: 95/5/0.1). The pure fractions were collected and evaporated to dryness, yielding 0.54 g of intermediate (79).

b) Preparation of intermediate (80)

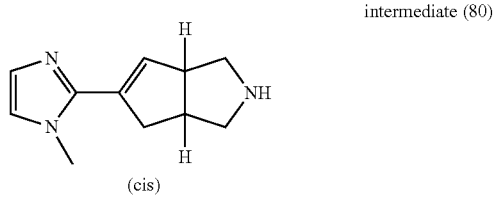
(cis)

A mixture of intermediate (79) (0.54 g, 1.76 mmol) in HCl (37% in $H_2O$) (5 ml) in a sealed tube was heated at 140° C. using a single mode microwave (Biotage Initiator EXP 60) with a power output ranging from 0 to 400 W for 1 hour. The reaction mixture was evaporated till dryness, yielding 0.47 g of intermediate (80).

Example A.20 a) Preparation of intermediate (81)

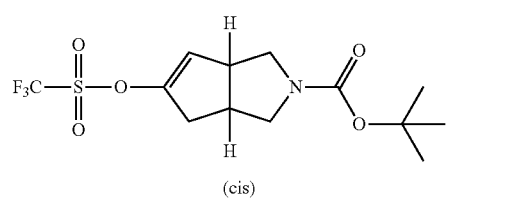
(cis)

The reaction was performed in anhydrous conditions under argon atmosphere and monitored by TLC (silica gel, petroleum ether/ethyl acetate 1/1, UV/PMA). n-Butyllithium, 2.5M in hexanes (4.28 ml, 10.7 mmol) was added dropwise (5 min) to a solution of diisopropylamine (1.51 ml, 10.7 mmol) in THF (16 ml) at −20° C. The mixture was stirred for 15 minutes at −20° C. and then cooled to −78° C. A solution of intermediate (95) (2.00 g, 8.88 mmol) in THF (20 ml) was added (5 min) at −78° C. The mixture was stirred at −78° C. for 2 hours. A solution of 2-[N,N-bis(trifluoromethyl-sulfonyl)amino]pyridine (3.50 g, 9.77 mmol) in THF (12.5 ml) was added (5 minutes) at −78° C. The mixture was then allowed to warm back to room temperature and stirred for 17 hours. The mixture was heated at 50° C. for 4 hours. The mixture was quenched by addition of saturated aqueous ammonium chloride (100 ml) and extracted with ethyl acetate (3×100 ml). The combined organic layers were dried (sodium sulphate), filtered and concentrated. Dichloromethane (50 ml) was added to the obtained residue (6.07 g), then the mixture was filtered off, yielding 1.30 g of a white solid. The filtrate was concentrated and then purified by flash column chromatography over silica gel (eluent: petroleum ether/ethyl acetate 100/0 to 60/40). The product fractions were collected and the solvent was evaporated, yielding 1.02 g of intermediate (81).

b) Preparation of intermediate (82)

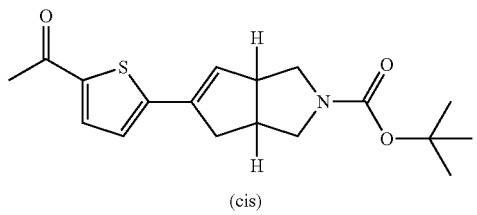

(cis)

The reaction was performed under argon atmosphere and monitored by TLC (petroleum ether/ethyl acetate 8/2, UV/PMA). 5-Acetyl-2-thienylboronic acid (0.057 g, 0.336 mmol) and 2M aqueous potassium carbonate (0.280 ml, 0.560 mmol) were added to a solution of intermediate (81) (0.100 g, 0.280 mmol) in 1,2-dimethoxyethane (5 ml). The mixture was purged with argon and tetrakis(triphenylphosphine)palladium (0) (0.032 g, 0.028 mmol) was added. Then, the mixture was heated at 80° C. overnight. The mixture was cooled to room temperature and then water (10 ml) and ethyl acetate (10 ml) were added. The organic layer was separated washed with water (10 ml) and with brine (10 ml), dried (sodium sulfate), filtered and evaporated until dryness under vacuum. The residue was purified by column chromatography over silica gel (eluent: petroleum ether/ethyl acetate 8/2). The desired fractions were collected and the solvent was evaporated, yielding 0.076 g of intermediate (82).

c) Preparation of intermediate (83)

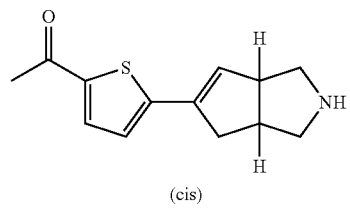

(cis)

The reaction was performed in anhydrous conditions under argon atmosphere and monitored by TLC (silica gel, dichloromethane/methanol 9/1, UV). Hydrogen chloride, 4M in dioxane (3.33 ml, 13.3 mmol) was added to a solution of intermediate (82) (0.444 g, 1.33 mmol) in dioxane (9 ml). The reaction mixture was stirred at room temperature for 70 hours and then concentrated until dryness, yielding 0.370 g of intermediate (83).

The following compounds were made using the same procedure as Example A.20b/A.20c whereby 5-acetyl-2-thienylboronic acid was replaced by 4-methylthiophene-2-boronic acid, 2-chlorothiophene-3-boronic acid, 4-methyl-3-thiophene-boronic acid, 2-acetyl-3-thiopheneboronic acid, 5-cyanothiophene-2-boronic acid, 5-chlorothiophene-2-boronic acid, 5-methylthiophene-2-boronic acid pinacol ester, 3-methylthiophene-2-boronic acid pinacol ester, or 3-methoxythiophene-2-boronic acid pinacol ester respectively.

intermediate (84)

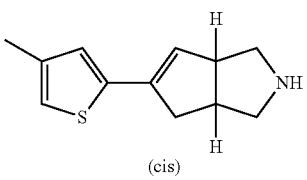

(cis)

intermediate (85)

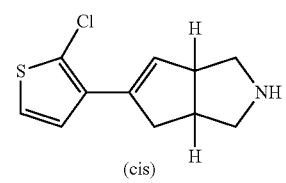

(cis)

intermediate (86)

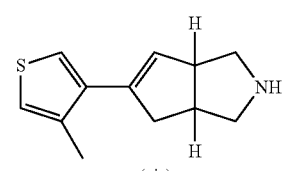

(cis)

intermediate (87)

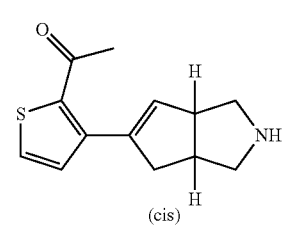

(cis)

-continued intermediate (88)

intermediate (89)

intermediate (90)

intermediate (91)

intermediate (92)

Example A.21 a) Preparation of intermediate (93)

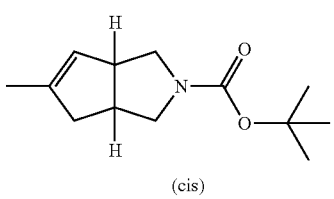
(cis)

The reaction was performed in anhydrous conditions under argon atmosphere and monitored by TLC (silica gel, eluent: petroleum ether/ethyl acetate 9/1, PMA). Methyllithium 1.6M in diethyl ether (3.29 ml, 5.26 mmol) was added to a suspension of Copper(I) iodide (0.794 g, 4.17 mmol) in THF (5.0 ml) at 0° C. After 1 hour, a solution of intermediate (81) (0.355 g, 0.993 mmol) in THF (2.1 ml) was added at 0° C. by cannula, rinsing with THF (2.1 ml).

The mixture was stirred at room temperature overnight. The mixture was quenched with an aqueous saturated solution of NH₄Cl (14 ml) and evaporated to dryness. The residue was purified by column chromatography over silica gel (eluent: pentane/ethyl acetate 95/5). The product fractions were collected and the solvent was evaporated, yielding 0.180 g of intermediate (93).

b) Preparation of intermediate (94)

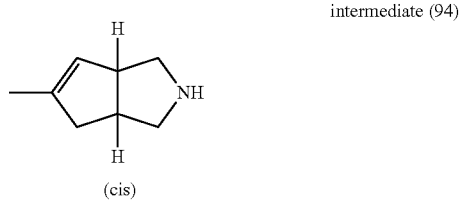
(cis)

The reaction was performed in anhydrous conditions under argon atmosphere and monitored by TLC (silica gel, eluent: petroleum ether/ethyl acetate 9/1, PMA). Hydrogen chloride 4M in dioxane (2.02 ml, 8.06 mmol) was added to a solution of intermediate (93) (0.180 g, 0.806 mmol) in 1,4-dioxane (4.3 ml), the solution was stirred at room temperature for 65 hours and was then concentrated to dryness, yielding 0.141 g of intermediate (94) (110%).

Example A.22 a) Preparation of intermediate (95)

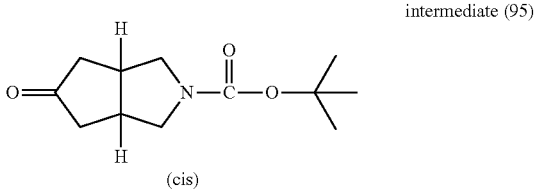 [SMILES: CC(C)(C)OC(=O)N1CC2CC(=O)CC2C1]
(cis)

The hydrogenation was performed in anhydrous conditions and monitored by TLC (silica gel, petroleum ether/ethyl acetate 50/50, developer: UV/PMA. A solution of intermediate (4) (6.93 g, 31.0 mmol) in THF (180 ml) was hydrogenated at room temperature (atmospheric pressure) with Palladium on carbon, 10 wt % loading (1.65 g) as catalyst for 15 hours. The catalyst was filtered off on clarcel, the filter cake was rinsed with dichloromethane (50 ml) and the combined filtrates were concentrated under reduced pressure to dryness. The obtained residue (7.26 g) was purified by column chromatography over silica gel (eluent: petroleum ether/ethyl acetate 80/20 to 50/50). The product fractions were collected and the solvent was evaporated, yielding 6.70 g of intermediate (95).

b) Preparation of intermediate (96)

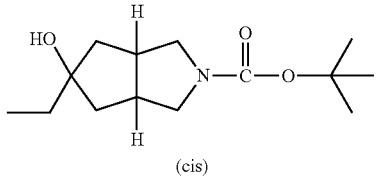

(cis)

The reaction was performed in anhydrous conditions under argon atmosphere and monitored by TLC (silica gel, eluent: petroleum ether/ethyl acetate 6/4, DCIP). Lanthanium trichloride lithium complex 0.6M in THF (3.70 ml, 2.22 mmol) was added to a solution of intermediate (95) (0.500 g, 2.22 mmol) in THF (15 ml). The mixture was stirred at room temperature for 1 hour, then cooled to 0° C. Ethylmagnesium bromide solution, 1.0M in THF (2.66 ml, 2.66 mmol) was added dropwise and the reaction mixture was allowed to warm to room temperature and was stirred for 18 hours. The mixture was quenched by addition of saturated aqueous NH$_4$Cl (50 ml) and extracted with ethyl acetate (3×50 ml). The combined organic layers were dried (Na$_2$SO$_4$), filtered and concentrated. The obtained residue (0.635 g) was purified by column chromatography over silica gel (eluent: petroleum ether/ethyl acetate 9/1 to 7/3). The product fractions were collected and the solvent was evaporated. The obtained residue (0.410 g) was purified by column chromatography over silica gel (eluent: petroleum ether/ethyl acetate 8/2). The product fractions were collected and the solvent was evaporated, yielding 0.235 g of intermediate (96).

c) Preparation of intermediate (97)

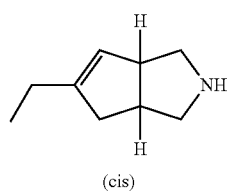

(cis)

The reaction was performed in anhydrous conditions under argon atmosphere and monitored by 1H NMR. HCl in dioxane (4 M, 2.30 ml, 9.20 mmol) was added to a solution of intermediate (96) (0.235 g, 0.920 mmol) in dioxane (2 ml). The reaction mixture was stirred at 60° C. for 18 hours. After cooling down to room temperature, the precipitate was filtered off on a glass frit and washed with diethyl ether (20 ml), yielding 0.126 g of solid. The filtrate was concentrated to dryness, yielding 0.077 g of residue. The solid and residue were combined and dissolved in dioxane (2 ml). 4M HCl in dioxane (2.30 ml, 9.20 mmol) was added and the mixture was stirred at 60° C. for 24 hours, then at 100° C. for 72 hours. The reaction mixture was concentrated to dryness, yielding 0.158 g of intermediate (97).

Example A.23 a) Preparation of intermediate (98)

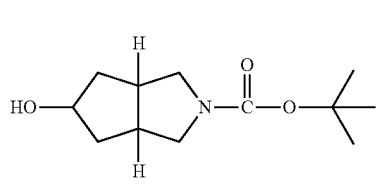

(cis)

The reaction was performed in anhydrous conditions under argon atmosphere and monitored by TLC (silica gel, eluent: petroleum ether/ethyl acetate 1/1, PMA). Sodium borohydride (0.893 g, 23.6 mmol) was added portionwise over a period of 30 minutes to a solution of intermediate (95) (2.66 g, 11.8 mmol) in MeOH (60 ml) at 0° C. The reaction mixture was stirred at 0° C. for 1 hour and then concentrated to dryness. The residue was diluted with ethyl acetate (200 ml) and washed with water (100 ml), 1M aqueous hydrochloric acid (100 ml) and brine (100 ml). The organic layer was dried (Na$_2$SO$_4$), filtered and concentrated, yielding 2.27 g of intermediate (98).

b) Preparation of intermediate (99)

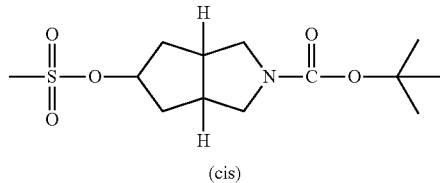

(cis)

The reaction was performed in anhydrous conditions under argon atmosphere and monitored by TLC (silica gel, eluent: petroleum ether/ethyl acetate 1/1, PMA). Methanesulfonyl chloride (0.930 ml, 11.9 mmol) was added dropwise to a solution of intermediate (98) (2.27 g, 9.98 mmol) and triethylamine (4.17 ml, 29.9 mmol) in DCM (50 ml) at 0° C. The reaction mixture was stirred at room temperature for 1 hour and concentrated to dryness. The residue was diluted in ethyl acetate (200 ml) and washed with water (100 ml), brine (100 ml), 1M aqueous hydrochloric acid (100 ml) and brine (100 ml) again. The organic layer was dried (Na$_2$SO$_4$), filtered and concentrated. The obtained residue (2.52 g) was purified by column chromatography over silica gel (eluent: petroleum ether/ethyl acetate, 8/2 to 5/5). The product fractions were collected and the solvent was evaporated, yielding 2.39 g of intermediate (99).

c) Preparation of

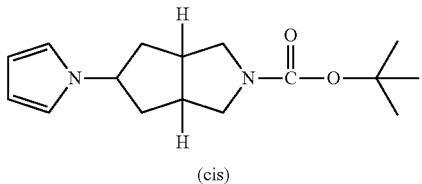
intermediate (100)
(cis)

The reaction was performed in anhydrous conditions under argon atmosphere and monitored by TLC (silica gel, eluent: petroleum ether/ethyl acetate, 8/2, ninhydrine/PMA). Intermediate (99) (0.300 g, 0.982 mmol) was dissolved in DMF (3 ml) and the mixture was cooled to 0° C. Pyrrole (0.102 ml, 1.47 mmol) and sodium hydride, 60% dispersion in mineral oil (0.0589 g, 1.47 mmol) were added and the reaction mixture was stirred at room temperature for 18 hours. The reaction mixture was diluted with ethyl acetate (50 ml) and washed with water (2×50 ml), then with brine (3×50 ml). The organic layer was dried (Na$_2$SO$_4$), filtered and concentrated. The obtained residue (0.290 g) was purified by column chromatography over silica gel (eluent: petroleum ether/ethyl acetate, 98/2 to 95/5, then 90/10). The product fractions were collected and the solvent was evaporated, yielding 0.175 g of intermediate (100).

d) Preparation of

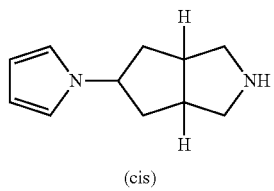
intermediate (101)
(cis)

The reaction was performed in anhydrous conditions under argon atmosphere and monitored by TLC (silica gel, eluent: petroleum ether/ethyl acetate, 6/4, PMA). 4M HCl in dioxane (1.58 ml, 6.33 mmol) was added to a solution of intermediate (100) (0.175 g, 0.633 mmol) in dioxane (3 ml). The reaction mixture was stirred at 50° C. for 2 hours and concentrated to dryness, yielding 0.135 g of intermediate (101).

The following compounds were made using the same procedure as Example A.23c/A.23d whereby pyrrole was replaced by tetrazole, pyrazole, 1,2,4-triazole, 1,2,3-triazole or phenol respectively.

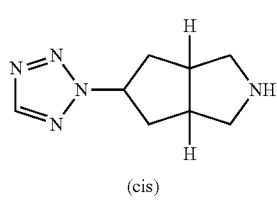
intermediate (102)
(cis)

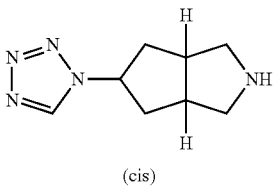
intermediate (103)
(cis)

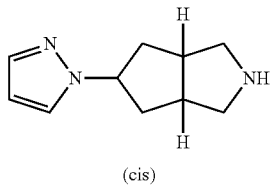
intermediate (104)
(cis)

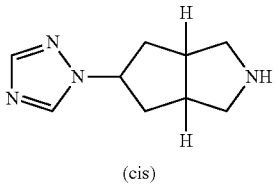
intermediate (105)
(cis)

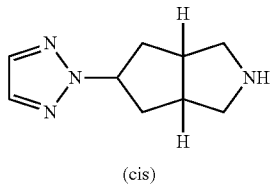
intermediate (106)
(cis)

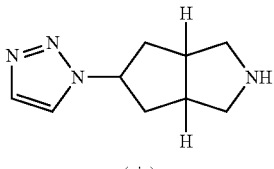
intermediate (107)
(cis)

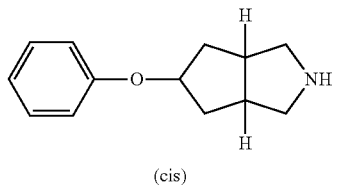
intermediate (108)
(cis)

Example A.24 a) Preparation of

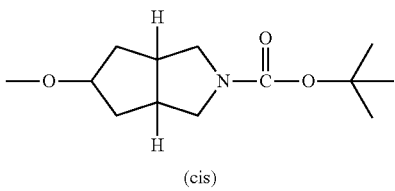
intermediate (109)
(cis)

The reaction was performed in anhydrous conditions under argon atmosphere and monitored by TLC (silica gel, eluent: petroleum ether/ethyl acetate, 8/2, ninhydrine/PMA). Sodium methoxide 25 wt % solution in methanol (0.449 ml, 1.96 mmol) was added to a solution of intermediate (99) (0.300 g, 0.982 mmol) in MeOH (4 ml). The mixture was stirred under reflux for 20 hours. The reaction mixture was concentrated to dryness. The residue was diluted with ethyl acetate (50 ml) and washed with water (50 ml), then with brine (50 ml). The organic layer was dried (Na$_2$SO$_4$), filtered and concentrated. The obtained residue was purified by column chromatography over silica gel (eluent: petroleum ether/ethyl acetate, 100/0 to 97/3, then 1/1). The product fractions were collected and the solvent was evaporated, yielding 0.182 g of intermediate (109).

b) Preparation of

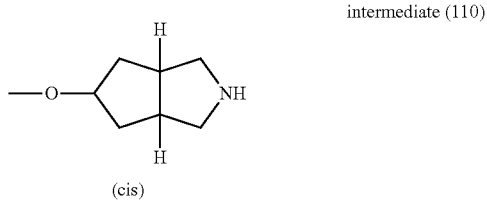

intermediate (110)

(cis)

The reaction was performed in anhydrous conditions under argon atmosphere and monitored by TLC (silica gel, eluent: petroleum ether/ethyl acetate, 8/2, ninhydrine/PMA). 4M HCl in dioxane (1.88 ml, 7.54 mmol) was added to a solution of intermediate (109) (0.182 g, 0.754 mmol) in dioxane (4 ml). The reaction mixture was stirred at room temperature for 18 hours, then at 50° C. for 2 hours. The reaction mixture was concentrated to dryness, yielding 0.139 g of intermediate (110).

Some intermediate compounds used in the preparation of the final compounds are commercially available such as.

B. Synthesis of the Final Compounds

Example B.1

Preparation of

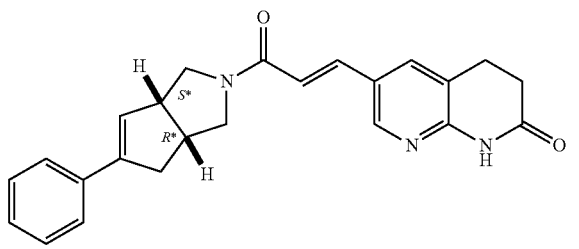

compound (14)

A mixture of intermediate (3) (9.4 g, 36.9 mmol), intermediate (9) (8.2 g, 44.3 mmol), EDCI (8.5 g, 44.3 mmol), hydroxybenzotriazole (6.0 g, 44.3 mmol) and triethylamine (15.4 ml, 0.111 mmol) in CH$_2$Cl$_2$ (160 ml) and THF (160 ml) was stirred overnight at room temperature. Water (175 ml) was added, the precipitate was filtered off, washed with water/EtOH (50 ml). The solid was suspended in EtOH (50 ml) and stirred for 15 minutes. The resulting suspension was filtered off and dried under vacuum at 70° C. to give 7.3 g of compound (14) as a white powder (mp=266° C.), ([α]$_D^{20}$=−105.1° (589 nm, c 0.1275 w/v %, CH$_2$Cl$_2$, 20° C.).

$^1$H NMR (500 MHz, DMSO-d$_6$) δ (ppm) 10.64 (d, J=7.6 Hz, 1H), 8.33 (dd, J=1.7, 9.6 Hz, 1H), 8.04 (d, J=17.3 Hz, 1H), 7.48 (d, J=7.6 Hz, 2H), 7.31-7.42 (m, 3H), 7.23-7.28 (m, 1H), 6.99 (t, J=15.0 Hz, 1H), 6.20 (d, J=6.0 Hz, 1H), 3.38-4.04 (m, 5H), 3.09-3.21 (m, 1H), 2.85-3.04 (m, 3H), 2.55-2.67 (m, 3H).

Example B.2

Preparation of

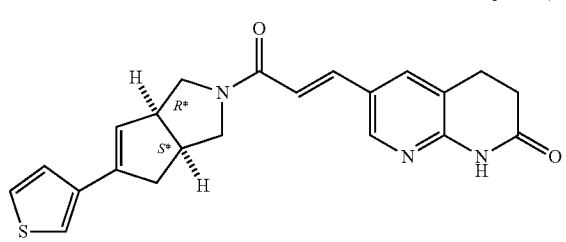

compound (44)

A solution of intermediate (14) (5.8 g, 30.32 mmol), intermediate (3) (7.72 g, 30.32 mmol), 1-hydroxybenzotriazole (4.92 g, 36.38 mmol), EDCI (6.97 g, 36.38 mmol) and triethylamine (14.71 mL, 106.12 mmol) in CH$_2$Cl$_2$ (100 ml) and THF (100 ml) was stirred overnight at room temperature. The mixture was poured out into water. The precipitate was filtered off and washed twice with EtOH and dried under vacuum at 65° C. This precipitate was crystallized from EtOH, filtered off and dried under vacuum at 62° C. to give 9.02 g of compound (44) as a white powder, (mp=264° C.) ([α]$_D^{20}$=+170.12° (589 nm, c 0.2075 w/v %, CH$_2$Cl$_2$, 20° C.)).

$^1$H NMR (400 MHz, DMSO-d$_6$) δ (ppm) 10.63 (d, J=4.5 Hz, 1H), 8.32 (d, J=5.1 Hz, 1H), 8.03 (d, J=10.6 Hz, 1H), 7.52 (dd, J=2.8, 4.8 Hz, 1H), 7.41 (br. s., 1H), 7.36 (dd, J=4.8, 9.3 Hz, 2H), 6.98 (dd, J=9.1, 15.7 Hz, 1H), 6.01 (br. s., 1H), 3.35-4.03 (m, 5H), 2.94-3.21 (m, 2H), 2.90 (q, J=7.9 Hz, 3H), 2.52-2.62 (m, 2H).

Example B.3

Preparation of

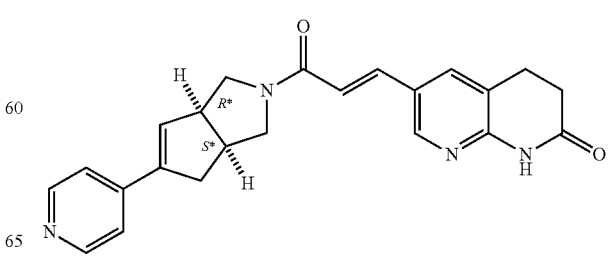

compound (40)

A solution of intermediate (19) (21.1 g, 81.4 mmol), intermediate (3) (17.3 g, 67.8 mmol), 1-hydroxybenzotriazole (11.0 g, 81.4 mmol), EDCI (15.6 g, 81.4 mmol) and triethylamine (47 ml, 0.339 mol) in CH$_2$Cl$_2$ (350 ml) and THF (350 ml) was stirred overnight at room temperature. Water was added to the mixture. The precipitate was filtered off, washed with water/EtOH then EtOH and dried at 70° C. under vacuum to give 12.7 g of compound (40) as a white powder (mp=271° C.) ([α]$_D^{20}$=+116.08° (589 nm, c 0.2145 w/v %, CH$_2$Cl$_2$, 20° C.)).

$^1$H NMR (400 MHz, DMSO-d$_6$) δ (ppm) 10.63 (d, J=5.1 Hz, 1H), 8.52 (d, J=5.6 Hz, 2H), 8.33 (d, J=6.1 Hz, 1H), 8.03 (d, J=13.6 Hz, 1H), 7.41-7.46 (d, J=15.7 Hz, 2 H), 7.38 (d, J=4.0 Hz, 1H), 6.98 (dd, J=11.6, 15.7 Hz, 1H), 6.53 (d, J=8.1 Hz, 1H), 3.37-4.04 (m, 5H), 2.86-3.22 (m, 5H), 2.58-2.70 (m, 2H).

compound (41)

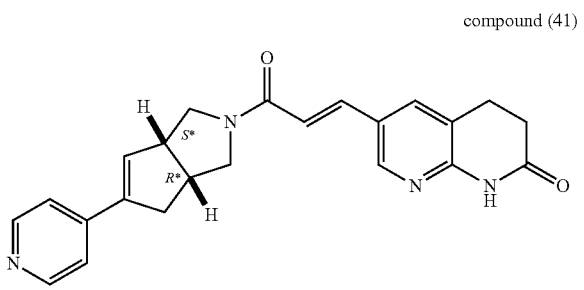 [SMILES: O=C1CCc2cc(/C=C/C(=O)N3C[C@@H]4CC(c5ccncc5)=C[C@@H]4C3)cnc2N1]

Compound (41) was prepared analogously by reacting intermediate (20) with intermediate (3) following the same procedure.

$^1$H NMR (500 MHz, DMSO-d$_6$) δ (ppm) 10.63 (d, J=5.1 Hz, 1H), 8.52 (d, J=5.6 Hz, 2H), 8.33 (d, J=6.1 Hz, 1H), 8.03 (d, J=13.6 Hz, 1H), 7.41-7.46 (d, J=15.7 Hz, 2H), 7.38 (d, J=4.0 Hz, 1H), 6.98 (dd, J=11.6, 15.7 Hz, 1H), 6.53 (d, J=8.1 Hz, 1H), 3.37-4.04 (m, 5H), 2.86-3.22 (m, 5H), 2.58-2.70 (m, 2H).

([α]$_D^{20}$=-115.85° (589 nm, c 0.183 w/v %, CH$_2$Cl$_2$, 20° C.)).

Example B.4 a) Preparation of intermediate (111)

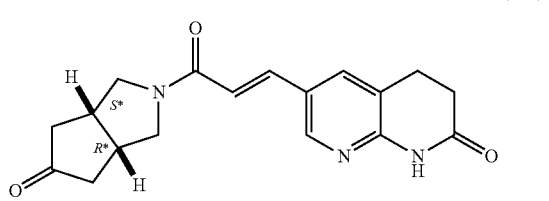

The reaction was performed under Ar-atmosphere and monitored by TLC (silica gel, CH$_2$Cl$_2$/methanol/triethylamine 95/5/0.1, UV/PMA). 1-(3-Dimethylaminopropyl)-3-ethylcarbodiimide (.HCl) (1.70 g, 8.87 mmol) was added to a mixture of intermediate (3) (2.02 g, 7.39 mmol), crude cis hexahydro-cyclopenta[c]pyrrol-5(1H)one (1.85 g, maximal 8.89 mmol), 1-hydroxybenzotriazole monohydrate (1.36 g, 8.87 mmol) and N-ethyldiisopropylamine (6.32 ml, 36.9 mmol) in DMF (75 ml). The mixture was stirred at room temperature overnight for 18 hours. The mixture was concentrated under reduced pressure, diluted with dichloromethane (150 ml) and washed with saturated aqueous NaHCO$_3$ (100 ml). The aqueous layer was extracted back with dichloromethane (2×150 ml). The combined organic layers were washed with brine (400 ml), dried (Na$_2$SO$_4$), filtered and concentrated under reduced pressure to dryness. The obtained residue was purified by flash column chromatography over silica gel (eluent: dichloromethane/methanol 100/0 to 94/6). The product fractions were collected and the solvent was evaporated. The basic aqueous layers were extracted again with dichloromethane (3×300 ml). The combined organic layers were washed with brine (900 ml), dried (Na$_2$SO$_4$), filtered and concentrated under reduced pressure to dryness. The obtained residue was purified by flash column chromatography over silica gel (eluent: dichloromethane/methanol 100/0 to 94/6). The product fractions were collected and the solvent was evaporated. The desired residues were combined, yielding 1.58 g of intermediate (111).

b) Preparation of compound (71)

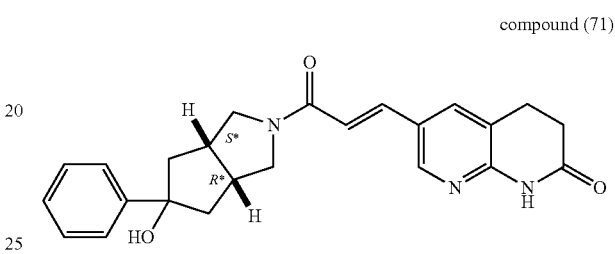

The reaction was performed in anhydrous conditions under argon atmosphere and monitored by TLC (silica gel, dichloromethane/methanol 95/5, UV/PMA). Lanthanum trichloride lithium chloride complex 0.6M THF (2.38 ml, 1.43 mmol) was added to a suspension of intermediate (111) (0.464 g, 1.43 mmol) in THF (18 ml). The mixture was stirred at room temperature for 1 hour, then cooled to 0° C. Phenylmagnesium bromide solution 1.0 M in THF (3.57 ml, 3.57 mmol) was added dropwise. The reaction mixture was stirred and allowed to warm back to room temperature for 3 days. Additional phenylmagnesium bromide solution 1.0 M in THF (2.85 ml, 2.85 mmol, 2 equivalents) was added dropwise. The mixture was stirred at room temperature additional 2 days. The mixture was quenched by addition of saturated aqueous ammonium chloride (30 ml) and extracted with EtOAc (3×30 ml). The combined organic layers were dried (Na$_2$SO$_4$), filtered and concentrated under reduced pressure to dryness. The obtained residue (0.801 g) was purified by flash column chromatography over silica gel (eluent: CH$_2$Cl$_2$/MeOH 100/0 to 95/5). The solvent of the collected product fractions was evaporated. The residue was triturated with diethyl ether (2×3 ml), and then dried under vacuum, yielding 0.077 g of compound (71).

Example B.5

Preparation of compound (73)

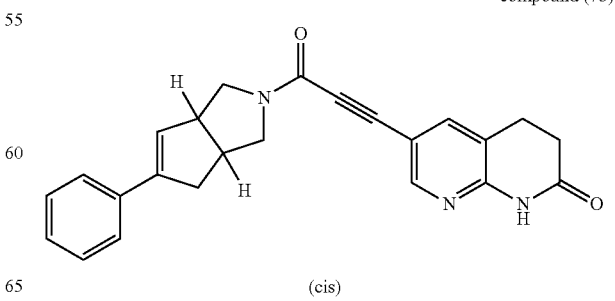

(cis)

A mixture of intermediate (23) (0.032 g, 0.097 mmol), intermediate (8) (0.032 g, 0.145 mmol), EDCI (0.022 g, 0.0116 mmol), HOBT (0.016 g, 0.116 mmol) and triethylamine (0.049 ml, 0.349 mmol) in DCM (1 ml) and THF (1 ml) was stirred overnight at room temperature. Water was added, the mixture was extracted with DCM, the organic layer was separated, washed with water, dried (MgSO$_4$) and evaporated till dryness. The residue was crystallized from EtOH, the solid was filtered off, washed with EtOH, and dried (vacuum 70° C.), yielding 0.015 g of compound (73).

Table F-1 lists the compounds that were prepared according to one of the above Examples.

TABLE F-1

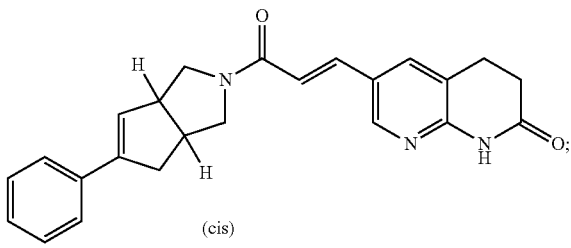

Co. No. 1

(cis)

Ex. B.1

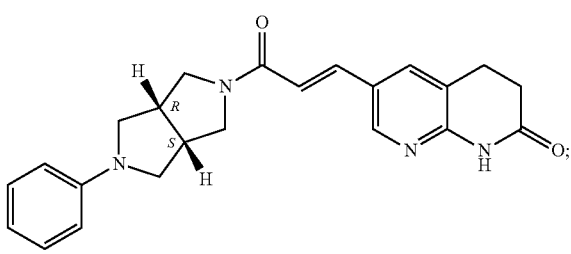

Co. No. 2

Ex. B.1

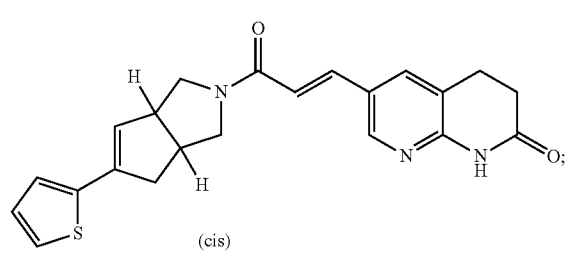 [SMILES: O=C1CCc2cc(/C=C/C(=O)N3CC4C=C(c5cccs5)CC4C3)cnc2N1]

Co. No. 3

(cis)

Ex. B.1

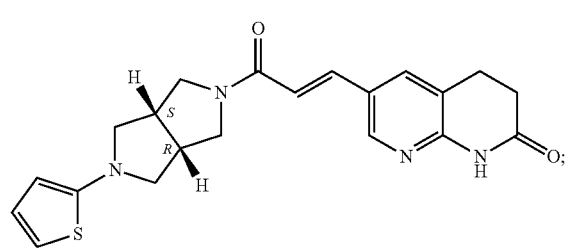

Co. No. 4

Ex. B.1

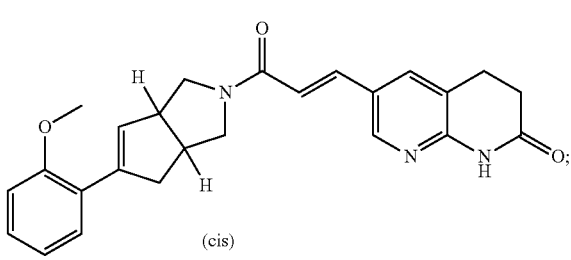 [SMILES: COc1ccccc1C1=CC2CN(C(=O)/C=C/c3cnc4c(c3)CCC(=O)N4)CC2C1]

Co. No. 5

(cis)

Ex. B.1

TABLE F-1-continued
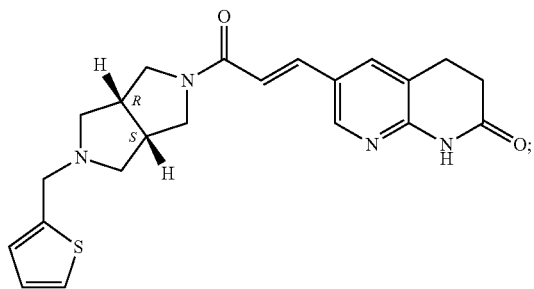
Co. No. 6
Ex. B.1
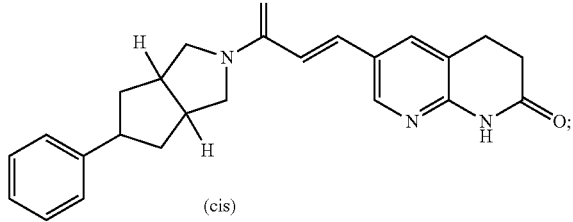
(cis)
Co. No. 7
Ex. B.1
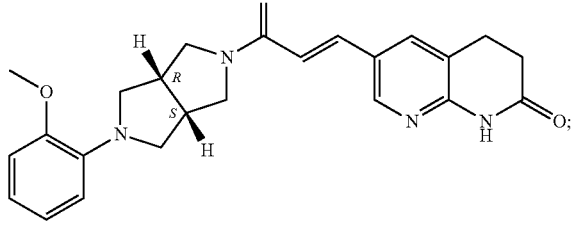
Co. No. 8
Ex. B.1
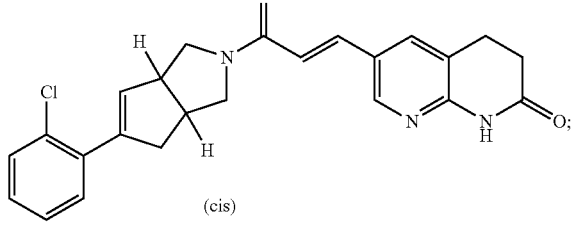
(cis)
Co. No. 9
Ex. B.1
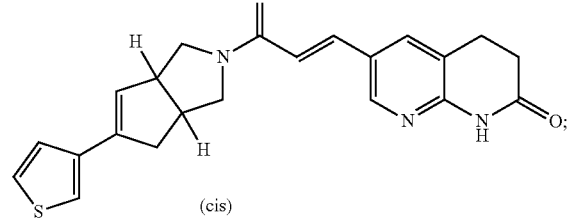
(cis)
Co. No. 10
Ex. B.1
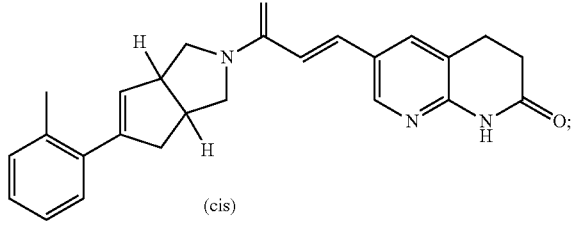
(cis)
Co. No. 11
Ex. B.1

TABLE F-1-continued
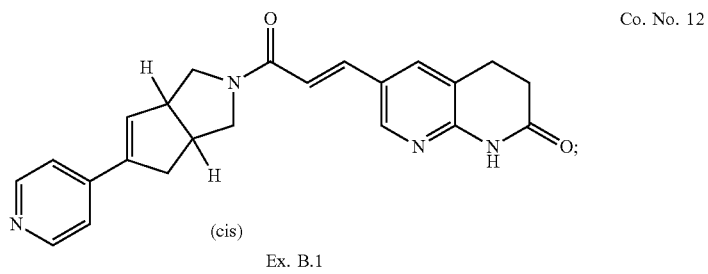
Co. No. 12
(cis)
Ex. B.1
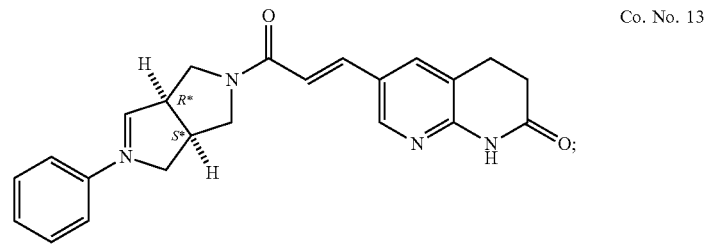
Co. No. 13
Ex. B.1; $[\alpha]_D^{20}$ = +104.17° (589 nm, c = 0.096 w/v %, CH$_2$Cl$_2$, 20° C.)
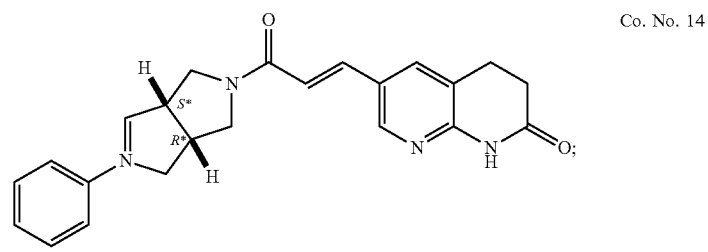
Co. No. 14
Ex. B.1
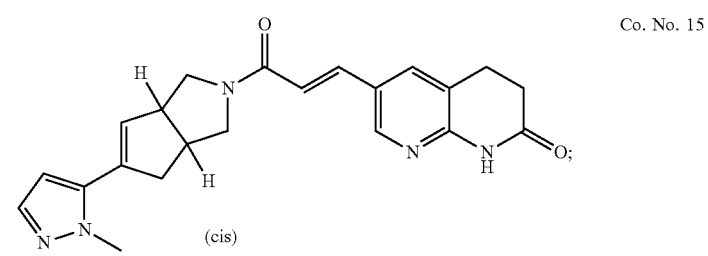
Co. No. 15
(cis)
Ex. B.1
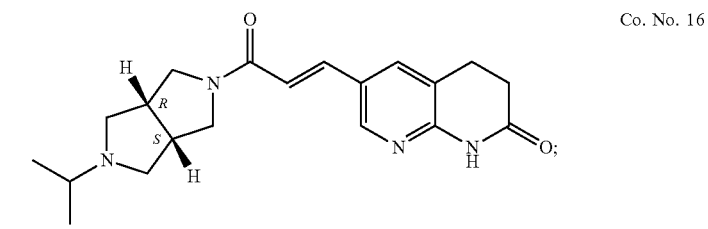
Co. No. 16
Ex. B.1
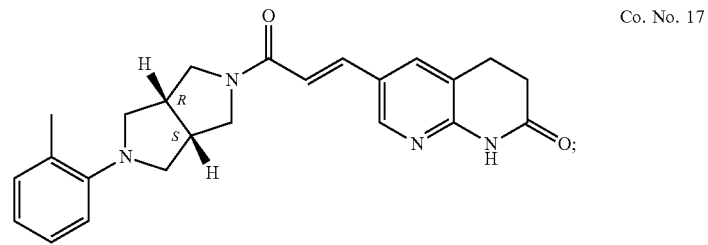
Co. No. 17
Ex. B.1

TABLE F-1-continued
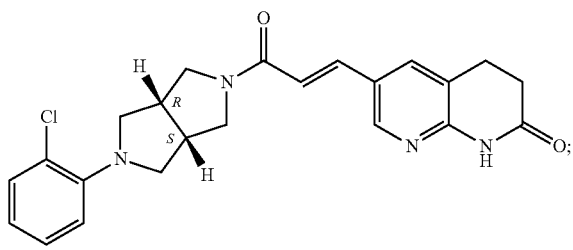
Co. No. 18
Ex. B.1
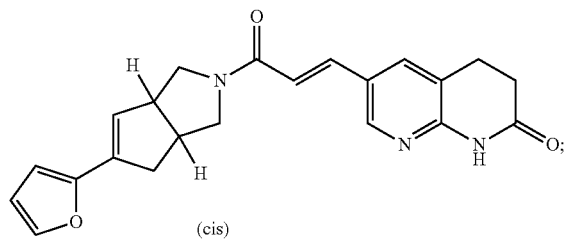 [SMILES: O=C1CCc2cc(/C=C/C(=O)N3CC4C=C(c5ccco5)CC4C3)cnc2N1]
(cis)
Ex. B.1
Co. No. 19
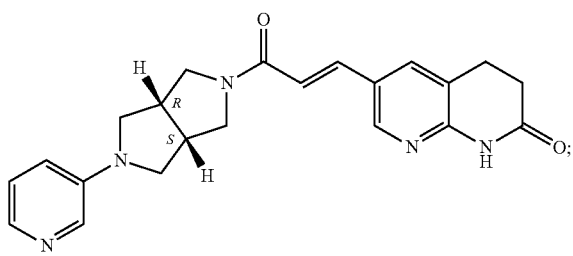
Ex. B.1
Co. No. 20
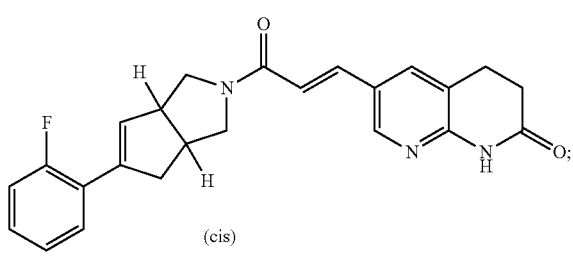 [SMILES: O=C1CCc2cc(/C=C/C(=O)N3CC4C=C(c5ccccc5F)CC4C3)cnc2N1]
(cis)
Ex. B.1
Co. No. 21
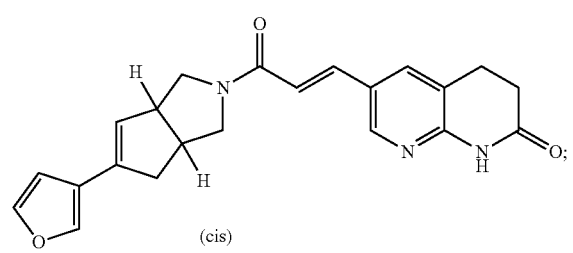 [SMILES: O=C1CCc2cc(/C=C/C(=O)N3CC4C=C(c5ccoc5)CC4C3)cnc2N1]
(cis)
Ex. B.1
Co. No. 22
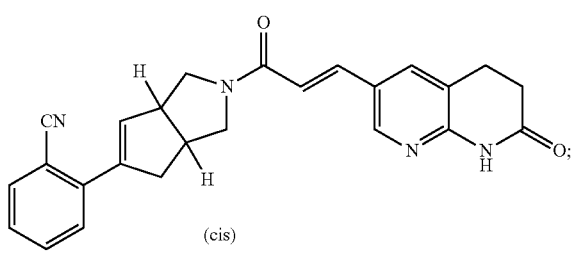 [SMILES: N#Cc1ccccc1C1=CC2CN(C(=O)/C=C/c3cnc4c(c3)CCC(=O)N4)CC2C1]
(cis)
Ex. B.1
Co. No. 23

TABLE F-1-continued
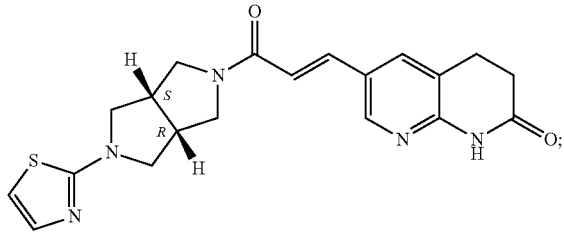
Co. No. 24
Ex. B.1
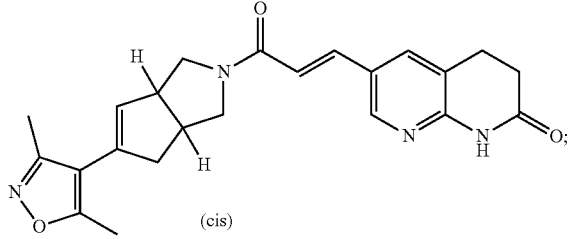 [SMILES: Cc1noc(C)c1C1=CC2CN(C(=O)/C=C/c3cnc4c(c3)CCC(=O)N4)CC2C1]
Co. No. 25
(cis)
Ex. B.1
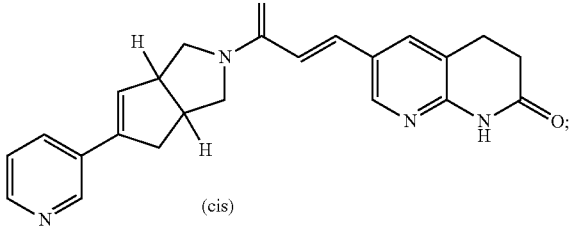
Co. No. 26
(cis)
Ex. B.1
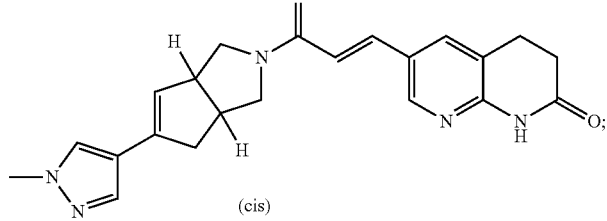
Co. No. 27
(cis)
Ex. B.1
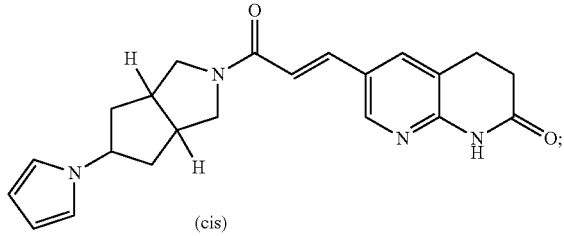 [SMILES: O=C1CCc2cc(/C=C/C(=O)N3CC4CC(n5cccc5)CC4C3)cnc2N1]
Co. No. 28
(cis)
Ex. B.1
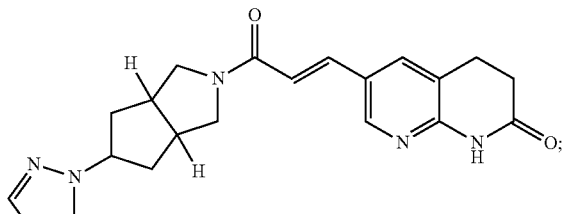
Co. No. 29
(cis)
Ex. B.1

TABLE F-1-continued
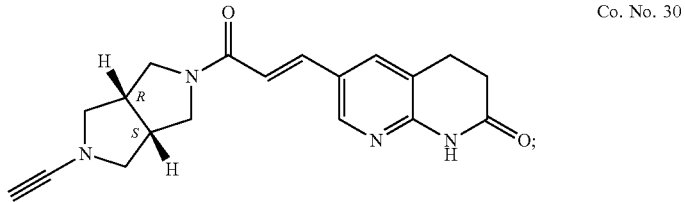
Co. No. 30
Ex. B.1
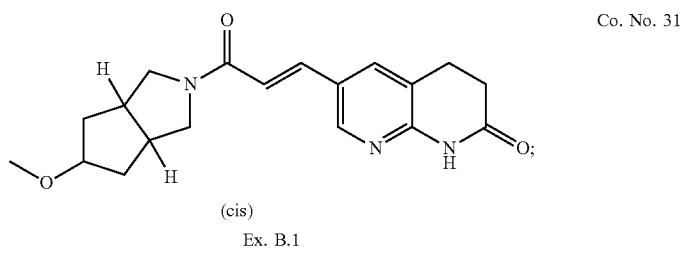
(cis)
Ex. B.1
Co. No. 31
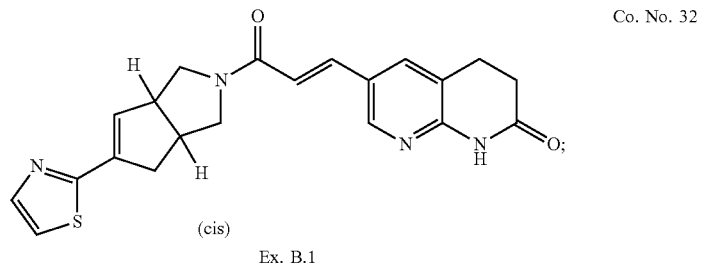
(cis)
Ex. B.1
Co. No. 32
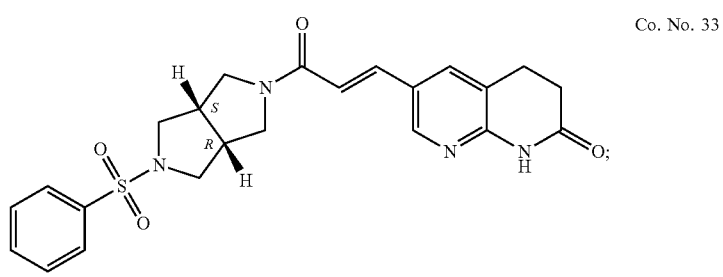
Ex. B.1
Co. No. 33
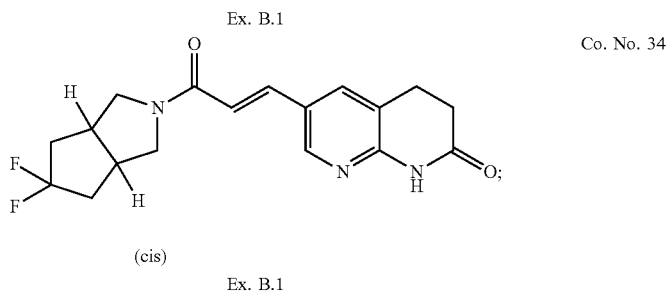
(cis)
Ex. B.1
Co. No. 34
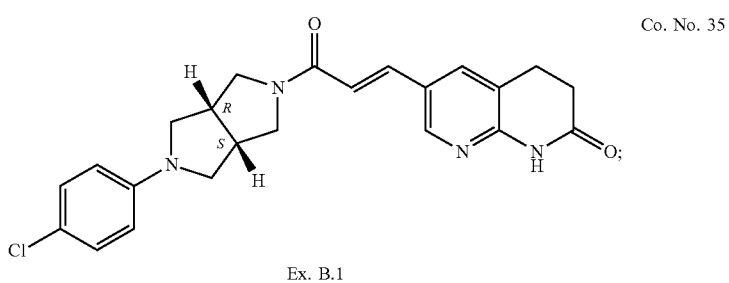
Ex. B.1
Co. No. 35

TABLE F-1-continued
| | |
|---|---|
| 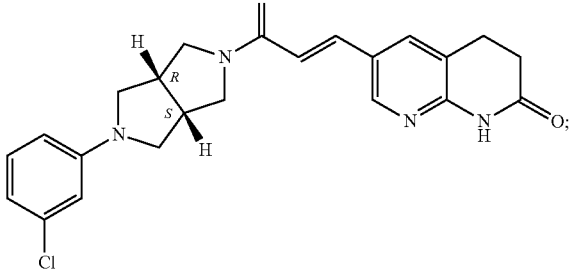<br>Ex. B.1 | Co. No. 36 |
| 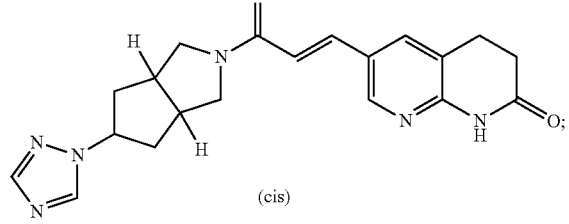<br>(cis)<br>Ex. B.1 | Co. No. 37 |
| 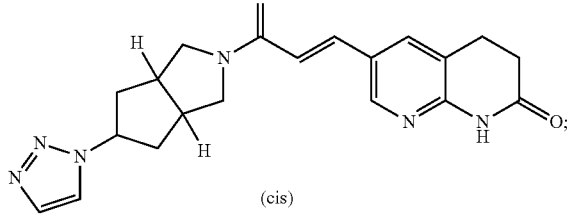<br>(cis)<br>Ex. B.1 | Co. No. 38 |
| 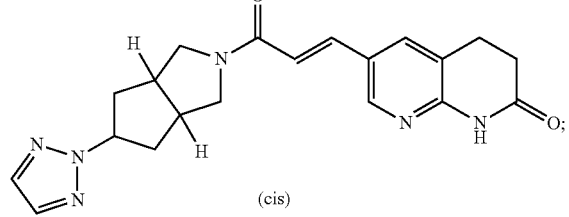<br>(cis)<br>Ex. B.1 | Co. No. 39 |
| 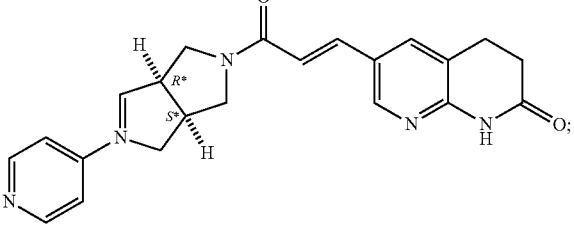<br>Ex. B.3 | Co. No. 40 |
| 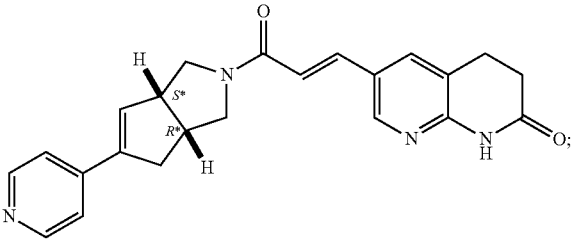<br>Ex. B.3 | Co. No. 41 |

TABLE F-1-continued
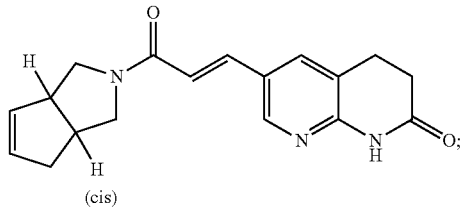 [SMILES: O=C1CCc2cc(/C=C/C(=O)N3CC4C=CCC4C3)cnc2N1]
(cis)
Ex. B.1
Co. No. 42
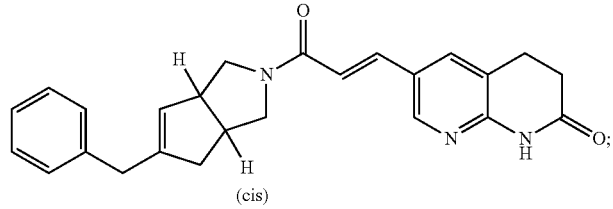 [SMILES: O=C1CCc2cc(/C=C/C(=O)N3CC4C=C(Cc5ccccc5)CC4C3)cnc2N1]
(cis)
Ex. B.1
Co. No. 43
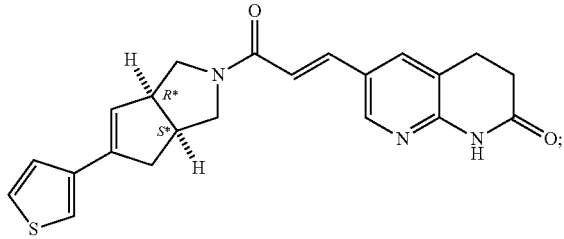
Ex. B.2
Co. No. 44
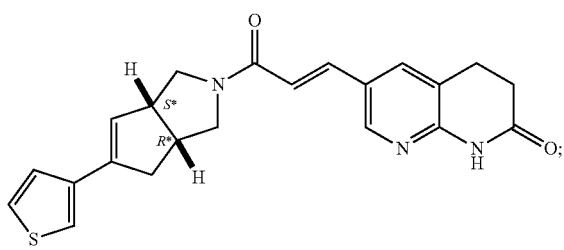
Ex. B.1; $[\alpha]_D^{20} = -161.79°$
(589 nm, c = 2015 w/v %, CH$_2$Cl$_2$, 20° C.)
Co. No. 45
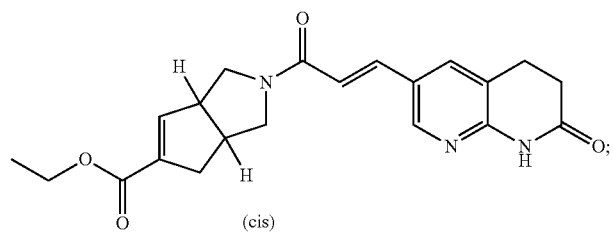 [SMILES: CCOC(=O)C1=CC2CN(C(=O)/C=C/c3cnc4c(c3)CCC(=O)N4)CC2C1]
(cis)
Ex. B.1
Co. No. 46
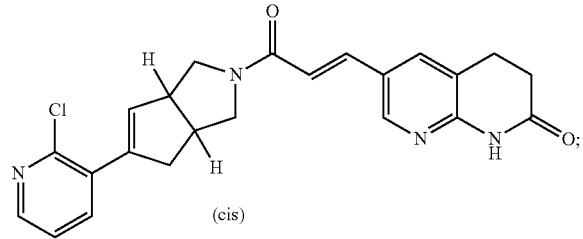 [SMILES: O=C1CCc2cc(/C=C/C(=O)N3CC4C=C(c5cccnc5Cl)CC4C3)cnc2N1]
(cis)
Ex. B.1
Co. No. 47

TABLE F-1-continued
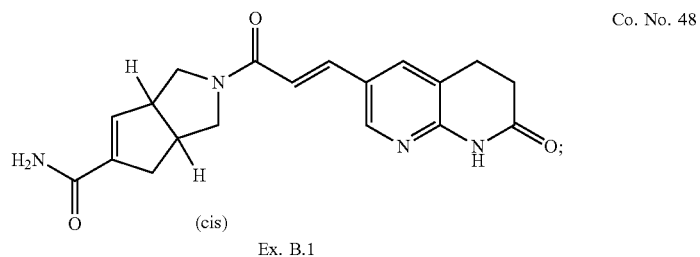
Co. No. 48
(cis)
Ex. B.1
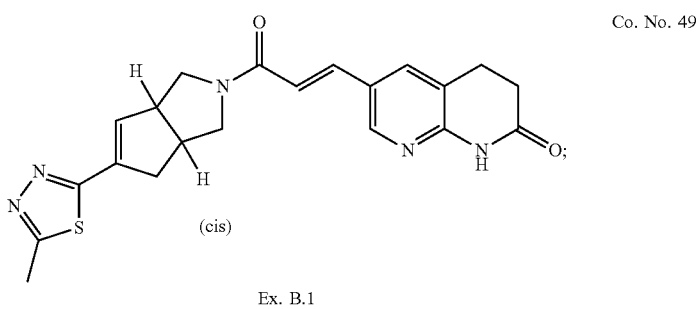
Co. No. 49
(cis)
Ex. B.1
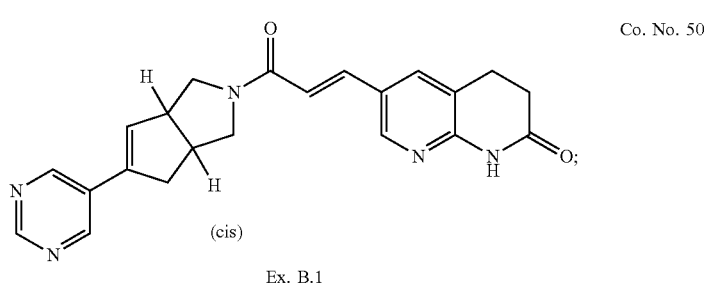
Co. No. 50
(cis)
Ex. B.1
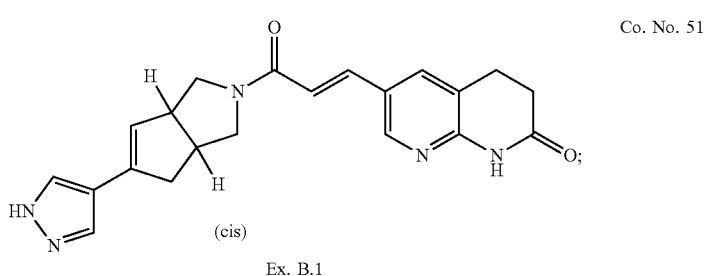
Co. No. 51
(cis)
Ex. B.1
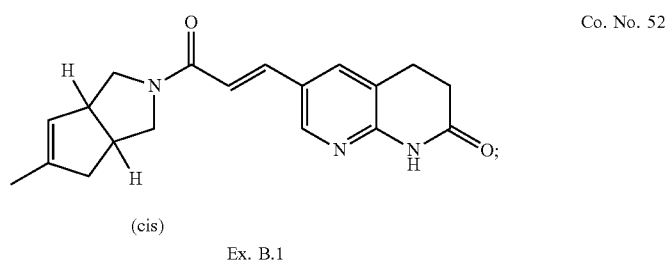
Co. No. 52
(cis)
Ex. B.1
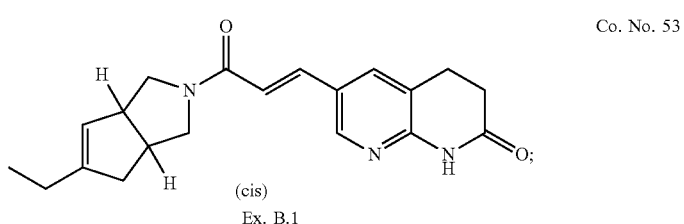
Co. No. 53
(cis)
Ex. B.1

TABLE F-1-continued
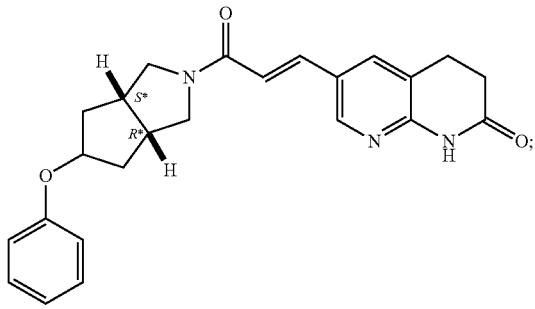
Co. No. 54
Ex. B.1
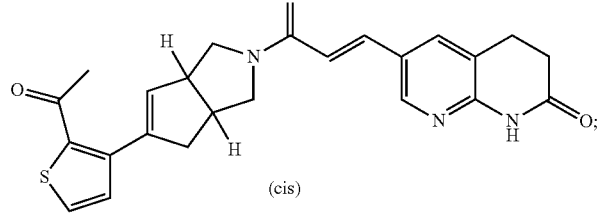
Co. No. 55
(cis)
Ex. B.1
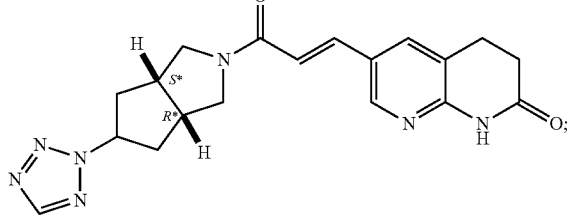
Co. No. 56
Ex. B.1
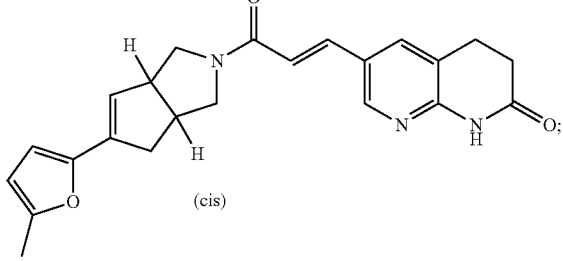
Co. No. 57
(cis)
Ex. B.1
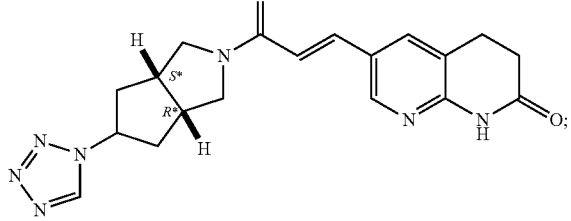
Co. No. 58
Ex. B.1

TABLE F-1-continued
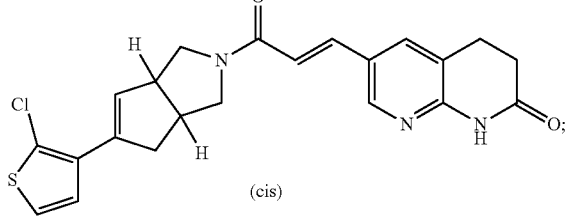
Co. No. 59
(cis)
Ex. B.1
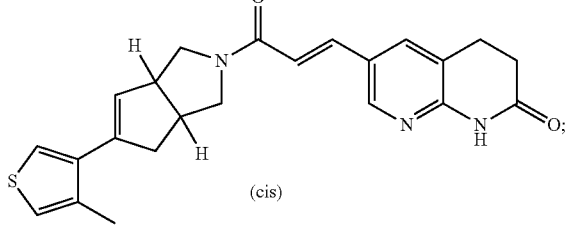
Co. No. 60
(cis)
Ex. B.1
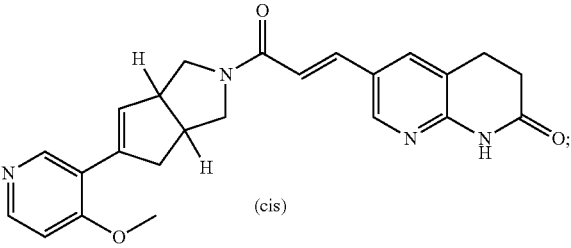 [SMILES: COc1ccncc1C1=CC2CN(C(=O)/C=C/c3cnc4c(c3)CCC(=O)N4)CC2C1]
Co. No. 61
(cis)
Ex. B.1
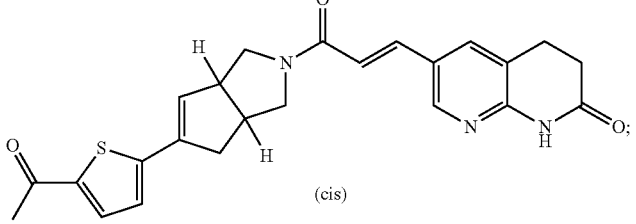
Co. No. 62
(cis)
Ex. B.1
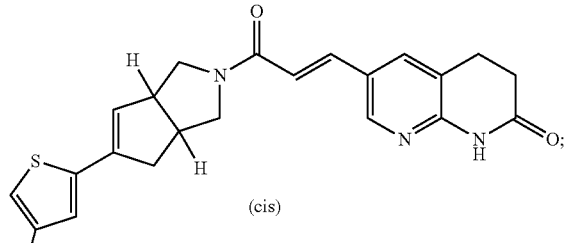
Co. No. 63
(cis)
Ex. B.1
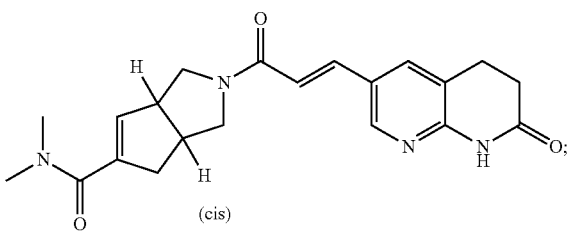 [SMILES: CN(C)C(=O)C1=CC2CN(C(=O)/C=C/c3cnc4c(c3)CCC(=O)N4)CC2C1]
Co. No. 64
(cis)
Ex. B.1

TABLE F-1-continued
| | |
|---|---|
| 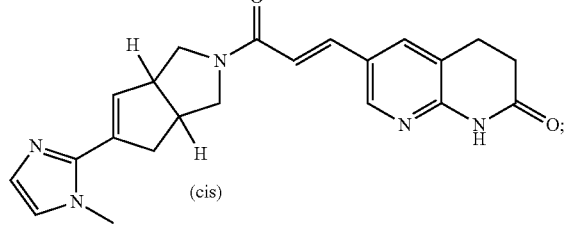 (cis) Ex. B.1 | Co. No. 65 |
| 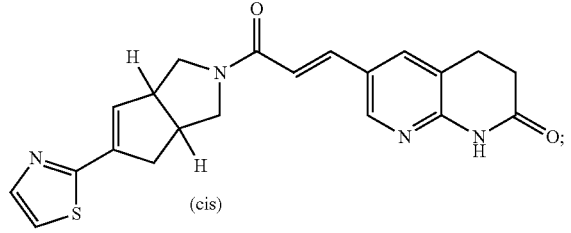 [SMILES: O=C1CCc2cc(/C=C/C(=O)N3CC4C=C(c5nccs5)CC4C3)cnc2N1] (cis) Ex. B.1 | Co. No. 66 |
| 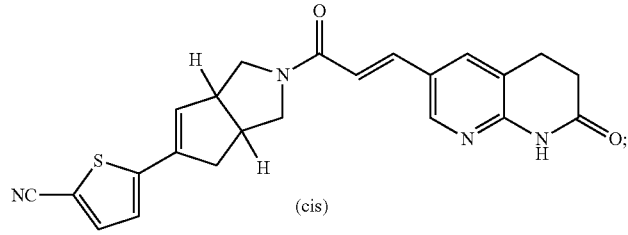 [SMILES: N#Cc1ccc(C2=CC3CN(C(=O)/C=C/c4cnc5c(c4)CCC(=O)N5)CC3C2)s1] (cis) Ex. B.1 | Co. No. 67 |
| 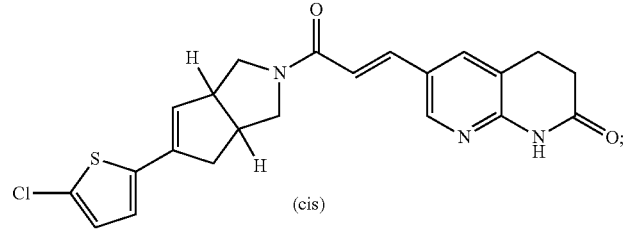 [SMILES: O=C1CCc2cc(/C=C/C(=O)N3CC4C=C(c5ccc(Cl)s5)CC4C3)cnc2N1] (cis) Ex. B.1 | Co. No. 68 |
| 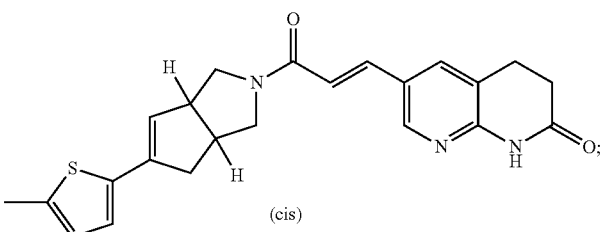 (cis) Ex. B.1 | Co. No. 69 |
| 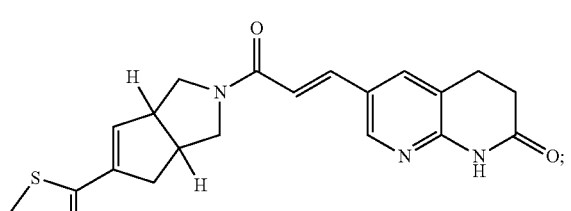 (cis) Ex. B.1 | Co. No. 70 |

TABLE F-1-continued

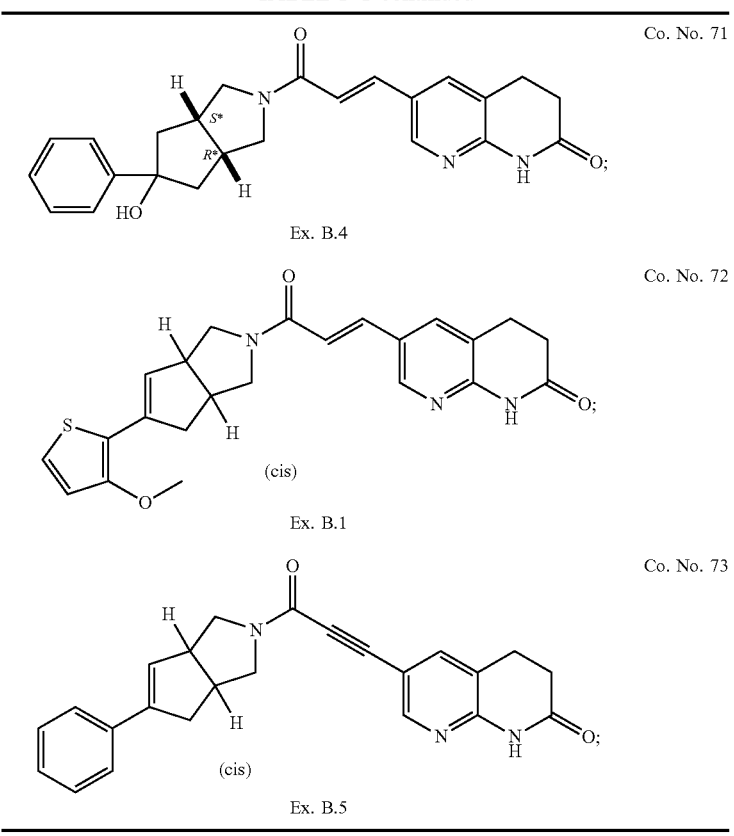

Co. No. 71
Ex. B.4

Co. No. 72
Ex. B.1

Co. No. 73
Ex. B.5

C. Compound Identification

C1. LCMS

For LCMS-characterization of the compounds of the present invention, the following methods were used.

General Procedure A

The LC measurement was performed using a UPLC (Ultra Performance Liquid Chromatography) Acquity (Waters) system comprising a binary pump with degasser, an autosampler, a diode-array detector (DAD) and a column as specified in the respective methods below, the column is hold at a temperature of 40° C. Flow from the column was brought to a MS detector. The MS detector was configured with an electrospray ionization source. The capillary needle voltage was 3 kV and the source temperature was maintained at 130° C. on the Quattro (triple quadrupole mass spectrometer from Waters). Nitrogen was used as the nebulizer gas. Data acquisition was performed with a Waters-Micromass MassLynx-Openlynx data system.

General Procedure B

The HPLC measurement was performed using an Alliance HT 2795 (Waters) system comprising a quaternary pump with degasser, an autosampler, a diode-array detector (DAD) and a column as specified in the respective methods below, the column is hold at a temperature of 30° C. Flow from the column was split to a MS spectrometer. The MS detector was configured with an electrospray ionization source. The capillary needle voltage was 3 kV and the source temperature was maintained at 100° C. on the LCT (Time of Flight Zspray™ mass spectrometer from Waters. Nitrogen was used as the nebulizer gas. Data acquisition was performed with a Waters-Micromass MassLynx-Openlynx data system.

Method 1

In addition to the general procedure A: reversed phase UPLC was carried out on a Waters Acquity BEH (bridged ethylsiloxane/silica hybrid) C18 column (1.7 μm, 2.1×100 mm) with a flow rate of 0.35 ml/min. Two mobile phases (mobile phase A: 95% 7 mM ammonium acetate/5% acetonitrile; mobile phase B: 100% acetonitrile) were employed to run a gradient condition from 90% A and 10% B (hold for 0.5 minutes) to 8% A and 92% B in 3.5 minutes, hold for 2 min and back to the initial conditions in 0.5 min, hold for 1.5 minutes. An injection volume of 2 μl was used. Cone voltage was 20 V for positive and negative ionization mode. Mass spectra were acquired by scanning from 100 to 1000 in 0.2 seconds using an interscan delay of 0.1 seconds.

Method 2

In addition to the general procedure A: reversed phase UPLC was carried out on a Waters Acquity BEH (bridged ethylsiloxane/silica hybrid) C18 column (1.7 μm, 2.1×100 mm) with a flow rate of 0.343 ml/min. Two mobile phases (mobile phase A: 95% 7 mM ammonium acetate/5% acetonitrile; mobile phase B: 100% acetonitrile) were employed to run a gradient condition from 84.2% A and 15.8% B (hold for 0.49 minutes) to 10.5% A and 89.5% B in 2.18 minutes, hold for 1.94 min and back to the initial conditions in 0.73 min, hold for 0.73 minutes. An injection volume of 2 μl was used. Cone voltage was 20V for positive and negative ionization mode. Mass spectra were acquired by scanning from 100 to 1000 in 0.2 seconds using an interscan delay of 0.1 seconds.

Method 3

In addition to the general procedure B: reversed phase HPLC was carried out on a Waters X-bridge C18 column (3.5 µm, 4.6×100 mm) with a flow rate of 0.8 ml/min. Two mobile phases (mobile phase A: 100% 7 mM ammonium acetate; mobile phase B: 100% acetonitrile) were employed to run a gradient condition from 80% A and 20% B (hold for 0.5 minute) to 90% B in 4.5 minutes, 90% B for 4 minutes and reequilibrated with initial conditions for 3 minutes. An injection volume of 5 µl was used. Cone voltage was 20 V for positive and negative ionization mode. Mass spectra were acquired by scanning from 100 to 1000 in 0.4 seconds using an interscan delay of 0.3 seconds.

Method 4

In addition to the general procedure B: reversed phase HPLC was carried out on a Waters Atlantis C18 column (5 µm, 3.9×100 mm) with a flow rate of 0.8 ml/min. Three mobile phases (mobile phase A: 100% 7 mM ammonium acetate; mobile phase B: 100% acetonitrile; mobile phase C: 0.2% formic acid+99.8% ultra-pure water) were employed to run a gradient condition from 50% A and 50% C (hold for 1.5 minute) to 10% A, 80% B and 10% C in 4.5 minutes, hold for 4 minutes and reequilibrated with initial conditions for 3 minutes. An injection volume of 5 µl was used. Cone voltage was 20 V for positive and negative ionization mode. Mass spectra were acquired by scanning from 100 to 1000 in 0.4 seconds using an interscan delay of 0.3 seconds.

Method 5

The HPLC measurement was performed using an HPLC 1100/1200 (Agilent) system comprising a quaternary pump with degasser, an autosampler, a diode-array detector (DAD) and a column as specified in the respective methods below, the column is hold at room temperature. The MS detector (MS-Agilent simple quadripole) was configured with an electrospray-APCI ionization source. Nitrogen was used as the nebulizer gas. Data acquisition was performed with a Chemstation data system.

Reversed phase HPLC was carried out on a Nucleosil C18 column (3 µm, 3×150 mm) with a flow rate of 0.42 ml/min. Two mobile phases (mobile phase A: water/TFA (0.1%); mobile phase B: 100% acetonitrile) were employed to run a gradient condition from 98% A for 3 minutes, to 100% B in 12 minutes, 100% B for 5 minutes, then back to 98% A in 2 minutes, and reequilibrated with 98% A for 6 minutes. An injection volume of 2 µl was used. The capillary voltage was 2 kV, the corona discharge was held at 1 µA and the source temperature was maintained at 250° C. A variable voltage was used for the fragmentor. Mass spectra were acquired in electrospray ionization and APCI in positive mode, by scanning from 100 to 1100 amu.

TABLE C.1

LC/MS data

| Co. No. | Rt | MH+ | Method | Co. No. | Rt | MH+ | Method |
|---|---|---|---|---|---|---|---|
| 2 | 5.12 | 419 | 3 | 41 | 1.98 | 387 | 2 |
| 3 | 2.53 | 392 | 2 | 42 | 2.12 | 310 | 2 |
| 6 | 2.84 | 412 | 1 | 43 | 2.76 | 400 | 2 |
| 7 | 2.43 | 411 | 2 | 44 | 2.63 | 392 | 2 |
| 9 | 2.74 | 420 | 2 | 45 | 2.58 | 392 | 2 |
| 10 | 2.53 | 392 | 2 | 46 | 2.16 | 382 | 2 |
| 11 | 2.74 | 400 | 2 | 47 | 2.24 | 421 | 2 |
| 12 | 1.96 | 387 | 2 | 48 | 5.4 | 353 | 4 |
| 13 | 3.23 | 392 | 1 | 49 | 1.85 | 408 | 2 |
| 14 | 2.63 | 386 | 2 | 50 | 1.78 | 388 | 2 |
| 15 | 2.92 | 426 | 2 | 51 | 1.84 | 376 | 2 |
| 17 | 2.64 | 403 | 2 | 52 | 13.46 | 324 | 5 |
| 18 | 2.65 | 423 | 2 | 53 | 14.13 | 338 | 5 |
| 19 | 2.44 | 376 | 2 | 54 | 14.38 | 404 | 5 |
| 21 | 2.66 | 404 | 2 | 57 | 2.59 | 390 | 2 |
| 22 | 2.4 | 376 | 2 | 58 | 11.35 | 380 | 5 |

TABLE C.1-continued

LC/MS data

| Co. No. | Rt | MH+ | Method | Co. No. | Rt | MH+ | Method |
|---|---|---|---|---|---|---|---|
| 23 | 2.22 | 405 | 2 | 59 | 15.16 | 426 | 5 |
| 26 | 1.5 | 353 | 2 | 60 | 14.79 | 406 | 5 |
| 30 | 1.78 | 351 | 2 | 61 | 2.35 | 417 | 2 |
| 31 | 8.79 | 342 | 5 | 62 | 13.58 | 434 | 5 |
| 32 | 2.07 | 393 | 2 | 63 | 15.03 | 406 | 5 |
| 33 | 2.12 | 453 | 2 | 64 | 1.6 | 381 | 2 |
| 34 | 2.1 | 348 | 2 | 67 | 14.01 | 417 | 5 |
| 35 | 2.72 | 423 | 2 | 68 | 15.62 | 426 | 5 |
| 36 | 2.73 | 423 | 2 | 69 | 15.09 | 406 | 5 |
| 37 | 11.2 | 379 | 5 | 71 | 13.1 | 404 | 5 |
| 38 | 11.4 | 379 | 5 | 72 | 14.51 | 422 | 5 |
| 39 | 12.26 | 379 | 5 | 73 | 2.78 | 384 | 2 |
| 40 | 1.99 | 387 | 2 | | | | |

C2. Melting Points

For a number of compounds, melting points were obtained with a Kofler hot bench, consisting of a heated plate with linear temperature gradient, a sliding pointer and a temperature scale in degrees Celsius.

For a number of compounds, melting points were determined using differential scanning calorimetry (DSC). Melting points were measured with a temperature gradient of 10° C./minute starting at 25° C. Maximum temperature was 350° C.

For a number of compounds, melting points were obtained with a Büchi melting point apparatus B-560. The heating medium was a metal block. The melting of the sample was visually observed by a magnifying lense and a big light contrast. Melting points were measured with a temperature gradient of either 3 or 10° C./minute. Maximum temperature was 300° C.

The remaining melting points were determined using open capillary tubes.

TABLE C.2 melting point data

| Co. No. | Melting Moint | Method | Co. No. | Melting Moint | Method |
|---|---|---|---|---|---|
| 1 | 274.95° C. | DSC | 25 | 249.0-259.1° C. | Büchi |
| 2 | 218° C. | Kofler | 26 | 227° C. | Kofler |
| 3 | 259.80° C. | DSC | 30 | 243.45° C. | DSC |
| 4 | 122° C. | Kofler | 32 | 262° C. | Kofler |
| 5 | 128.6-129.8 | — | 33 | 267.48° C. | DSC |
| 6 | 270.49° C. | DSC | 34 | >250° C. | Kofler |
| 8 | 97-98° C. | — | 35 | >260° C. | Kofler |
| 9 | 178° C. | Kofler | 36 | 150° C. | Kofler |
| 10 | 244° C. | Kofler | 40 | 268.40° C. | DSC |
| 11 | 178° C. | Kofler | 41 | 273.08° C. | DSC |
| 13 | 130° C. | Kofler | 42 | 232° C. | Kofler |
| 14 | 269.15° C. | DSC | 43 | 227° C. | Kofler |
| 15 | 246° C. | Kofler | 44 | 262.20° C. | DSC |
| 16 | 247.3-248.5° C. | — | 45 | 258.89° C. | DSC |
| 17 | 128° C. | Kofler | 46 | 224.32° C. | DSC |
| 18 | 123° C. | Kofler | 47 | 273.86° C. | DSC |
| 19 | 135° C. | Kofler | 48 | >260° C. | Kofler |
| 21 | 218° C. | Kofler | 52 | >260° C. | Kofler |
| 22 | 198° C. | Kofler | 61 | 252° C. | Kofler |
| 24 | 238.1-249.2° C. | Büchi | 64 | >265° C. | Kofler |

D. Pharmacological Examples

D.1 FabI Enzyme Inhibition

*Staphylococcus aureus* FabI Enzyme Inhibition Assay

FabI enzyme inhibition assays were carried out in half-area, 384-well microtitre plates. Compounds were evaluated in 40-μl assay mixtures containing 100 mM NaADA, pH 6.5 (ADA=N-[2-acetamido]-2iminodiacetic acid), 250 μM crotonoyl-CoA, 625 μM NADH and 50 μg/ml *S. aureus* ATCC 29213 FabI. Inhibitors were typically varied over the range of 50 to 0.39 μM. The reaction mixtures were incubated for 30 minutes at room temperature and the reaction was stopped by adding 200 mM Tris buffer (pH 9.0) to create a pH-shift. The consumption of NADH was monitored by measuring the change in absorbance at 340. By comparing sample readings to those of negative (absence of compound) and positive (absence of enzyme) controls, the percent inhibition of enzymatic activity of the compounds was determined. A best-fit curve is fitted by a minimum of squares method. From this an $IC_{50}$-value (expressed in μg/ml), resulting in 50% inhibition of enzymatic activity, was obtained.

TABLE D.1

*S. aureus* FabI $IC_{50}$ values

| Co. No. | FabI $IC_{50}$ μg/mL |
|---|---|
| 1 | 0.32 |
| 2 | 0.78 |
| 3 | 0.29 |
| 4 | 0.70 |
| 5 | ~0.6 |
| 6 | 3.73 |
| 8 | 0.50 |
| 9 | 0.75 |
| 10 | 0.53 |
| 11 | 0.48 |
| 12 | 0.44 |
| 13 | 0.39 |
| 14 | 0.40 |
| 15 | 0.48 |
| 17 | 0.38 |
| 18 | 0.44 |
| 19 | ~0.62 |
| 20 | 1.07 |
| 21 | 0.65 |
| 22 | 0.58 |
| 23 | 0.41 |
| 24 | 0.58 |
| 25 | 0.51 |
| 26 | 0.41 |
| 27 | 0.6 |
| 29 | 1.04 |
| 30 | 2.66 |
| 31 | 1.42 |
| 32 | 0.46 |
| 33 | 3.06 |
| 34 | 1.67 |
| 35 | 1.25 |
| 36 | 0.93 |
| 37 | 3.37 |
| 38 | 2.08 |
| 39 | 0.56 |
| 40 | 0.39 |
| 41 | 0.44 |
| 42 | 0.83 |
| 43 | 0.60 |
| 44 | 0.46 |
| 45 | 0.45 |
| 46 | 0.54 |

TABLE D.1-continued

*S. aureus* FabI $IC_{50}$ values

| Co. No. | FabI $IC_{50}$ μg/mL |
|---|---|
| 47 | 0.43 |
| 48 | 2.93 |
| 49 | 0.44 |
| 51 | 0.54 |
| 52 | 0.50 |
| 53 | 0.36 |
| 54 | 1.84 |
| 57 | 0.62 |
| 59 | 0.76 |
| 60 | 0.59 |
| 61 | 0.54 |
| 62 | 0.44 |
| 63 | 0.63 |
| 64 | 1.62 |
| 67 | 0.63 |
| 68 | 0.99 |
| 71 | 2.55 |
| 72 | 0.43 |
| 73 | 0.80 |

D.2 In Vitro Method for Testing Compounds for Antibacterial Activity Against Various Bacterial Strains Preparation of Bacterial Suspensions for Susceptibility Testing The following bacteria were used: *Staphylococcus aureus* ATCC 29213, methicillin-resistant *Staphylococcus aureus* (MRSA) ATCC 700788 and *Escherichia coli* ATCC 35218. The bacteria used in this study were grown overnight in flasks containing 100 ml Mueller-Hinton broth (Difco cat. nr. 0757-17) in sterile de-ionized water, with shaking, at 37° C. Stocks were store at −70° C. until use.

Bacteria were incubated on a tryptic soy agar plate containing 5% sheep blood (Becton Dickinson cat. nr. 254053) for 18-24 hours at 35° C. in aerobic conditions (first passage). For the second passage, fresh Mueller-Hinton broth is inoculated with 5-10 colonies and grown overnight at 35° C. until turbidity (reaching log-phase) in aerobic conditions is reached. The bacterial suspension is then adjusted to 0.5 McFarland density and further diluted 1:100 in Mueller Hinton broth medium. This is used as inoculum.

The results (for STA ATCC 29213) are depicted in the table D2 below.

Antibacterial Susceptibility Testing: $IC_{90}$ Determination

MIC assays were performed by the broth microdilution method in a 96-well format (flat-bottom microtitre plates) with a final volume of 0.1 ml Mueller Hinton broth containing two-fold serial dilutions of compounds and inoculated with $5 \times 10^5$ CFU/ml of bacteria (standard inoculum size according to CLSI guidelines). Inhibitors are typically varied over the range of 63 to 0.49 μM. The final DMSO concentration in the assay was 1.25% (maximum tolerable DMSO concentration=6%). In the assays where the effect of human serum on the activity of the compounds against *S. aureus* was tested, human serum was added at a final concentration of 10%. The plates were incubated at 35° C. for 16-20 hours. At the end of incubation the bacterial growth was quantified fluorometrically. For this, resazurin was added to all wells and the plates were re-incubated. The incubation time is dependent on the type of bacteria. A change in color from blue to pink indicated the growth of bacteria. The fluorescence was read in computer-controlled fluorometer (Fluoroskan Ascent FL, Labsystems) at an excitation wavelength 540 nm and an emission wavelength of 590 nm. The % growth inhibition achieved by the compounds was calculated according to standard methods. The $IC_{90}$ (expressed in μg/ml) was defined as the 90% inhibitory concentration for bacterial growth. A panel of reference compounds were simultaneously tested for QC approval.

The results are depicted in the table D2 below (STA+10% HS).

Cytotoxicity Assays

Cytotoxicity of the compounds was evaluated using the MTT assay. Human HelaM cells grown in 96-well plates were exposed to serial dilutions of the tested compounds (final volume of 0.2 ml) and incubated for 72 hours at 37° C. and 5% $CO_2$. Inhibitors are typically varied over the range of 25 to 0.8 μM. The final DMSO concentration in the assay is 0.5%. MTT (3-(4,5-Dimethylthiazol-2-yl)-2,5-diphenyltetrazolium bromide, a tetrazole) was added and reduced to purple formazan only in living cells. Solubilization of the formazan crystals was achieved by adding 100 μl 2-propanol. Cell viability was determined by measuring the absorbance of the reduced formazan, giving a purple color, at 540 nm and 690 nm. The absorbance measured at 690 nm was automatically subtracted from the absorbance at 540 nm, to eliminate the effects of non-specific absorption. The percent cytotoxicity achieved by the compounds was calculated according to standard methods. Cytotoxicity is reported as $CC_{50}$, the concentration that causes a 50% reduction in cell viability.

The results are depicted in the table D2 below (TOX HELAM).

TABLE D2 data for representative examples

| Cpd. No. | STA (361.159) IC90 μg/mL | STA + 10% HS (361.169) IC90 μg/mL | TOX HELAM (222.125) CC50 μg/mL |
| --- | --- | --- | --- |
| 1 | 0.09 | 0.17 | >3.8547 |
| 2 | 1.02 | 1.09 | >19.4696 |
| 3 | 0.03 | 0.06 | >3.25636 |
| 5 | 0.64 | 1.14 | 7.92 |
| 8 | 1.15 | 1.52 | >10.5122 |
| 9 | 0.33 | 0.69 | 4.77 |
| 10 | 0.08 | 0.13 | >3.915 |
| 11 | 0.37 | 1.76 | 6.19 |
| 12 | 0.33 | 0.53 | >9.70744 |
| 13 | 0.31 | 0.43 | >9.68257 |
| 14 | 0.19 | 0.19 | >9.68257 |
| 15 | 0.74 | 0.72 | >9.78279 |
| 17 | 0.37 | 0.38 | >10.1103 |
| 18 | 0.21 | 0.37 | >10.6233 |
| 19 | 0.18 | 0.12 | >9.43038 |
| 21 | 0.13 | 0.29 | >4.0346 |
| 22 | 0.23 | 0.25 | >9.43038 |
| 23 | 0.67 | 0.79 | >10.3108 |
| 24 | 4.05 | 2.44 | >3.9549 |
| 26 | 1.11 | 1.11 | >3.8646 |

Example E

E.1 Thermodynamic Solubility/Solubility in Aqueous Solution

The pH solubility profiling was carried out at ambient temperature for a period of 4 days. A saturation solubility study was carried out in order to determine maximum solubility in a particular buffer solution. The compound was added to respective buffer solution until saturation point is reached. This was followed by shaking the flask for 4 days at ambient temperature. After 4 days, the solutions were filtered and injected on UPLC and the concentration was determined using a generic HPLC method.

Results

| | Co. No. 14 | Co. No. 1 | Co. No. 41 | Co. No. 2 |
| --- | --- | --- | --- | --- |
| Buffer pH 2 | <0.01 | <0.002 | 1.18 | <0.01 |
| 10% HP-β-CD buffer pH 2 | 0.076 | NT | NT | NT |
| 20% HP-β-CD buffer pH 2 | 0.20 | NT | NT | NT |
| Buffer pH 4 | <0.01 | <0.002 | <0.01 | <0.01 |
| 10% HP-β-CD buffer pH 4 | 0.069 | 0.177 | 1.1 | 0.11 |
| 20% HP-β-CD buffer pH 4 | 0.18 | 0.308 | >1.15 | 0.28 |
| Buffer pH 7.4 | <0.01 | <0.002 | 0.13 | <0.01 |
| 10% HP-β-CD buffer pH 7.4 | 0.089 | 0.100 | 0.49 | 0.14 |
| 20% HP-β-CD buffer pH 7.4 | 0.20 | 0.417 | 0.56 | 0.33 |

NT = not tested

E.2 Antimicrobial Spectrum of Activity

Minimum Inhibitory Concentrations (MICs) were determined in accordance with the Clinical and Laboratory Standards Institute (CLSI) methodology against aerobic bacteria (CLSI M07-A8) (see Clinical and Laboratory Standards Institute. 2009. Methods for dilution antimicrobial susceptibility tests for bacteria that grow aerobically. CLSI document M07-A8, Vol. 29, No. 2.) by the broth microdilution method with cation-adjusted Mueller-Hinton broth (CA-MHB) medium for the majority of organisms, except for *Haemophilus influenza*, where Haemophilis test medium (HTM) broth was used. Descriptions of the individual organisms can be found in the table. Where possible, ATCC standard strains were tested.

The inoculum density for the susceptibility testing was standardized to give a final inoculum of approximately $5 \times 10^5$ CFU/mL. The broth MIC was determined as the lowest concentration of drug that prevented visible growth after 16-24 hours (species dependent) of incubation at 35° C.-37° C.

TABLE

Description of individual organisms tested

| Organism | Characteristics | MIC test medium |
| --- | --- | --- |
| *Staphylococcus aureus* | ATCC 29213; reference strain MSSA | MHB |
| *Staphylococcus aureus* | ATCC 43300; reference strain MRSA | MHB |
| *Staphylococcus aureus* | NRS119; LZD-R; SCCmec IV; origin: US | MHB |
| *Staphylococcus aureus* | NRS120; LZD-R; SCCmec IV; origin: US | MHB |
| *Staphylococcus aureus* | NRS121; LZD-R; SCCmec IV; origin: US | MHB |
| *Escherichia coli* | ATCC 25922; reference strain | MHB |

TABLE-continued

| Description of individual organisms tested | | |
|---|---|---|
| Organism | Characteristics | MIC test medium |
| *Escherichia coli* | Tol C mutant | MHB |
| *Haemophilus influenzae* | ATCC 49247; reference strain | HTM broth |
| *Moraxella catarrhalis* | ATCC 8176; b-lactamase negative | MHB |

Stock solutions of the compounds were prepared in DMSO at concentrations of 1 mg/mL. Linezolid was prepared in DMSO at a concentration of 2 mg/mL. Stock solutions of all compounds were diluted into CA-MHB to give a range of two-fold dilutions, depending upon the sensitivity of the organism being tested.

Results (where Available)

| | Compound Nos. and $MIC_{90}$ (µg/ml) | | | | | | | |
|---|---|---|---|---|---|---|---|---|
| Organism | 14 | 1 | 44 | 2 | 41 | 10 | 22 | 12 |
| *S. aureus* ATCC 29213 | 0.03 | 0.016 | 0.03 | 0.25 | 0.03 | 0.015 | 0.06 | 0.125 |
| *S. aureus* ATCC 43300 | 0.03 | 0.016 | 0.03 | 0.5 | 0.03 | 0.03 | 0.125 | 0.125 |
| *S. aureus* NRS119 | 0.03 | 0.03 | 0.03 | | 0.06 | | | |
| *S. aureus* NRS120 | 0.03 | 0.016 | 0.03 | | 0.06 | | | |
| *S. aureus* NRS121 | 0.03 | 0.016 | 0.06 | | 0.06 | | | |
| *E. coli* tolC mutant | 0.25 | ≤0.03 | >8 | 0.25 | 1 | 0.125 | 1 | 0.25 |
| *E. coli* ATCC 25922 | 4 | >32 | >8 | >8 | 8 | >8 | >8 | >8 |
| *H. influenza* ATCC 49247 | 0.25 | | >8 | >8 | 0.5 | >8 | 4 | 1 |
| *M. catarrhalis* ATCC 8176 | 0.015 | | 0.25 | | 0.12 | | | |

E.3 In Vivo Pharmacokinetic and Oral Bioavailability

The in vivo pharmacokinetics and oral bioavailability of the compound of the examples was/is investigated in male Swiss mice (fed) following single intravenous (i.v.) bolus and oral (p.o.) administration. For the i.v. and p.o. solution formulations, the compound was/is dissolved in a 20% HP-β-CD solution. The pH of the formulations was/is around pH 4. All i.v. formulations were isotonic.

Results

| | Co. No. 14 | Co. No. 1 | Co. No. 10 | Co. No. 44 | Co. No. 12 |
|---|---|---|---|---|---|
| | i.v. | | | | |
| Dose (mg/kg) | 2.5 | 2.5 | 2.5 | 2.5 | 2.5 |
| n | 3 | 3 | 3 | 3 | 3 |
| $C_0$ (ng/mL) | 2929 | 2921 | 4154 | 4524 | 2333 |
| Plasma clearance Cl (L/h/kg) | 0.33 | 0.35 | 0.64 | 0.49 | 2.2 |
| $Vd_z$ (L/kg) | 1.3 | 1.5 | 1.2 | 0.9 | 3.7 |
| $AUC_{0\text{-}inf}$ (ng · h/mL) | 7464 | 7074 | 3992 | 5037 | 1124 |
| Half life $(t_{1/2})$ (h) | 2.7 | 2.9 | 1.3 | 1.3 | 1.1 |
| | p.o. | | | | |
| Dose (mg/kg) | 10 | 5 | 10 | 10 | 10 |
| n | 3 | 3 | 3 | 3 | 3 |
| $C_{max}$ (ng/mL) | 2950 | 1720 | 3537 | 2670 | 275 |
| $T_{max}$ (h) | 2.0 | 2.0 | 1.0 | 1.0 | 1.0 |
| $AUC_{0\text{-}inf}$ (ng · h/mL) | 21394 | 12158 | 12376 | 14527 | 914 $AUC_{0\text{-}last}$ |
| Half life $(t_{1/2})$ (h) | 3.2 | 3.1 | 2.2 | 2.8 | n.d. |
| Oral bio-availability (%) | 72 | 86 | 81 | 59 | 21 |

E.4 In Vivo Efficacy

The concept of studying the in vivo effect of an antibacterial compound by treating intraperitoneally infected mice was introduced in 1911 for optochin against pneumococci (Morgenroth and Levy, 1911). The popularity of the model comes from the ease of its use with short-duration experiments, reproducible infections and simple end-points.

Method

Methicillin-sensitive *Staphylococcus aureus* strain ATCC 29213 was used to infect female Swiss albino mice. A Brain Heart Infusion (BHI) broth bacterial culture was inoculated the day before infection, incubated at 37° C. overnight and diluted in fresh BHI broth to the desired concentration. I.p. injection of ~5×10$^8$-5×10$^9$ colony forming units (CFU) was performed in either of the lateral lower quadrants of the abdomen. After inoculation, mice were kept in their cages under daily observation for development of signs of infection or death. For the treatment of mice, both the p.o. and i.v. routes were used and each mouse was treated individually by gavage or by i.v. injection. Both solutions (p.o. and i.v.) and suspensions (p.o.) were tested in this model. The parameter used for monitoring the course of infection and the effect of treatment was death or survival of the animals over 3 days post-infection. As death could also be due to toxic side effects, a non-infected control group of 3 mice, treated with the highest dose of the compound (in the studies where suspensions were used) tested, was included.

Results

In vivo antibacterial activity in peritonitis model of *S. aureus* infection (ATCC 29213) after oral and i.v. dosing using solutions

| Compound | Infection Route | Inoculum (log10) | Formulation | Treatment Route | Treatment Dose (mpk) | % Survival |
|---|---|---|---|---|---|---|
| 44 | IP | 8.9 | Sol 20% CD + 1HCl | PO, QD | 1; 5 | 57; 100 |
| 14 | IP | 8.7 | 20% CD + 2H2T | IV, QD | 2.5; 5 | 75; 100 |

Control mice exhibited 80% and 100% mortality, in each respective test.

The invention claimed is:

1. A compound selected from the group consisting of:

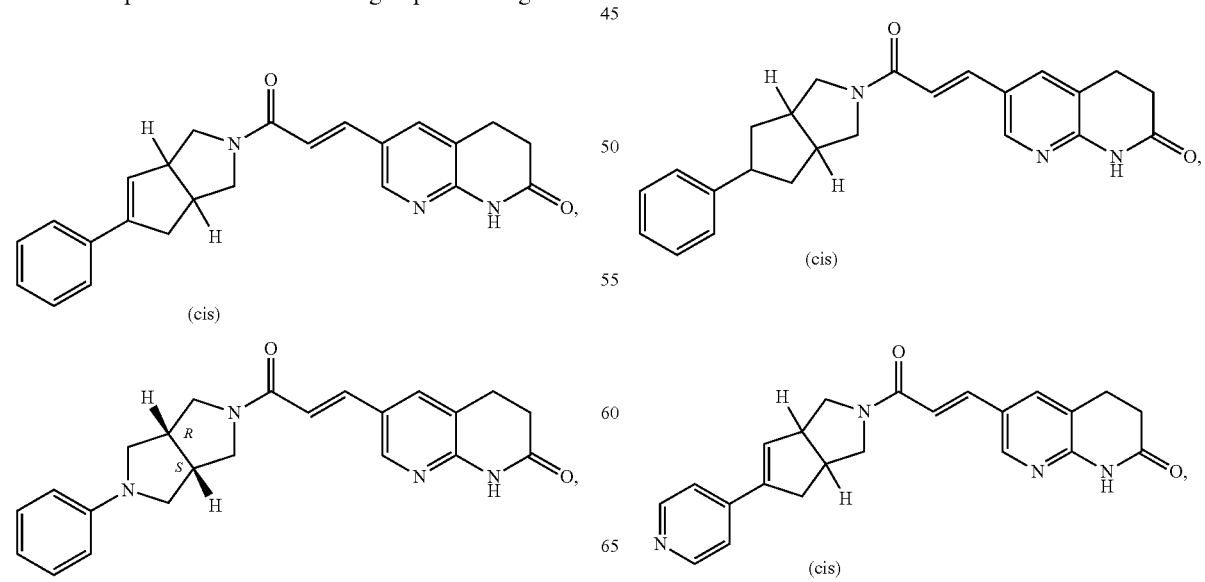

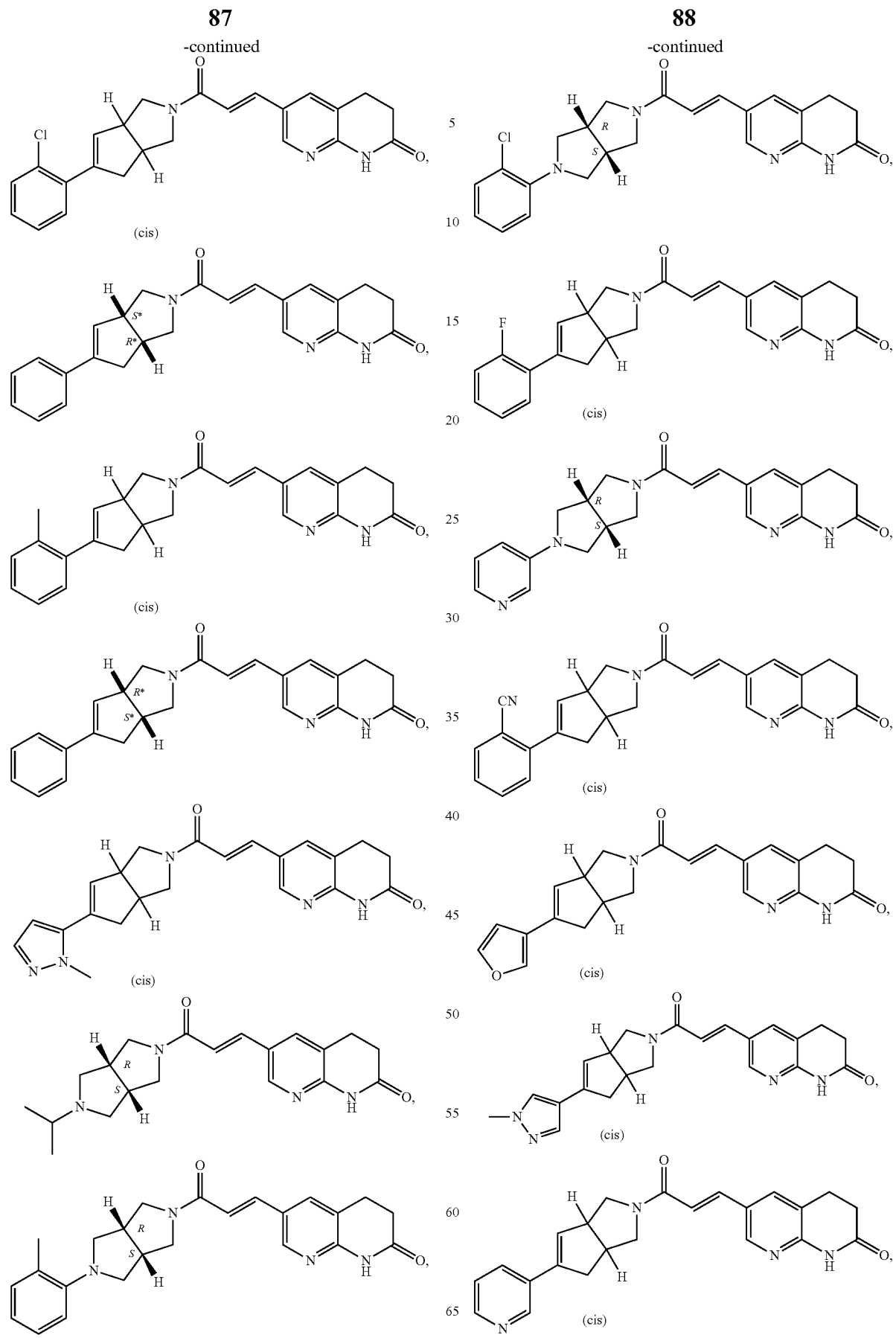

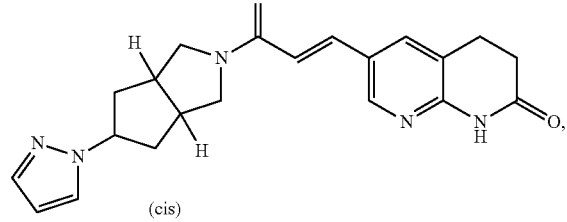
(cis)
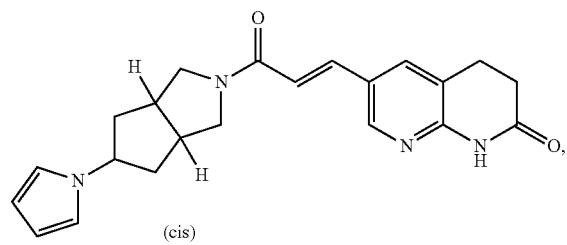
(cis)
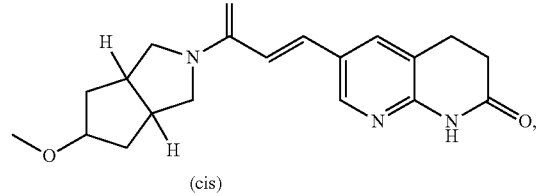
(cis)
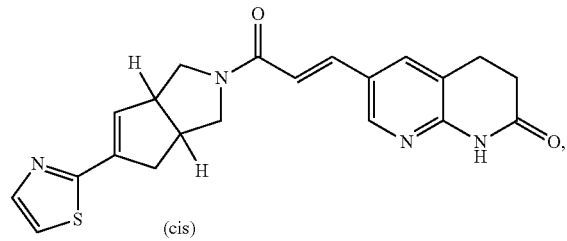
(cis)
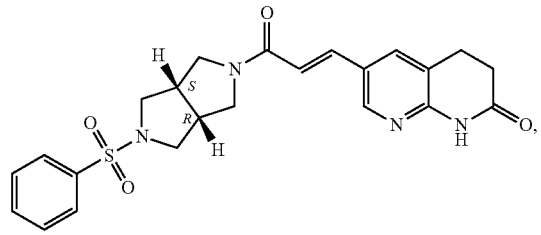
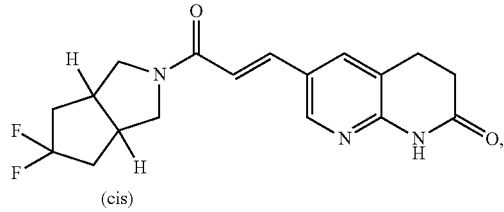
(cis)
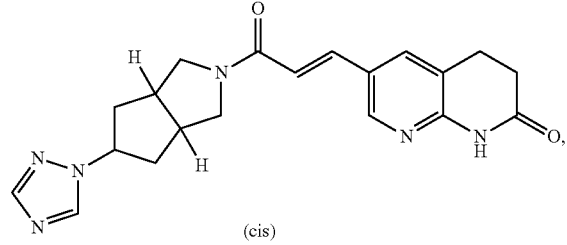
(cis)
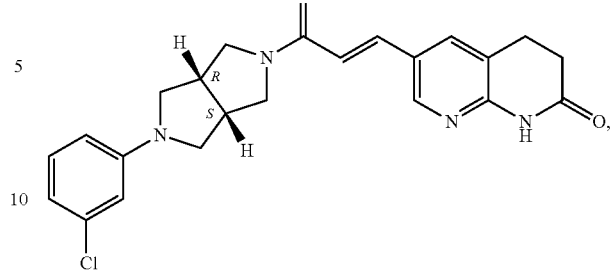
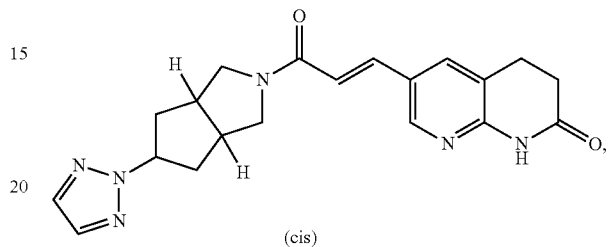
(cis)
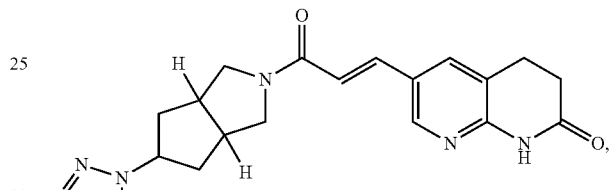
(cis)
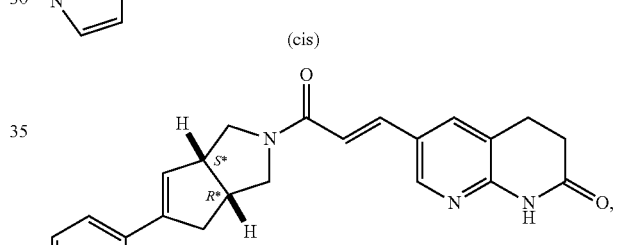
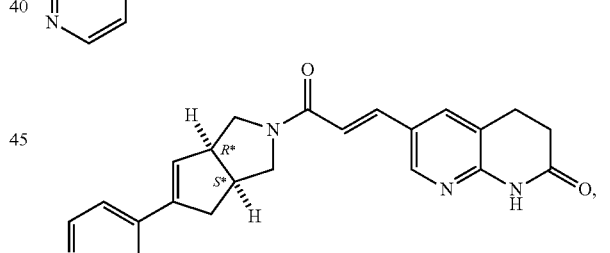
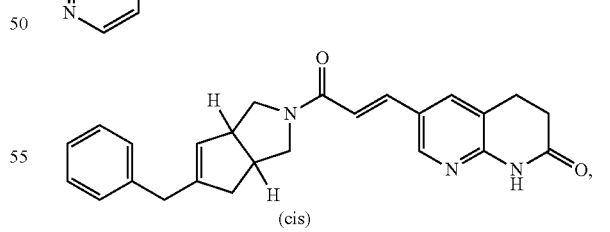
(cis)
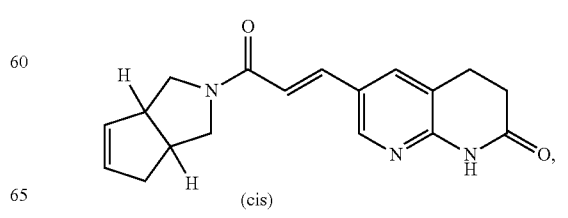
(cis)

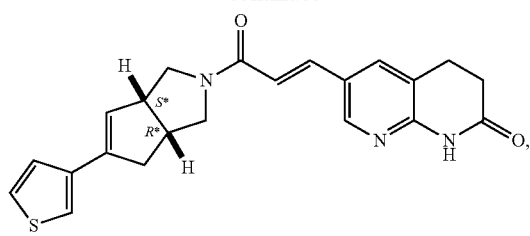
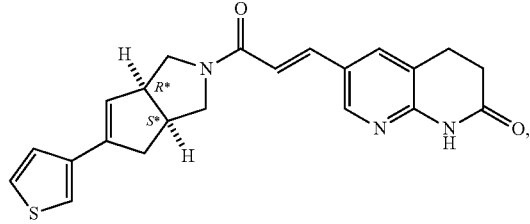
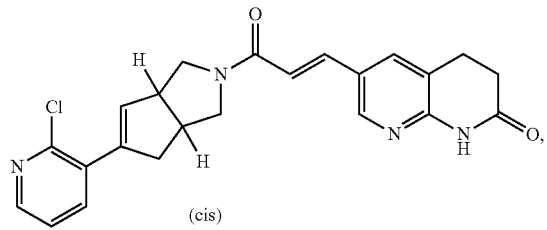
(cis)
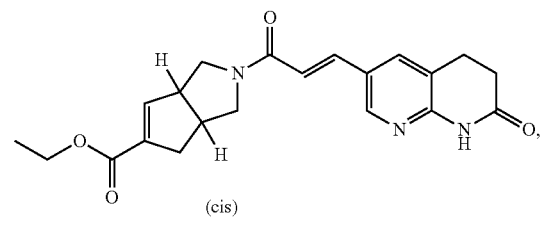
(cis)
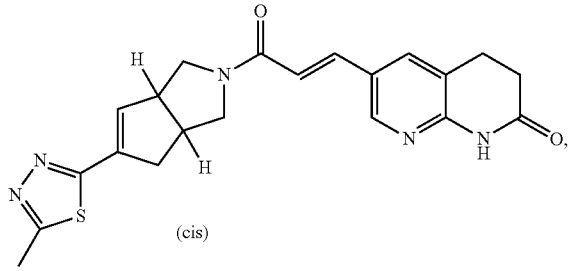
(cis)
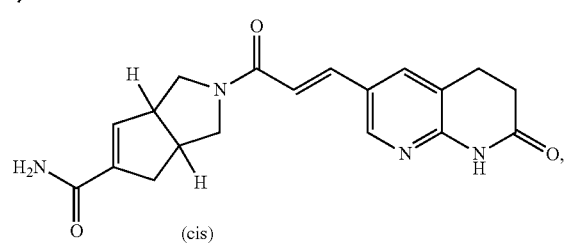
(cis)
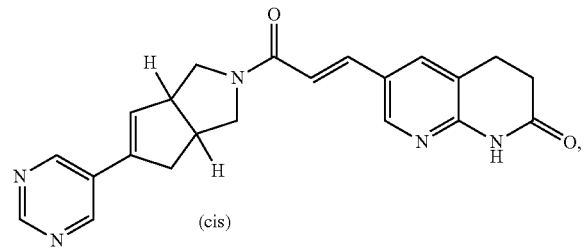
(cis)
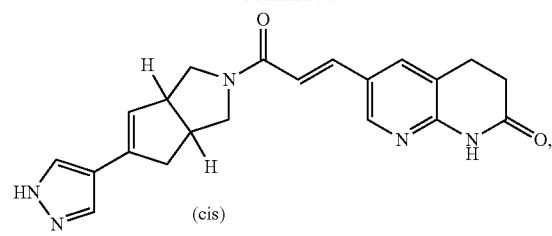
(cis)
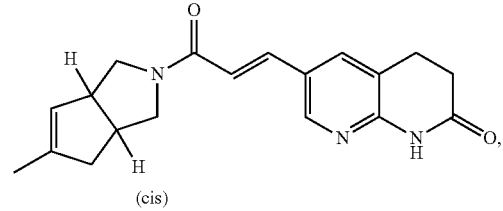
(cis)
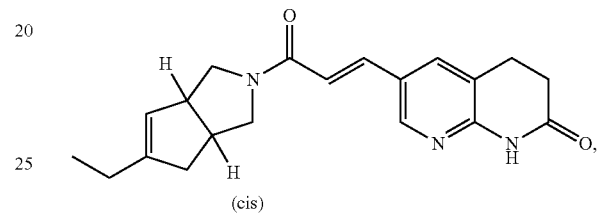
(cis)
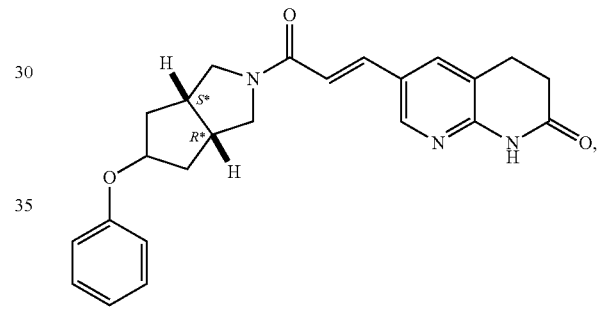
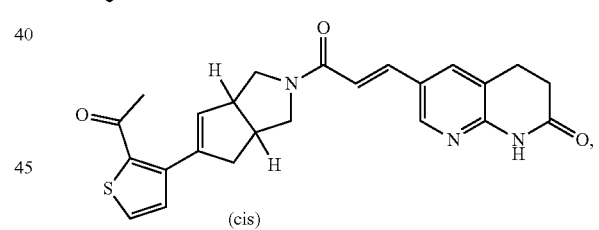
(cis)
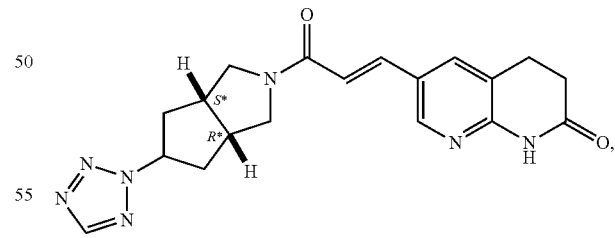
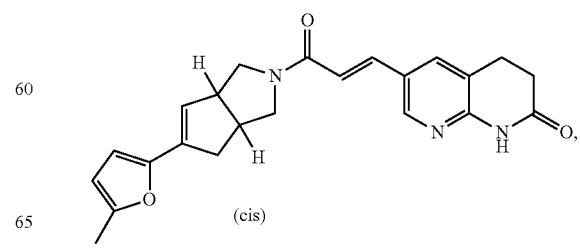
(cis)

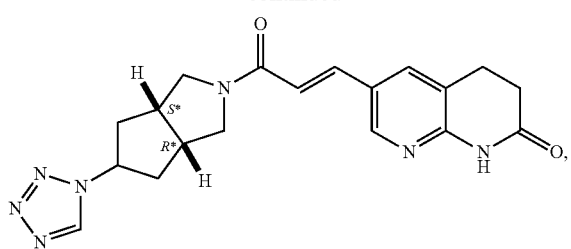
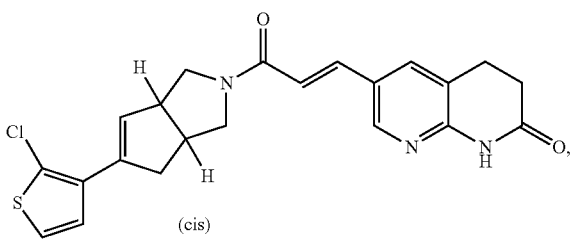
(cis)
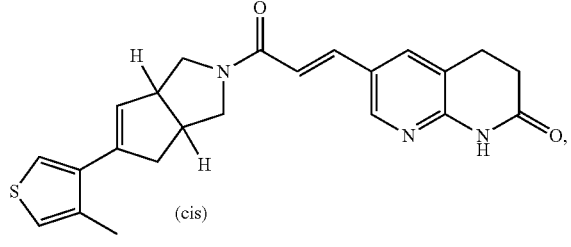
(cis)
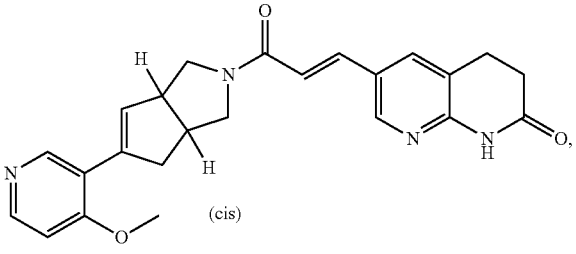
(cis)
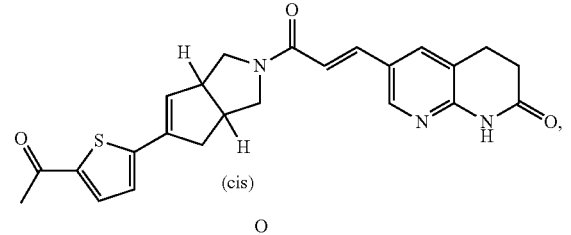
(cis)
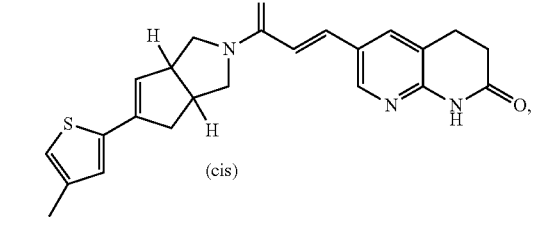
(cis)
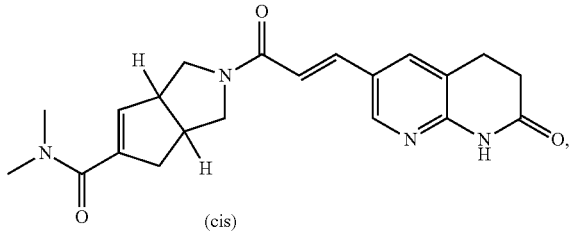
(cis)
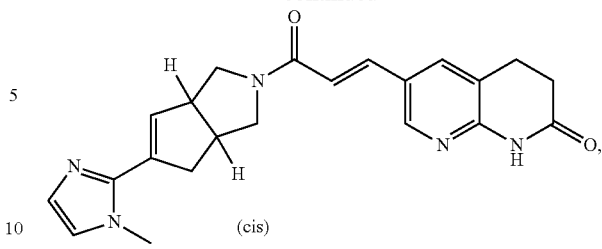
(cis)
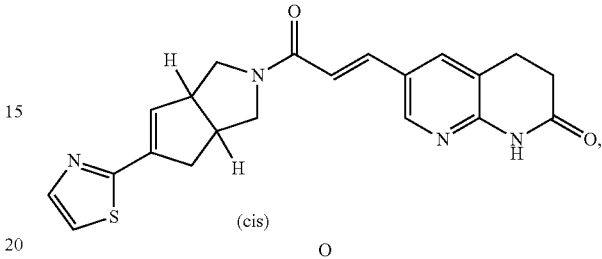
(cis)
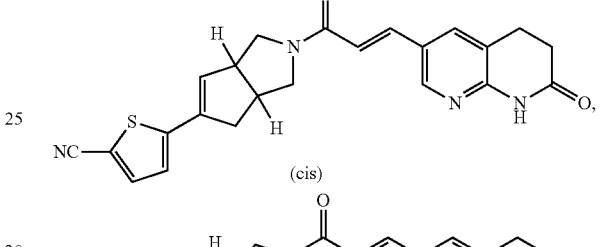
(cis)
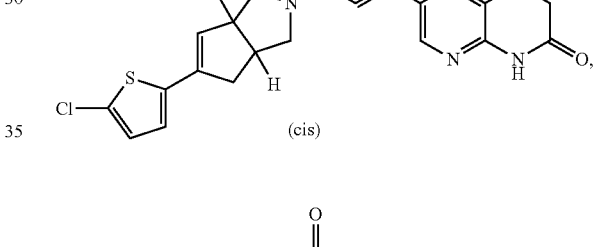
(cis)
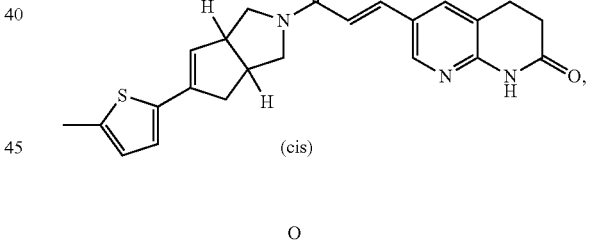
(cis)
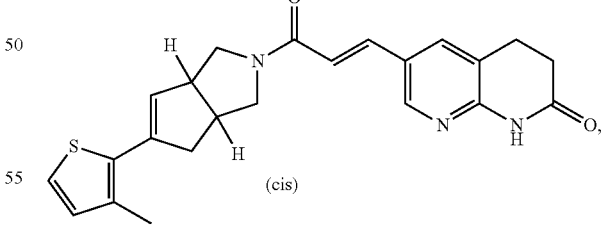
(cis)
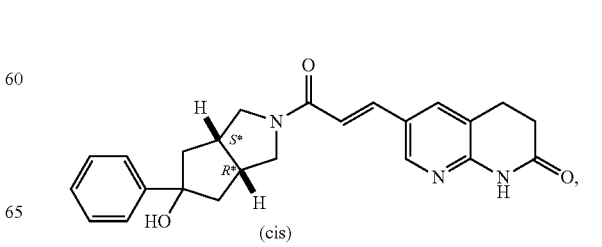
(cis)

-continued
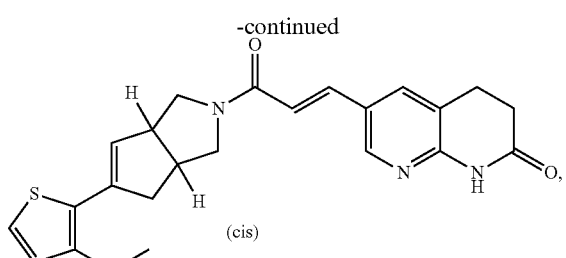
(cis)
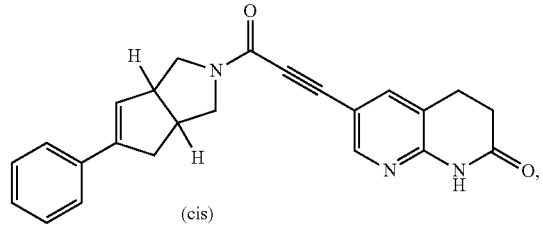 [SMILES: O=C1CCc2cc(C#CC(=O)N3CC4C=C(c5ccccc5)CC4C3)cnc2N1]
(cis)
and pharmaceutically acceptable salts thereof.
2. A pharmaceutical composition comprising a pharmaceutically acceptable excipient and an effective amount of a compound selected from the group consisting of:
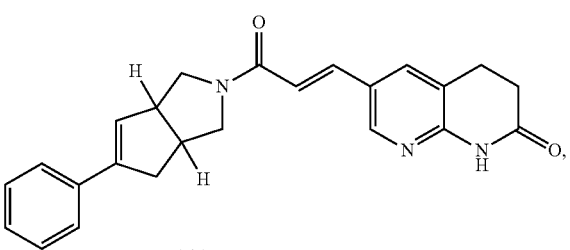
(cis)
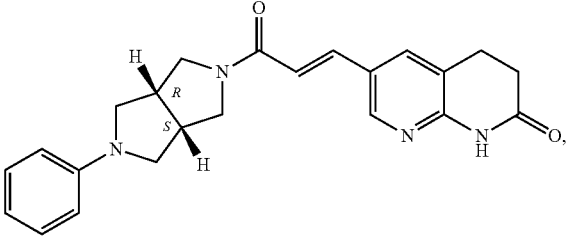
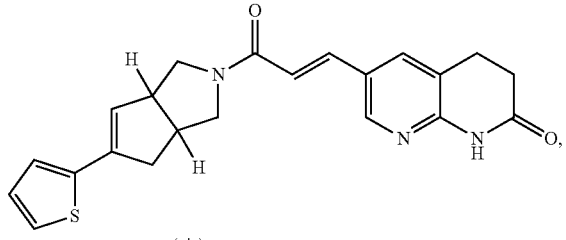
(cis)
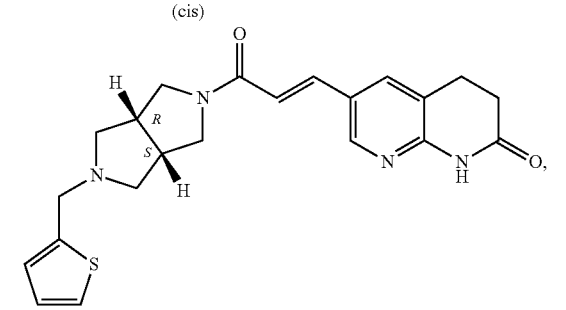
-continued
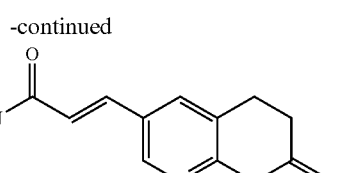
(cis)
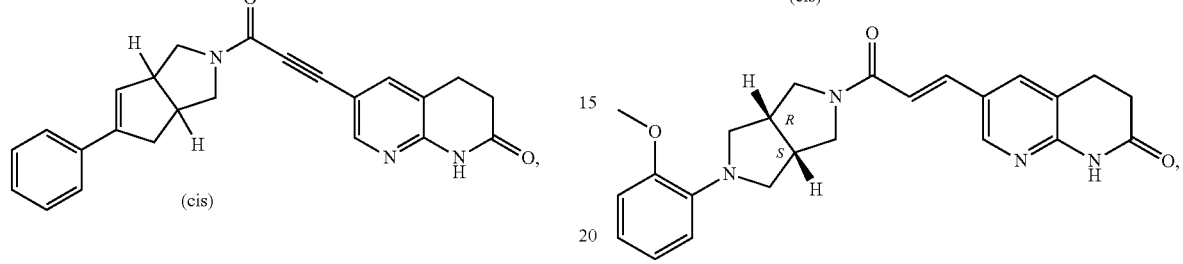
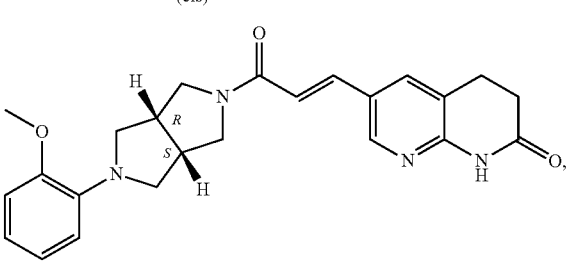
(cis)
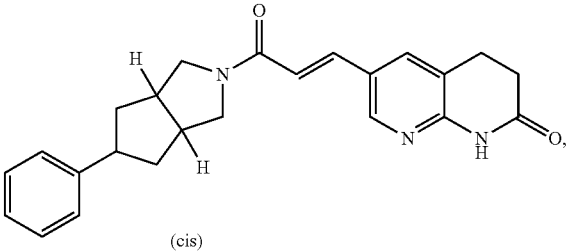
(cis)
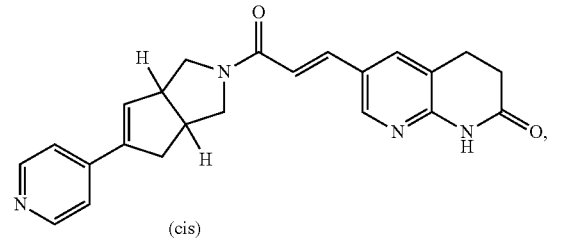
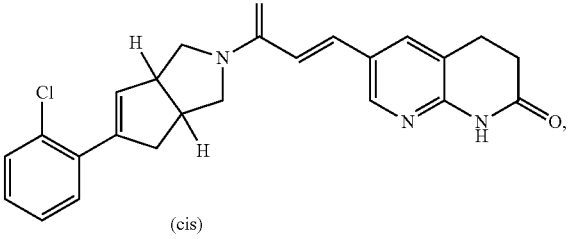
(cis)
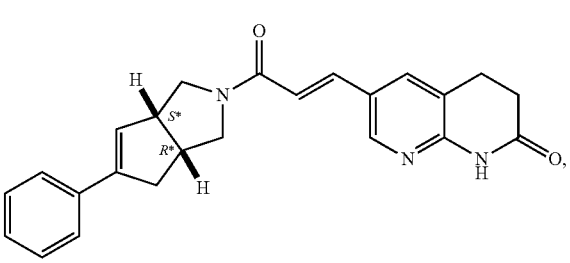

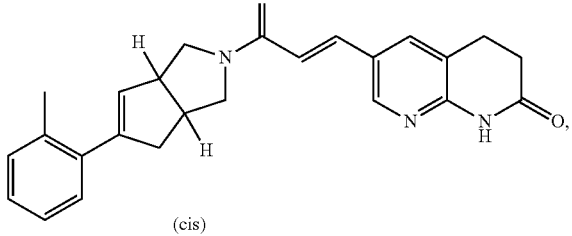
(cis)
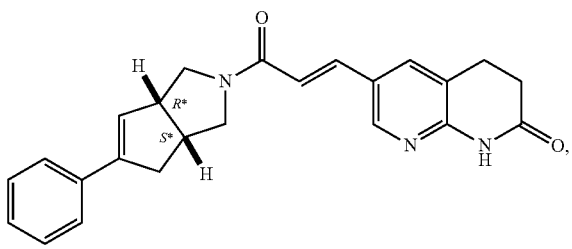
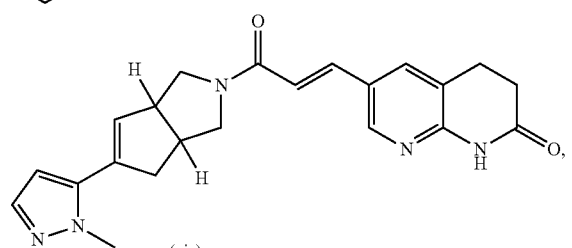
(cis)
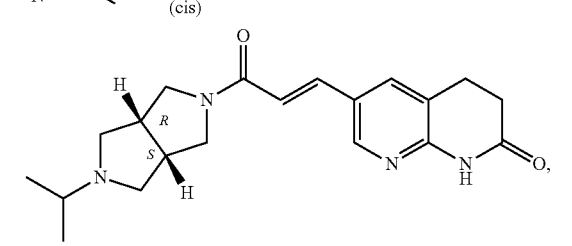
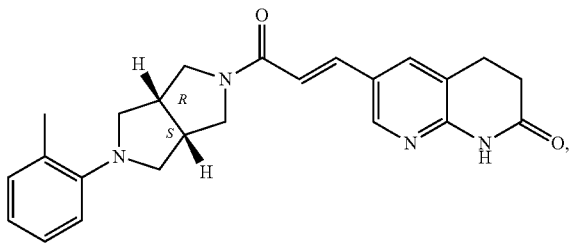
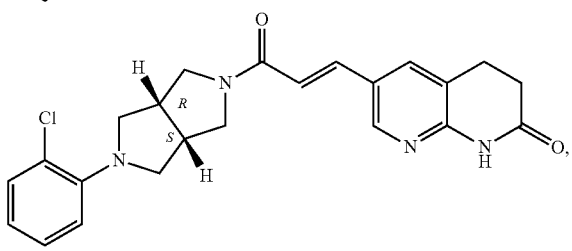
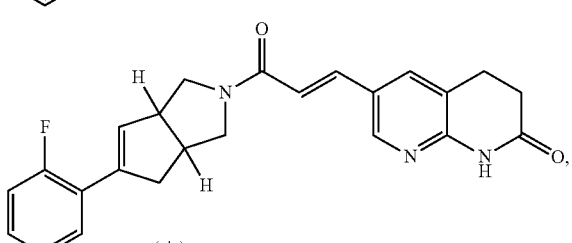
(cis)
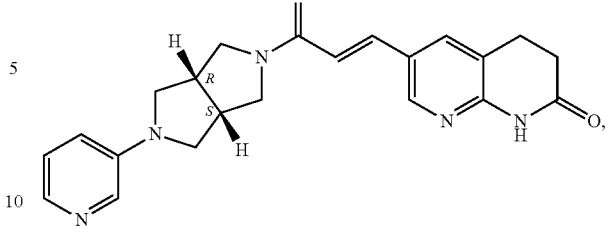
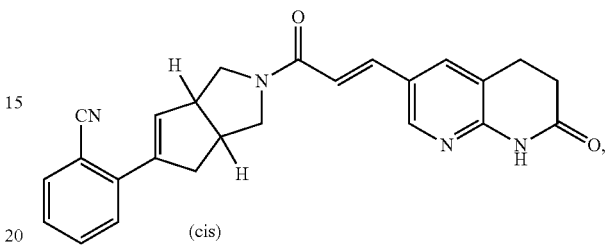
(cis)
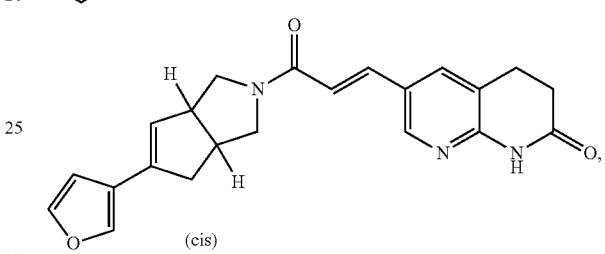
(cis)
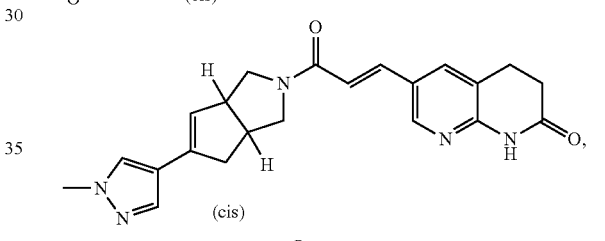
(cis)
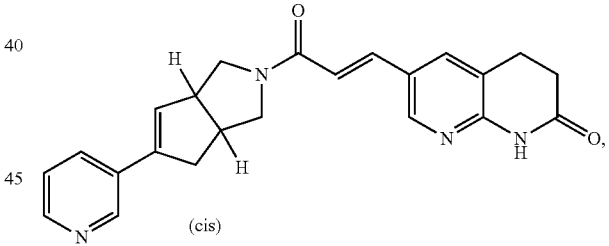
(cis)
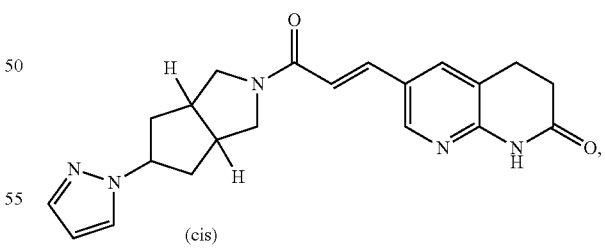
(cis)
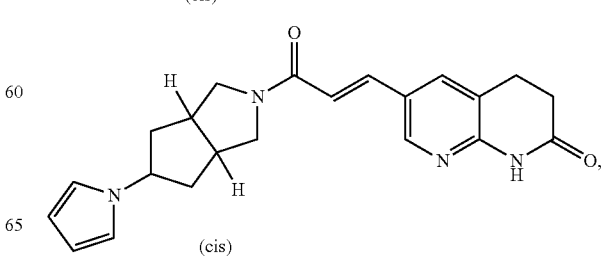
(cis)

99
-continued
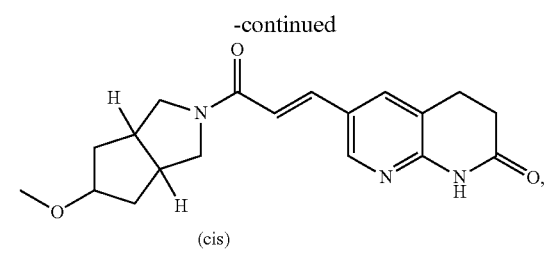
(cis)
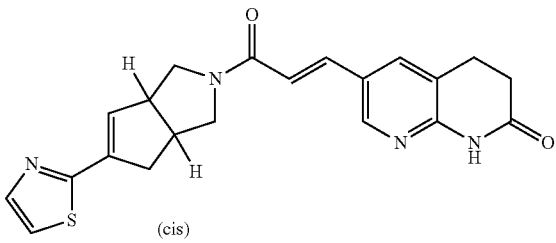
(cis)
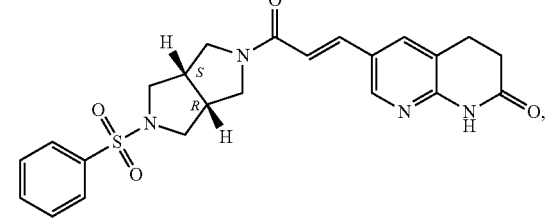
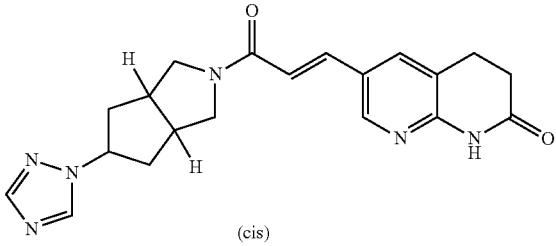
(cis)
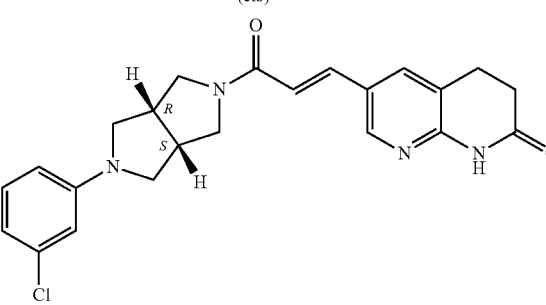
(cis)
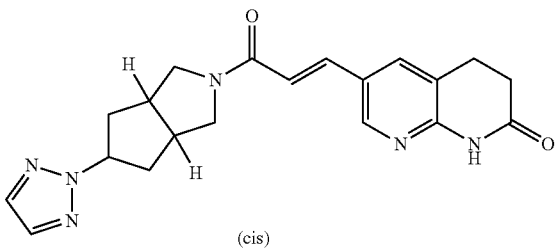
(cis)
100
-continued
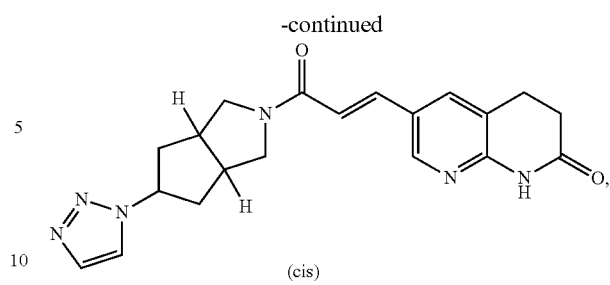
(cis)
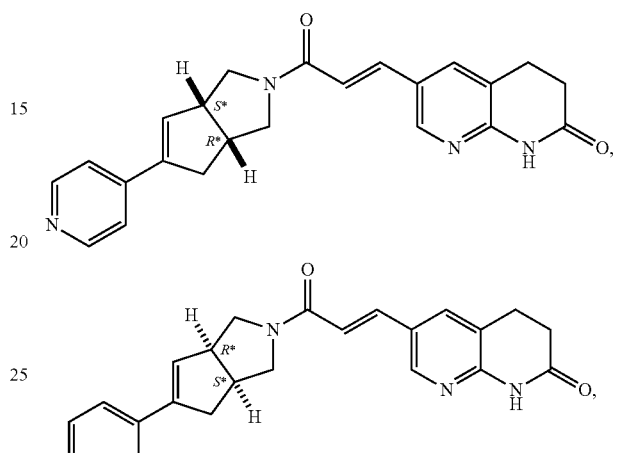
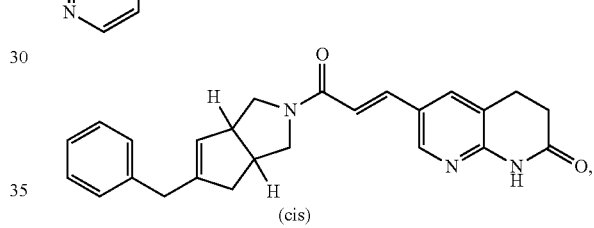
(cis)
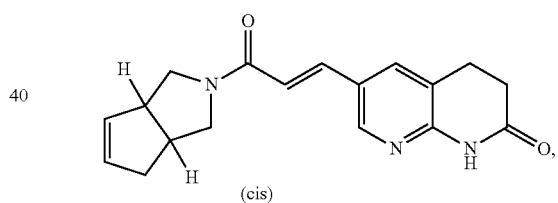
(cis)
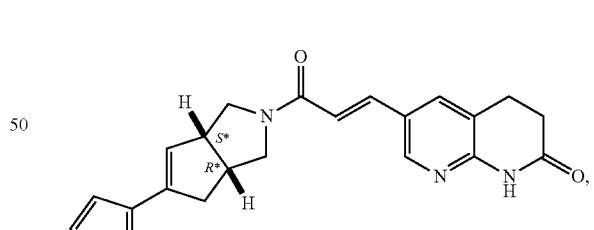
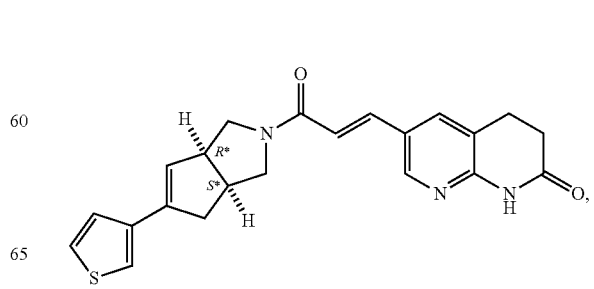

-continued
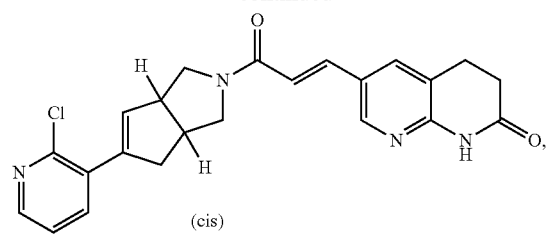
(cis)
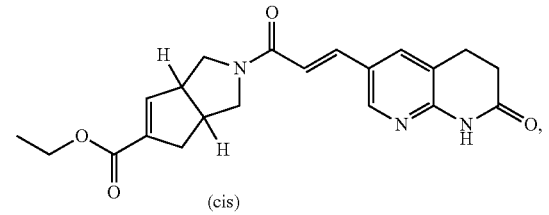
(cis)
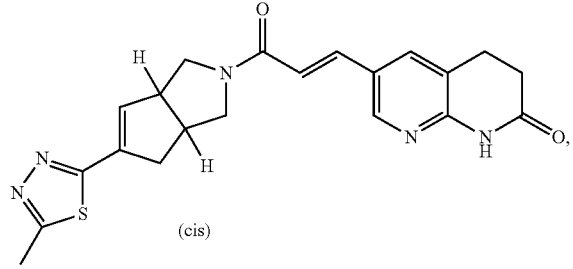
(cis)
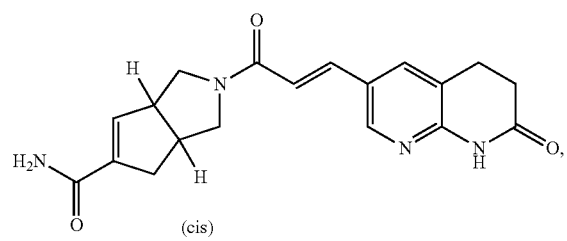
(cis)
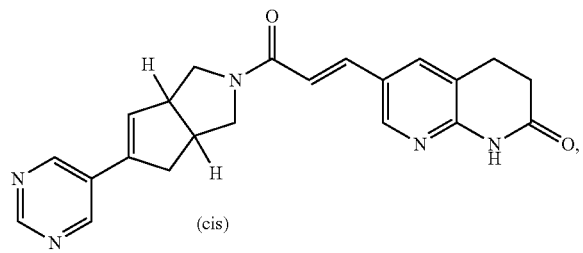
(cis)
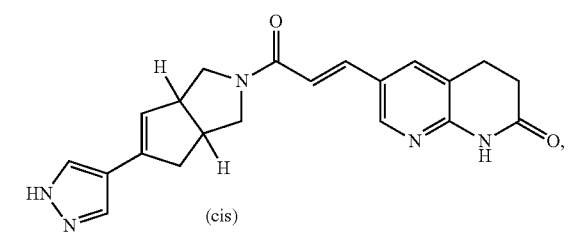
(cis)
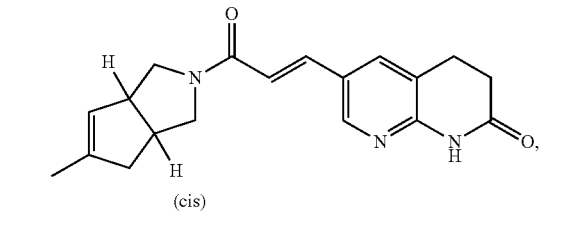
(cis)
-continued
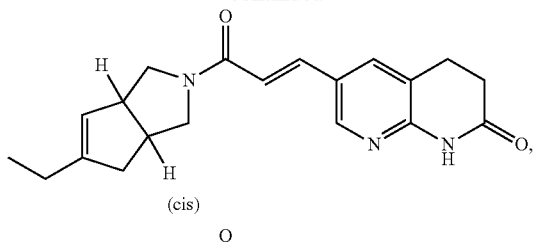
(cis)
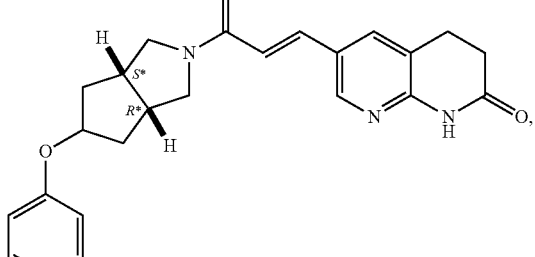
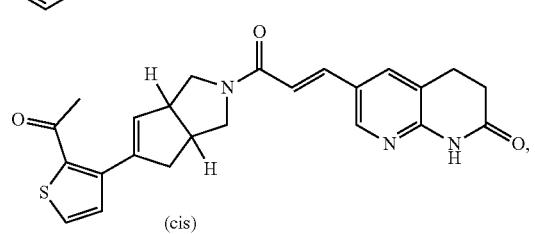
(cis)
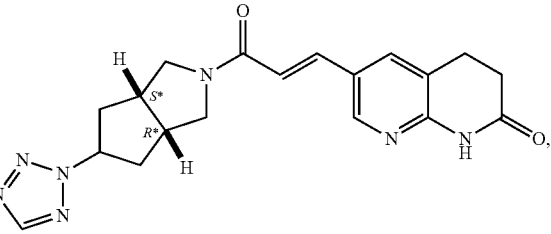
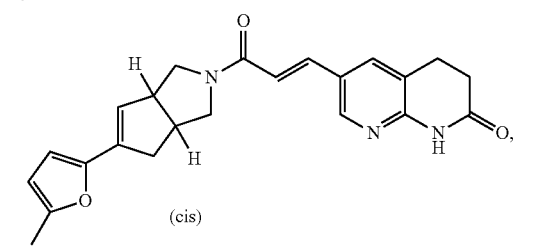
(cis)
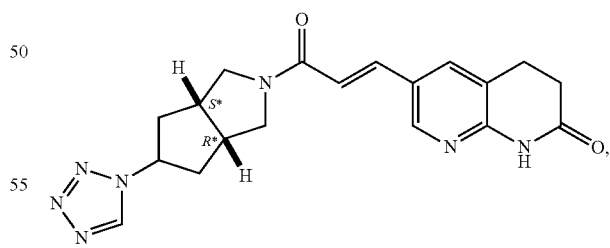
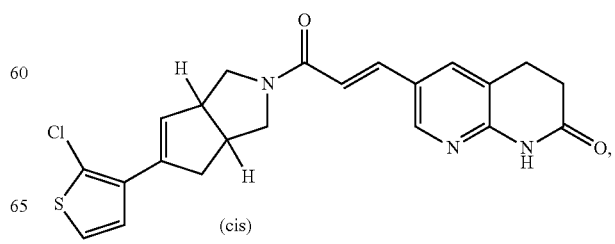
(cis)

-continued and pharmaceutically acceptable salts thereof.

* * * * *

UNITED STATES PATENT AND TRADEMARK OFFICE
CERTIFICATE OF CORRECTION

PATENT NO. : 9,617,262 B2  
APPLICATION NO. : 15/071612  
DATED : April 11, 2017  
INVENTOR(S) : Jérôme Emile Georges Guillemont et al.

Page 1 of 1

It is certified that error appears in the above-identified patent and that said Letters Patent is hereby corrected as shown below:

On the Title Page

Item (54) and in the Specification, Column 1 Line 2 in the title, the word "CYCLOPENTAL[C]PYRROLE" should read --CYCLOPENTA[C] PYRROLE--

Item (63) in the Related U.S. Application Data, the phrase "Continuation of application No. 14/552,108, filed on Nov. 24, 2014, now Pat. No. 9,290,493, which is a continuation of application No. 14/237,862, filed as application No. PCT/EP2012/065733 on Aug. 10, 2012, now Pat. No. 8,906,923." should read --Continuation of application No. 14/552,108, filed on Nov. 24, 2014, which is a continuation of application No. 14/237,862, filed on Feb. 7, 2014, now Pat. No. 8,906,923, which is a 35 U.S.C. § 371 nationalization of PCT application PCT/EP2012/065733, filed on Aug. 10, 2012.--

Signed and Sealed this  
Twelfth Day of June, 2018

Andrei Iancu  
*Director of the United States Patent and Trademark Office*